(12) United States Patent
Weinschenk et al.

(10) Patent No.: US 9,993,540 B2
(45) Date of Patent: Jun. 12, 2018

(54) IMMUNOTHERAPY AGAINST SEVERAL TUMORS INCLUDING NEURONAL AND BRAIN TUMORS

(71) Applicant: IMMATICS BIOTECHNOLOGIES GMBH, Tuebingen (DE)

(72) Inventors: Toni Weinschenk, Aichwald (DE);
Oliver Schoor, Tuebingen (DE);
Claudia Trautwein, Wuelfrath (DE);
Norbert Hilf, Kirchentellinsfurt (DE);
Steffen Walter, Houston, TX (US);
Harpreet Singh, Houston, TX (US)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days. days.

(21) Appl. No.: 15/638,806

(22) Filed: Jun. 30, 2017

(65) Prior Publication Data
US 2017/0326217 A1 Nov. 16, 2017

Related U.S. Application Data

(60) Continuation of application No. 14/562,156, filed on Dec. 5, 2014, which is a division of application No. 13/346,598, filed on Jan. 9, 2012, now Pat. No. 8,961,985, which is a division of application No. 12/571,776, filed on Oct. 1, 2009, now Pat. No. 8,119,139.

(60) Provisional application No. 61/105,928, filed on Oct. 16, 2008.

(30) Foreign Application Priority Data

Oct. 1, 2008 (EP) ...................... 08017305
Oct. 13, 2008 (EP) ...................... 08017921
Sep. 28, 2009 (WO) ............... PCT/EP2009/006980

(51) Int. Cl.
*A61K 35/17* (2015.01)
*A61K 39/00* (2006.01)

(52) U.S. Cl.
CPC .......... *A61K 39/0011* (2013.01); *A61K 35/17* (2013.01); *A61K 2039/5158* (2013.01); *A61K 2039/55511* (2013.01); *A61K 2039/55516* (2013.01); *A61K 2039/55522* (2013.01); *A61K 2039/55561* (2013.01); *A61K 2039/55588* (2013.01); *A61K 2039/572* (2013.01)

(58) Field of Classification Search
CPC .................................................... A61K 35/17
See application file for complete search history.

(56) References Cited

U.S. PATENT DOCUMENTS

| 6,589,642 B1 | 7/2003 | Miller et al. |
| 8,008,431 B2 | 8/2011 | Weinschenk et al. |
| 2002/0090672 A1 | 7/2002 | Rosen et al. |
| 2003/0175733 A1 | 9/2003 | Kirst et al. |
| 2005/0261166 A1 | 11/2005 | Wang et al. |
| 2008/0207497 A1 | 8/2008 | Ramakrishna et al. |
| 2010/0021441 A1 | 1/2010 | Weinschenk et al. |
| 2010/0029573 A1 | 2/2010 | Weinschenk et al. |

FOREIGN PATENT DOCUMENTS

| EP | 2111867 | 4/2009 |
| WO | 983197 A1 | 7/1998 |
| WO | 200155368 | 8/2001 |
| WO | 2007072505 | 8/2001 |
| WO | 2002020036 | 3/2002 |
| WO | 2002046767 | 6/2002 |
| WO | 2002074237 | 9/2002 |
| WO | 2003045998 | 6/2003 |
| WO | 2004015390 | 2/2004 |
| WO | 2005116051 | 12/2005 |
| WO | 0570188 | 6/2007 |
| WO | 2007150077 | 12/2007 |
| WO | 2008109757 | 9/2008 |

OTHER PUBLICATIONS

Lollini et al. (Curr. Cancer Drug Targets. May 2005; 5 (3): 221-228).*
Lollini et al. (Trends Immunol. Feb. 2003; 24 (2): 62-66).*
Slinghuff et al. (Cancer Immunol. Immunother. Mar. 2000; 48 (12): 661-672).*
Arceci (Journal of Molecular Medicine. 1998; 76: 80-93).*
Khong et al. (Nat. Immunol. Nov. 2002; 3 (11): 999-1005; pp. 1-17).*
Neeley et al. (Prostate. May 15, 2008; 68 (7):715-27).*
Restifo et al. (J. Natl. Cancer Inst. Jan. 17, 1996; 88 (2): 100-8; pp. 1-19).*
Liu et al. (J. Immunol. Sep. 15, 2008; 181 (6): 4363-70).*
Bodey et al. (Anticancer Research. 2000; 20: 2665-2676).*
Gura (Science. 1997; 278: 1041-1042).*
Prato et al. (J. Immunol. Oct. 1, 2013; 191 (7): 3534-44).*
Suvasini et al. (J. Biol. Chem. Jul. 22, 2011; 286 (29): 25882-90).*
Shi et al. (Tumour Biol. Apr. 2017; 39 (4): 1-11).*
Schaeffer et al. (BMC Cancer. 2010, 10: 59; pp. 1-8).*
UNIPROT Accession No. A2T6A1; sequence version 1 (Feb. 6, 2007).

(Continued)

*Primary Examiner* — Stephen Rawlings
(74) *Attorney, Agent, or Firm* — McBee Moore Woodward & Vanik IP, LLC; Susan McBee

(57) ABSTRACT

A method of treating a patient who has brain cancer includes administering to said patient a composition containing a population of activated T cells that selectively recognize cells in the patient that aberrantly express a peptide. A pharmaceutical composition contains activated T cells that selectively recognize cells in a patient that aberrantly express a peptide, and a pharmaceutically acceptable carrier, in which the T cells bind to the peptide in a complex with an MHC class I molecule, and the composition is for treating the patient who has brain cancer. A method of treating a patient who has brain cancer includes administering to said patient a composition comprising a peptide in the form of a pharmaceutically acceptable salt, thereby inducing a T-cell response to the brain cancer.

12 Claims, 8 Drawing Sheets

(56) References Cited

OTHER PUBLICATIONS

UNIPROT Accession No. A1YGC8; sequence version 1 (Feb. 6, 2007).
Extended European Search Report, EP 08 01 7921, dated Dec. 14, 2009.
Gunther et al., "Glioblastoma-derived stem cell-enriched cultures from distinct subgroups according to molecular and phenotypic criteria," Oncogen (2008) 27, 00. 2897-2909 (XP-002557755).
Suzuki et al., "Genetic analysis of human glioblastomas using a genomic microarray system," Brain Tumore Pathol (2004) 21, pp. 27-34 (XP-002557756).
Shibahara et al., "Podoplanin is expressed in subsets of tumors of the central nervous system," Virchows Arch (2006) 448, pp. 493-499 (XP-002557757).
International Journal of Cancer, Journal of International DU Cancer, May 18, 1998, vol. 77: 04, pp. 451-458.
Gary et al., "cDNS Cloning, chromosomal localization, and expression analysis of human BEHAB/brevican, a brain specification proteoglycan regulated during cortical development and in glioma," Gene, Elsevier, Amsterdam, NL, vol. 256: 1-2, Oct. 3, 2000, pp. 139-147 (XP-004238299).
International Preliminary Report on Patentability dated Apr. 5, 2011 from PCT/EP2009/006980 and Written Opinion, dated Apr. 1, 2011.
International Search Report dated Mar. 30 2010 from PCT/EP2009/006980.
International Search Report dated Sep. 26, 2008 from PCT/EP2009/006980.
Meydan et al. (BMC Bioinformatics. 2013; 14 (Suppl. 2): S13; pp. 1-12).
Neefjes et al. (Nature Reviews Immunology. Dec. 2011; 11, 823-836).
Walter et al. (J. Immunol. Nov. 15, 2003; 171 (10): 4974-78).
Chen et al. (Arthritis Rheumatol. Feb. 2014; 66 (2): 284-94).
Li et al. (Front. Immunol. Nov. 22, 2013; 4: 383; pp. 1-8).
Obermann et al. (Immunology Sep. 2007; 122 (1): 90-97).
Mizukami et al. (Cancer Sci. Jul. 2008 99(7): 1448-54).
Suda et al. (Cancer Sci. Nov. 2007; 98(1): 1803-08).
Delamarre et al. (Science. Mar. 11, 2005; 307 (5715): 1630-34).
Urban et al. (Proc. Natl. Acad. Sci. USA. Feb. 15, 1994; 91(4): 1534-38).
Chang et al. (Proc. Natl. Acad. Sci. USA. Nov. 22, 2005; 102(47): 17107-12).

\* cited by examiner

ND BRAIN TUMORS

IMMUNOTHERAPY AGAINST SEVERAL TUMORS INCLUDING NEURONAL AND BRAIN TUMORS

CROSS REFERENCE TO RELATED APPLICATIONS

This is a continuation application of U.S. application Ser. No. 14/562,156, filed on May 12, 2014, which is a divisional application of U.S. application Ser. No. 13/346,598 (now U.S. Pat. No. 8,961,985), filed on Jan. 9, 2012, which is a divisional of U.S. application Ser. No. 12/571,776 (Now U.S. Pat. No. 8,119,139), filed on Oct. 1, 2009, which claims priority to U.S. Provisional Application No. 61/105,928, filed on Oct. 16, 2008, EP Application No. 08 017 305.7, filed on Oct. 1, 2008, and EP Application No. 08 017 921.1, filed on Oct. 13, 2008, and International Application No. PCT/EP2009/006980 filed Sep. 28, 2009, each of which is hereby incorporated by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2332.03(a)), a Sequence Listing in the form of an ASCII-compliant text file (entitled "Sequence_Listing_2912919-018011_ST25.txt" created on Jun. 25, 2017, and 4,959 bytes in size) is submitted concurrently with the instant application, and the entire contents of the Sequence Listing are incorporated herein by reference.

BACKGROUND

Field of the Invention

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to 30 peptide sequences and their variants derived from HLA class I and class II molecules of human tumor cells that can be used in vaccine compositions for eliciting anti-tumor immune responses.

Description of Related Art

Gliomas are brain tumors originating from glial cells in the nervous system. Glial cells, commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas, named according to the normal glial cell type from which they originate (astrocytes or oligodendrocytes, respectively). Belonging to the subgroup of astrocytomas, glioblastoma multiforme (referred to as glioblastoma hereinafter) is the most common malignant brain tumor in adults and accounts for approx. 40% of all malignant brain tumors and approx. 50% of gliomas. It aggressively invades the central nervous system and is ranked at the highest malignancy level (grade IV) among all gliomas. Although there has been steady progress in their treatment due to improvements in neuroimaging, microsurgery, diverse treatment options, such as temozolomide or radiation, glioblastomas remain incurable. The lethal rate of this brain tumor is very high: the average life expectancy is 9 to 12 months after first diagnosis. The 5-year survival rate during the observation period from 1986 to 1990 was 8.0%. To date, the five-year survival rate following aggressive therapy including gross tumor resection is still less than 10%. Accordingly, there is a strong medical need for an alternative and effective therapeutic method.

Tumor cells of glioblastomas are the most undifferentiated ones among brain tumors, so the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy.

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years, on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the state with no clinical or pathological abnormalities (Pathology and Genetics of the Nervous Systems. 29-39 (IARC Press, Lyon, France, 2000)).

Glioblastoma migrates along myelinated nerves and spreads widely in the central nervous system. In most cases surgical treatment shows only limited sustainable therapeutic effect. Malignant glioma cells evade detection by the host's immune system by producing immunosuppressive agents that impair T cell proliferation and production of the immune-stimulating cytokine IL-2.

Intracranial neoplasms can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

The search for effective treatment of glioblastomas in patients is still ongoing today. Immunotherapy, or treatment via recruitment of the immune system, to fight these neoplastic cells has been investigated. First encouraging results with immuno-therapeutic approaches in patients suffering from glioblastoma were obtained by Northwest Biotherapeutics using "DCVax Brain", a cell-based vaccination approach employing patient-derived dendritic cells loaded with autologous tumor cell lysates, and by Celldex, which used a peptide from EGFRvIII for inducing antigen-specific CTL responses, which in turn correlated with prolonged median survival times compared to median survival times obtained when using standard treatment (Heimberger et al., 2006).

Colorectal Carcinoma

According to the American Cancer Society, colorectal cancer (CRC) is the third most common cancer in the US, afflicting more than 175,000 new patients each year. In the US, Japan, France, Germany, Italy, Spain and the UK, it affects more than 480,000 patients. It is one of the most common causes of cancer mortality in developed countries. The 1- and 5-year relative survival for persons with colorectal cancer is 84% and 64%, respectively. Survival continues to decline beyond 5 years to 57% at 10 years after diagnosis. When colorectal cancers are detected at an early, localized stage, the 5-year survival is 90%; however, only 39% of colorectal cancers are diagnosed at this stage, mostly due to low rates of screening. After the cancer has spread regionally to involve adjacent organs or lymph nodes, the 5-year survival drops to 68%. For persons with distant metastases, 5-year survival is 10%.

Research suggests that the onset of colorectal cancer is the result of interactions between inherited and environmental factors. In most cases adenomatous polyps appear to be precursors to colorectal tumors; however the transition may take many years. The primary risk factor for colorectal cancer is age, with 90% of cases diagnosed over the age of 50 years. Other risk factors for colorectal cancer according to the American Cancer Society include alcohol consumption, a diet high in fat and/or red meat and an inadequate intake of fruits and vegetables. Incidence continues to rise, especially in areas such as Japan, where the adoption of westernized diets with excess fat and meat intake and a decrease in fiber intake may be to blame. However, incidence rates are rising not as fast as previously which may be due to increasing screening and polyp removal, thus preventing progression of polyps to cancer.

As in most solid tumors, first line treatment is surgery, however, its benefits remain confined to early-stage patients, yet a significant proportion of patients are diagnosed in advanced stages of the disease. For advanced colorectal cancer chemotherapy regimens based on fluorouracil-based regimens are standard of care. The majority of these regimens are the so-called FOLFOX (infusional 5-FU/leucovorin plus oxaliplatin) and FOLFIRI (irinotecan, leucovorin, bolus and continuous-infusion 5-FU) protocols.

The introduction of third-generation cytotoxics such as irinotecan and oxaliplatin has raised the hope of significantly improving efficacy, but prognosis is still relatively poor, and the survival rate generally remains at approximately 20 months in metastatic disease and, as a result, the unmet needs in the disease remain high.

Recently a novel generation of drugs, molecular-targeted agents, such as Avastin® (bevacizumab) and Erbitux® (cetuximab), became available and about 40 compounds are in late-stage clinical development for different stages of colorectal cancer. Combinations of several of these compounds increase the number of potential treatment options to be expected for the future. The vast majority of substances are in phase 2, with the EGFR being addressed by these compounds more often than any other target in colorectal cancer trials, which is due to the fact that in ~80% of patients with colorectal cancer EGFR expression is upregulated.

Clinical trials with stage II patients combining chemotherapy with the recently approved monoclonal antibodies (mAbs) (cetuximab+irinotecan or FOLFOX4; bevacizumab as a single-agent or together with FOLFOX4) are currently being conducted. Three to four year observation periods are expected for statistically significant results from these trials.

Monoclonal antibodies (mAbs) presently used in oncology in general have an excellent chance of not interfering with active immunotherapy. In fact, there is preclinical (GABRILOVICH 1999) and clinical evidence suggesting that depletion of VEGF (by bevacizumab) contributes positively to DC-mediated activation of T-cells (Osada T, Chong G, Tansik R, Hong T, Spector N, Kumar R, Hurwitz H I, Dev I, Nixon A B, Lyerly H K, Clay T, Morse M A. The effect of anti-VEGF therapy on immature myeloid cell and dendritic cells in cancer patients. Cancer Immunol Immunother. 2008 Jan. 10.).

Prostate Carcinoma and Other Tumors

With an estimated 27,050 deaths in 2007, prostate cancer is a leading cause of cancer death in men. Although death rates have been declining among white and African American men since the early 1990s, rates in African American men remain more than twice as high as those in white men. Prostate cancer is the most frequently diagnosed cancer in men. For reasons that remain unclear, incidence rates are significantly higher in African American men than in white men. Incidence rates of prostate cancer have changed substantially over the last 20 years: rapidly increasing from 1988-1992, declining sharply from 1992-1995, and increasing modestly since 1995. These trends in large part reflect increased prostate cancer screening with the prostate-specific antigen (PSA) blood test. Moderate incidence increases in the last decade are most likely attributable to widespread PSA screening among men younger than 65. Prostate cancer incidence rates have leveled off in men aged 65 years and older. Rates peaked in white men in 1992 (237.6 per 100,000 men) and in African American men in 1993 (342.8 per 100,000 men).

Treatment for prostate cancer may involve watchful waiting, surgery, radiation therapy, High Intensity Focused Ultrasound (HIFU), chemotherapy, cryosurgery, hormonal therapy, or some combination. Which option is best depends on the stage of the disease, the Gleason score, and the PSA level. Other important factors are the man's age, his general health, and his feelings about potential treatments and their possible side effects. Because all treatments can have significant side effects, such as erectile dysfunction and urinary incontinence, treatment discussions often focus on balancing the goals of therapy with the risks of lifestyle alterations.

If the cancer has spread beyond the prostate, treatment options significantly change, so most doctors who treat prostate cancer use a variety of nomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease which has spread beyond the prostate. However, there are exceptions: radiation therapy may be used for some advanced tumors, and hormonal therapy is used for some early stage tumors. Cryotherapy, hormonal therapy, and chemotherapy may also be offered if initial treatment fails and the cancer progresses.

In a significant number of patients with prostate carcinoma who undergo radical prostatectomy because of clinically suspected organ-limited growth, a definitive histological workup of the surgical preparation shows a locally extensive tumor extending beyond the borders of the organ. These patients have a high risk for early local recurrence, usually detectable as an increasing PSA level in terms of a biochemical relapse. Therapeutic options in this situation include external radiotherapy and hormone ablation; however, the value of these therapeutic approaches, especially with respect to prolonging the patient's long-term survival, must not be regarded as proven. In addition, possible treatment-associated complications such as the development of urethral strictures (radiotherapy), loss of libido and impotence, the risk of a reduction in skeletal calcium salts in terms of osteoporosis, and a markedly increased risk of pathologic bone fractures (hormone ablation) must be considered.

More than 90% of all prostate cancers are discovered in the local and regional stages; the 5-year relative survival rate for patients whose tumors are diagnosed at these stages approaches 100%. Over the past 25 years, the 5-year survival rate for all stages combined has increased from 69% to nearly 90%. According to the most recent data, relative 10-year survival is 93% and 15-year survival is 77%. The dramatic improvements in survival, particularly at 5 years, are partly attributable to earlier diagnosis and improvements in treatment. Nevertheless, the survival rate drops significantly after the spreading to other tissues and organs.

Lung Cancer

Estimated 210,000 new cases are expected in 2007 in the USA, accounting for about 15% of cancer diagnoses. The incidence rate is declining significantly in men, from a high of 102 cases per 100,000 in 1984 to 78.5 in 2003. In women, the rate is approaching a plateau after a long period of increase. Lung cancer is classified clinically as small cell (13%) or non-small cell (87%) for the purposes of treatment.

Lung cancer accounts for the most cancer-related deaths in both men and women. An estimated 160,390 deaths, accounting for about 29% of all cancer deaths, are expected to occur in 2007. Since 1987, more women have died each year from lung cancer than from breast cancer. Death rates have continued to decline significantly in men from 1991-2003 by about 1.9% per year. Female lung cancer death rates are approaching a plateau after continuously increasing for several decades. These trends in lung cancer mortality reflect the decrease in smoking rates over the past 30 years.

Treatment options are determined by the type (small cell or non-small cell) and stage of cancer and include surgery, radiation therapy, chemotherapy, and targeted biological therapies such as bevacizumab (Avastin®) and erlotinib (Tarceva®). For localized cancers, surgery is usually the treatment of choice. Recent studies indicate that survival with early-stage, non-small cell lung cancer is improved by chemotherapy following surgery. Because the disease has usually spread by the time it is discovered, radiation therapy and chemotherapy are often used, sometimes in combination with surgery. Chemotherapy alone or combined with radiation is the usual treatment of choice for small cell lung cancer; on this regimen, a large percentage of patients experience remission, which is long lasting in some cases.

The 1-year relative survival for lung cancer has slightly increased from 37% in 1975-1979 to 42% in 2002, largely due to improvements in surgical techniques and combined therapies. However, the 5-year survival rate for all stages combined is only 16%. The survival rate is 49% for cases detected when the disease is still localized; however, only 16% of lung cancers are diagnosed at this early stage.

There thus remains a need for new efficacious and safe treatment option for glioblastoma, prostate tumor, breast cancer, esophageal cancer, colorectal cancer, clear cell renal cell carcinoma, lung cancer, CNS, ovarian, melanoma, pancreatic cancer, squamous cell carcinoma, leukemia and medulloblastoma and other tumors which show an overexpression of survivin and/or the other proteins of the present invention, enhancing the well-being of the patients without using chemotherapeutic agents or other agents which may lead to severe side effects.

SUMMARY OF THE INVENTION

In a first aspect thereof, the present invention relates to a peptide comprising a sequence selected from the group of SEQ ID NO:1 to SEQ ID NO:30, or a variant thereof that is at least 85% homologous to SEQ ID NO:1 to SEQ ID NO:30, or a variant thereof that induces T cells cross-reacting with said variant peptide; wherein said peptide is not the full-length polypeptide of human survivin. Preferably, said peptide is selected from a peptide having a specific HLA-subtype, such as HLA-A*02 or HLA-DR.

In a second aspect thereof, the present invention relates to a nucleic acid, encoding a peptide according to the present invention or an expression vector capable of expressing said nucleic acid.

In a third aspect thereof, the present invention relates to a host cell comprising the nucleic acid or the expression vector according to the present invention, wherein said host cell preferably is an antigen presenting cell, in particular a dendritic cell or antigen presenting cell.

In a fourth aspect thereof, the present invention relates to an in vitro method for producing activated cytotoxic T lymphocytes (CTL), comprising contacting in vitro CTL with antigen loaded human class I MHC molecules expressed on the surface of a suitable antigen-presenting cell or an artificial construct mimicking an antigen-presenting cell for a period of time sufficient to activate said CTL in an antigen specific manner, wherein said antigen is a peptide according to the present invention.

In a fifth aspect thereof, the present invention relates to the use of a peptide according to the present invention, the nucleic acid or the expression vector according to the present invention, the cell according to the present invention, or an activated cytotoxic T lymphocyte produced according to the present invention for the treatment of cancer or for the manufacture of a medicament against cancer, wherein said medicament preferably is a vaccine. Preferably, said cancer is selected from astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, gangliogliomas, gangliocytoma, central gangliocytoma, primitive neuroectodermal tumors (PNET, e.g. medulloblastoma, medulloepithelioma, neuroblastoma, retinoblastoma, ependymoblastoma), tumors of the pineal parenchyma (e.g. pineocytoma, pineoblastoma), ependymal cell tumors, choroid plexus tumors, neuroepithelial tumors of uncertain origin (e.g. gliomatosis cerebri, astroblastoma), glioblastoma prostate tumor, breast cancer, esophageal cancer, colon cancer, colorectal cancer, renal cell carcinoma, clear cell renal cell carcinoma, lung cancer, CNS, ovarian, melanoma pancreatic cancer, squamous cell carcinoma, leukemia and medulloblastoma, and other tumors or cancers showing an overexpression of Survivin and/or the other proteins of the present invention.

In a sixth aspect thereof, the present invention relates to a kit, comprising: (a) a container that contains a pharmaceutical composition containing a peptide according to the present invention, the nucleic acid or the expression vector according to the present invention, a cell according to the present invention, or an activated cytotoxic T lymphocyte according to the present invention, in solution or in lyophilized form; (b) optionally, a second container containing a diluent or reconstituting solution for the lyophilized formulation; (c) optionally, at least one peptide selected from the group consisting of the peptides according to SEQ ID NOs 1 to 30, and (d) optionally, instructions for the use of the solution and/or the reconstitution and/or use of the lyophilized formulation. In a preferred embodiment the peptide is selected from the group of SEQ ID NOs 1 to SEQ ID:24.

In a seventh aspect thereof, the present invention relates to a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen.

In an eighth aspect thereof, the present invention relates to an antibody that specifically binds to a human major histocompatibility complex (MHC) class I or II being complexed with a HLA-restricted antigen, wherein the antibody preferably is a polyclonal antibody, monoclonal antibody and/or a chimeric antibody.

DETAILED DESCRIPTION OF A PREFERRED EMBODIMENT

Figure 1A:
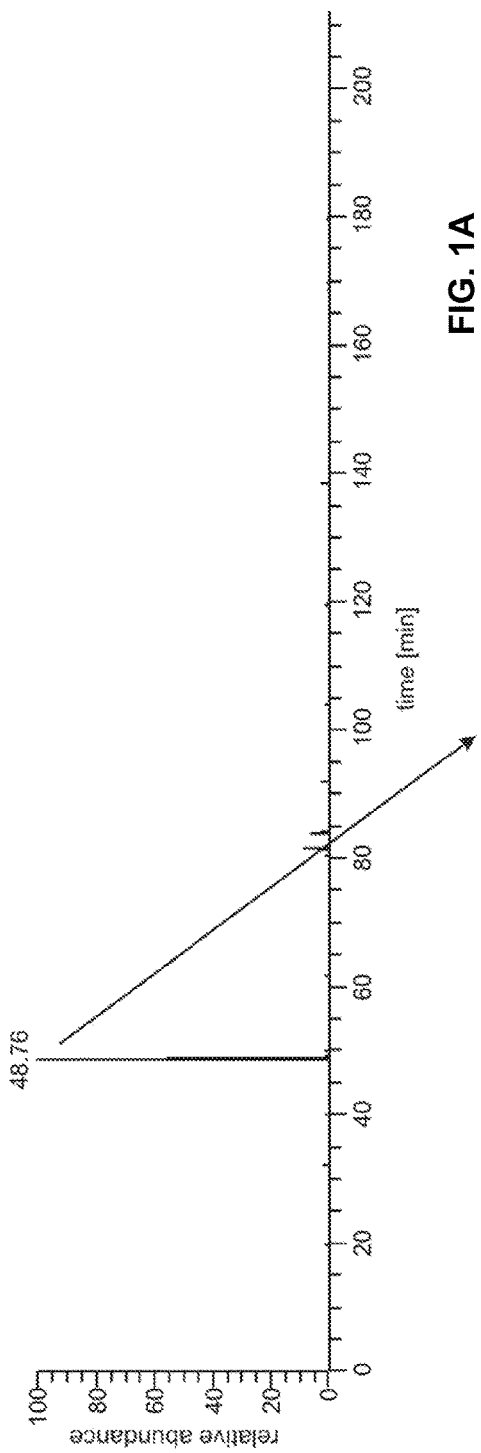
FIGS. 1A through 1D demonstrate the ESI-liquid chromatography mass spectra identifying tumor associated peptides (TUMAPs) IGF2BP3-001 from glioblastoma sample GB6010 that was presented in a MHC class I restricted manner.

As used herein and except as noted otherwise all terms are defined as given below.

The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 16 or 10, 11, 12, 13, 14 or 15 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein, or polynucleotide coding for such a molecule is "immunogenic" (and thus an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A T cell "epitope" requires a short peptide that is bound to a class I or II MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length. T cell epitopes that bind to MHC class II molecules are typically 12-30 amino acids in length. In the case of peptides that bind to MHC class II molecules, the same peptide and the corresponding T cell epitope may share a common core segment, but differ in the overall length due to flanking sequences of differing lengths upstream of the amino-terminus of the core sequence and downstream of its carboxy-terminus, respectively. MHC class II receptors have a more open conformation, peptides bound to MHC class II receptors are correspondingly not completely buried in the structure of the MHC class II molecule peptide-binding cleft as they are in the MHC class I molecule peptide-binding cleft. Surprisingly this is not the case for the peptide according to SEQ ID NO:1, as small variations in the length of the peptide lead to an extreme decrease of activity (see below).

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-A*11 are examples of different MHC class I alleles that can be expressed from these loci.

There are three different loci in the human genome for MHC class II genes: HLA-DR, HLA-DQ, and HLA-DP. MHC class II receptors are heterodimers consisting of an alpha and a beta chain, both anchoring in the cell membrane via a transmembrane region. HLA-DRB1*04, and HLA-DRB1*07 are two examples of different MHC class II beta alleles that are known to be encoded in these loci. Class II alleles are very polymorphic, e.g. several hundred different HLA-DRB1 alleles have been described. Therefore, for therapeutic and diagnostic purposes a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

The term "expression product" means the polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, the claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO: 1 to 30, which correspond to the naturally occurring, or "parent" proteins of the SEQ ID NO: 1 to 30. When used in relation to polynucleotides, such terms refer to the products produced by treatment of said polynucleotides with any of the common endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[I-(C/R)]$ wherein C is the number of differences between the Reference Sequence and the Compared Sequence over the length of alignment between the Reference Sequence and the Compared Sequence, wherein
(i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference;
and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated Percent Identity is less than the specified Percent Identity.

The original peptides disclosed herein can be modified by the substitution of one or more residues at different, possibly selective, sites within the peptide chain, if not otherwise stated. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation. For MHC class II-restricted T helper cells, effector functions may be peptide induced secretion of cytokines, preferably, IFN-gamma, TNF-alpha, IL-4, ILS, IL-10, or IL-2, or peptide-induced degranulation. Possible effector functions for CTLs and T helper cells are not limited to this list.

Preferably, when the CTLs specific for a peptide of SEQ IDs NO: 1 to 30 are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 µM, and most preferably no more than about 10 µM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity.

Stimulation of an immune response is dependent upon the presence of antigens recognized as foreign by the host immune system. The discovery of the existence of tumor associated antigens has now raised the possibility of using a host's immune system to foster an immune response that is specific for target antigens expressed on the surface of tumor cells and which through this mechanism of action is capable of inducing regression, stasis or slowed-down growth of the tumor. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T cells (CTL) from tumor-infiltrating cell populations or from peripheral blood suggests that such cells play an important role in natural immune defenses against cancer (Cheever et al., 1993; Zeh, III et al., 1999). Based on the analysis of 415 specimens from patients suffering from colorectal cancer, Galon et al. were able to demonstrate that type, density and location of immune cells in tumor tissue are actually a better predictor for survival of patients than the widely employed TNM-staging of tumors (Galon et al., 2006).

MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed (Cres swell, 1994). Complexes of peptide and MHC class I molecules are recognized by CD8-positive cytotoxic T-lymphocytes bearing the appropriate TCR (T-cell receptor), and complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells (Wang and Livingstone, 2003; Sun and Bevan, 2003; Shedlock and Shen, 2003). Initially, the priming and expansion of CTLs in lymph nodes is supported by CD4+ T-cells (Schoenberger et al., 1998). One mechanism therefore might be the guidance of naive CD8+ cells to the place of functional CD4+ T-cell—APC interaction (Castellino et al., 2006). Finally, the generation of functional CD8+ memory cells is in most cases dependent on CD4+ T-cell assistance (Sun and Bevan, 2003; Janssen et al., 2003). For these reasons, the identification of CD4-positive T-cell epitopes derived from tumor associated antigens (TAA) is of great importance for the development of pharmaceutical products for triggering anti-tumor immune responses (Kobayashi et al., 2002; Qin et al., 2003; Gnjatic et al., 2003). At the tumor site, T helper cells, support a CTL friendly cytokine milieu (Qin and Blankenstein, 2000; Mortara et al., 2006) and attract effector cells, e.g. CTLS, NK cells, macrophages, granulocytes (Marzo et al., 2000; Hwang et al., 2007).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have surprisingly been found to express MHC class II molecules (Dengjel et al., 2006).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ) (Qin and Blankenstein, 2000). Also the direct killing of tumor cells by cytotoxic CD4+ T cells via lymphotoxins and granzyme B has been proposed (Penna et al., 1992; Littaua et al., 1992).

Additionally, it was shown that CD4-positive T cells recognizing peptides from tumor-associated antigens presented by HLA class II molecules can counteract tumor progression via the induction of antibody (Ab) responses (Kennedy et al., 2003).

In contrast to tumor-associated peptides binding to HLA class I molecules, only a small number of class II ligands of tumor associated antigens (TAA) have been described to date.

Since the constitutive expression of HLA class II molecules is usually limited to cells of the immune system (Mach et al., 1996), the possibility of isolating class II peptides directly from primary tumors was not considered possible. However, Dengjel et al. were recently successful in identifying a number of MHC Class II epitopes directly from tumors (WO 2007/028574, EP 1 760 088 B1; (Dengjel et al., 2006).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens (TAAs) comprises the following major groups (Novellino et al., 2005):

1. Cancer-testis antigens: The first TAAs ever identified that can be recognized by T cells (van der Bruggen et al., 1991) belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

2. Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

3. Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

4. Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

5. TAAs arising from abnormal post-translational modifications: Such TAAs may arise from proteins that are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation, which may or may not be tumor specific (Hanada et al., 2004; Vigneron et al., 2004).

6. Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and in order to be used in a therapy, particular prerequisites must be fulfilled. The antigen should be expressed mainly by tumor cells and not or in comparably small amounts by normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, also downstream targets of the proteins directly causative for a transformation may be upregulated and thus may be indirectly tumor-associated. Such indirectly tumor-associated antigens may also be targets of a vaccination approach (Singh-Jasuja et al., 2004). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel et al., 2004; Weinschenk et al., 2002).

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell that upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the $T_{H1}$ type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive T-helper cells (ligand: MHC class II molecule+peptide epitope) is important in the development of tumor vaccines. Considering the severe side-effects and expense associated with treating cancer better prognosis and diagnostic methods are desperately needed. Therefore, there is a need to identify other factors representing biomarkers for cancer in general and glioblastoma in particular. Furthermore, there is a need to identify factors that can be used in the treatment of cancer in general and glioblastoma in particular, Furthermore there is no established therapeutic design for prostate cancer patients with biochemical relapse after radical prostatectomy, usually caused by residual tumor left in situ in the presence of locally advanced tumor growth. New therapeutic approaches that confer lower morbidity with comparable therapeutic efficacy relative to the currently available therapeutic approaches would be desirable.

The present invention provides peptides that are useful in treating glioblastoma, prostate cancer and other tumors that overexpress survivin and/or CSP and/or other peptides of the invention. These peptides were partly directly shown by mass spectrometry to be naturally presented by HLA molecules on primary human glioblastoma samples (see example 1 and FIGS. 1A through 1D), or in the case of SEQ ID NO:26 predicted according to the SYFPEITHI prediction algorithm (Rammensee et al., 1995) to be promiscuous binders to the HLA-DR alleles HLA-DRB1*01, DRB1*03, DRB1*04, DRB1*11, and DRB1*15. Based on this data and the frequencies of these frequent DRB1 alleles, it can be assumed that 92% of A*02-positive Caucasians express at least one DRB1 allele that binds the peptide according to SEQ ID NO:26.

The source gene from which SEQ ID NO: 26 to 30 are derived—survivin—was shown to be highly overexpressed in glioblastoma, prostate tumor, breast cancer, esophageal cancer, colorectal cancer, clear cell renal cell carcinoma, lung cancer, CNS, ovarian, melanoma (Tamm et al. 1998) pancreatic cancer, squamous cell carcinoma, leukemia and medulloblastoma compared with normal tissues (see example 2 and FIGS. 2A through 2D) demonstrating a high degree of tumor association of the peptide, i.e. these peptides are strongly presented on tumor tissue but not on normal tissues. WO 2004/067023 describes MHC Class I-restricted peptides derived from the tumor associated antigen survivin, which peptides are capable of binding to Class I HLA molecules at a high affinity.

HLA-bound peptides can be recognized by the immune system, specifically T lymphocytes/T cells. T cells can destroy the cells presenting the recognized HLA/peptide complex, e.g. glioblastoma tumor cells presenting the derived peptides. T helper cells activated by the survivin-derived peptides can inhibit tumor vascularization, can attract effector cells of the immune system and facilitate CTL priming, proliferation, and a sustained CD8+ T-cell response.

Figure 3:
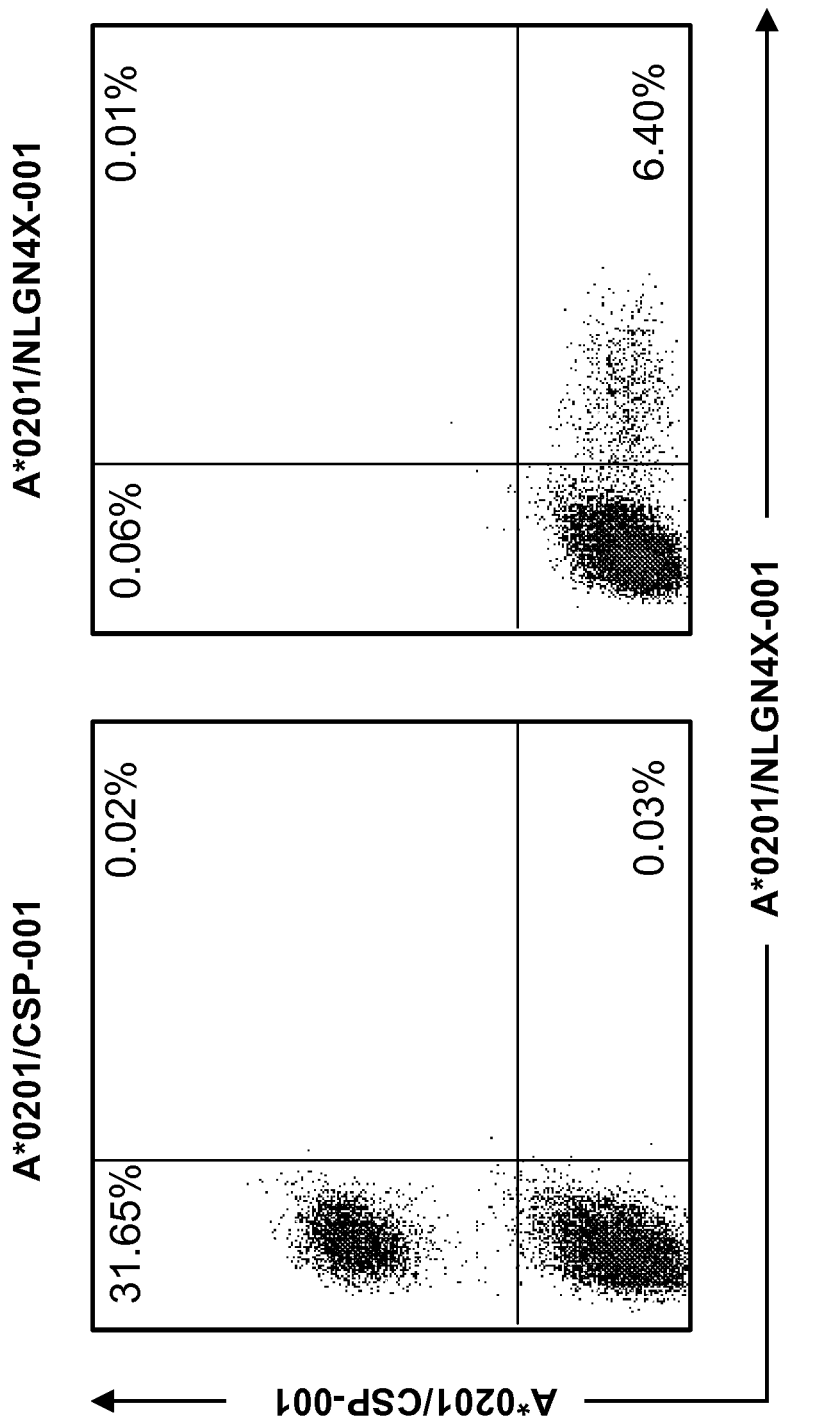
FIG. 3 shows the tetramer analysis of microsphere driven proliferation of CSP-001 and NLGN4X-001 specific CD8+ lymphocytes from peripheral blood of a healthy donor. $1\times10^6$ CD8+ enriched PBMCs per well were stimulated weekly with microspheres coupled to anti-CD28 plus high density tumor antigen A*0201/CSP-001 (left panel) or anti-CD28 plus high density tumor antigen A*0201/NLGN4X-001 (right panel). After three stimulations in vitro, all cells were stained with antibody CD8 FITC, and fluorescently-labeled tetramers A*0201/CSP-001 and A*0201/NLGN4X-001. Cells are gated on CD8+ lymphocytes; numbers represent percentage of cells in the indicated quadrant among CD8+ lymphocytes.

All peptides of the present invention have been shown to be capable of stimulating T cell responses (see Example 3 and FIG. 3). Thus, the peptides are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

The pharmaceutical compositions comprise the peptides either in the free form or in the form of a pharmaceutically acceptable salt.

As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH2 group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment the pharmaceutical compositions comprise the peptides as salts of acetic acid (acetates) or hydrochloric acid (chlorides).

In addition to being useful for treating cancer, the peptides of the present invention are also useful as diagnostics. Since the peptides were generated from glioblastoma and since it was determined that these peptides are not present in normal tissues, these peptides can be used to diagnose the presence of a cancer.

The presence of claimed peptides on tissue biopsies can assist a pathologist in diagnosis of cancer. Detection of certain peptides by means of antibodies, mass spectrometry or other methods known in the art can tell the pathologist that the tissue is malignant or inflamed or generally diseased. Presence of groups of peptides can enable classification or sub-classification of diseased tissues.

The detection of peptides on diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of peptides shows that this mechanism is not exploited by the analyzed cells.

The peptides might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases. The peptides can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

In addition, they can be used to verify a pathologist's diagnosis of a cancer based on a biopsied sample.

Table 1 shows the peptides according to the present invention, their respective SEQ ID NO:, the HLA alleles to which the respective peptides bind, and the source proteins from which these peptides may arise. Of special interest is the fact that the peptide according to SEQ ID NO:1 binds to HLA-DR as well as HLA-A*02 thus eliciting two different responses.

TABLE 1

Peptides of the present invention

| SEQ ID NO: | Peptide Code | Sequence | HLA Alleles | Source Protein(s) |
|---|---|---|---|---|
| 1 | NLGN4X-001 | NLDTLMTYV | HLA-A*02 | NLGN4X |
| 2 | SLC01C1-001 | YLIAGIISL | HLA-A*02 | SLC01C1 |
| 3 | ACS-001 | KIMERIQEV | HLA-A*02 | ACSBG1 |
| 4 | BCA-001 | FLGDPPEKL | HLA-A*02 | BCAN |

TABLE 1-continued

Peptides of the present invention

| SEQ ID NO: | Peptide Code | Sequence | HLA Alleles | Source Protein(s) |
|---|---|---|---|---|
| 5 | BCA-002 | ALWAWPSEL | HLA-A*02 | BCAN |
| 6 | CHI3L1-010 | TLYGMLNTL | HLA-A*02 | CHI3L1 |
| 7 | CLIP2-001 | SLNELRVLL | HLA-A*02 | CLIP2 |
| 8 | DTNA-001 | KLQDEAYQV | HLA-A*02 | DTNA |
| 9 | EGFR-007 | ALAVLSNYDA | HLA-A*02 | EGFR |
| 10 | FABP7-001 | LTFGDVVAV | HLA-A*02 | FABP7 |
| 11 | GFAP-001 | NLAQDLATV | HLA-A*02 | GFAP |
| 12 | GPR56-002 | FLLSEPVAL | HLA-A*02 | GPR56 |
| 13 | GRI-001 | NILEQIVSV | HLA-A*02 | GRIA4 |
| 14 | IGF2BP3-001 | KIQEILTQV | HLA-A*02 | IGF2BP3 |
| 15 | MLC-001 | SVVEVIAGI | HLA-A*02 | MLC1 |
| 16 | NES-001 | GLQSQIAQV | HLA-A*02 | NES |
| 17 | NES-002 | SLQENLESL | HLA-A*02 | NES |
| 18 | NES-003 | FLFPGTENQEL | HLA-A*02 | NES |
| 19 | NES-004 | NLAEELEGV | HLA-A*02 | NES |
| 20 | NR2E1-001 | KIISEIQAL | HLA-A*02 | NR2E1 |
| 21 | NRCAM-001 | GLWHHQTEV | HLA-A*02 | NRCAM |
| 22 | PDPN-001 | TLVGIIVGV | HLA-A*02 | PDPN |
| 23 | TNC-001 | AMTQLLAGV | HLA-A*02 | TNC |
| 24 | TNC-002 | QLLAGVFLA | HLA-A*02 | TNC |
| 25 | CSP-001 | TMLARLASA | HLA-A*02 | CSPG4 |
| 26 | BIR-002 | TLGEFLKLDRERAKN | HLA-DR and HLA-A*02 | BIRC5/Survivin |
| 27 | BIR-002a | TLGEFLKLDRERAKD | HLA-DR | BIRC5/Survivin |
| 28 | BIR-002b | FTELTLGEF | HLA-A1 | BIRC5/Survivin |
| 29 | BIR-002c | LMLGEFLKL | HLA-A2 | BIRC5/Survivin |
| 30 | BIR-002d | EPDLAQCFY | HLA-B35 | BIRC5/Survivin |

Chondroitin Sulfate Proteoglycan 4 (CSPG4)

CSPG4 (chondroitin sulfate proteoglycan) represents an integral membrane chondroitin sulfate proteoglycan on nascent pericytes with a functional role in neovascularization (Ozerdem, 2006). During embryogenesis, the CSPG4 proteoglycan is expressed on immature capillary vessels, but as the vessels mature they lose this expression. It is known as an early cell surface melanoma progression marker implicated in stimulating tumor cell proliferation, migration and invasion. CSPG4 is strongly expressed on >90% of human melanoma lesions. Although CSPG4 is not strictly tumor specific, tumor-reactive CD4+ T-cell responses in melanoma patients and healthy individuals recognize CSPG4$_{693-709}$ on HLA-DR11-expressing melanoma cells in the absence of autoimmunity (Erfurt et al., 2007).

Expression of CSPG4 enhances integrin-mediated cell spreading, FAK (focal adhesion kinase) phosphorylation, and activation of ERK1/2 (extracellular signal-regulated kinase) (Yang et al., 2004). Furthermore, there is accumulating evidence from in vitro data that CSPG4 plays an important role in tumor angiogenesis. Thus, CSPG4-positive tumors have been found to have significantly increased neovascularization rates and vascular volumes, and CSPG4 has been shown to sequester angiostatin, which normally inhibits endothelial cell proliferation and angiogenesis. Immature vessels also contain CSPG4-positive pericytes, suggesting a role for this cell population in modulating endothelial cell proliferation by blocking the inhibitory effects of angiostatin during vessel development (Chekenya et al., 2002b).

CSPG4 expression has also been described in some normal tissues besides activated pericytes such as endothelial cells, chondrocytes, smooth muscle cells, certain basal keratinocytes within the epidermis, as well as cells within the hair follicle (Campoli et al., 2004).

During angiogenesis and in response to CNS pathologies, the highly motile CSPG4 cells undergo rapid morphological changes and are recruited to sites where vessel growth and repair are occurring. CSPG4 is over-expressed by both tumor cells and pericytes on the blood vessels of malignant brain tumors (Chekenya and Pilkington, 2002). By implanting cells from an CSPG4-positive human glioma cell line into immunodeficient nude rat brains it was shown that these tumors had a higher microvascular density in comparison to controls implying that CSPG4 expression regulates both the function and the structure of the host-derived tumor vasculature (Brekke et al., 2006). In a xenograft experiment of implantation of GBM biopsy spheroids into nude rats, CSPG4 was identified to be mainly associated with blood vessels on both the pericyte and basement membrane components of the tumor vasculature and the expression was also associated with areas of high cellular proliferation (Chekenya et al., 2002a). Furthermore, CSPG4 expression paralleled progression of the tumor in a glioma implantation model (Wiranowska et al., 2006). Malignant progression is maintained by cross-talk between the tumor and its stroma, where the activated stroma nurtures the proliferative and invasive neoplastic cells, by providing neovasculature, extracellular matrix components, and stimulatory growth factors. In this context, CSPG4 plays a major role in tumor-stroma activation through alterations in cellular adhesion, migration, proliferation, and vascular morphogenesis (Chekenya and Immervoll, 2007).

CSPG4 is differentially expressed in human gliomas with higher expression in high compared to low-grade gliomas (Chekenya et al., 1999). High expression of CSPG4 correlates with multidrug resistance mediated by increased activation of α3β1 integrin/PI3K signaling and their downstream targets, promoting cell survival (Chekenya et al., 2008).

CSP-001 was found in the following organs/tissues and cancers:
Brain:—glioblastoma;—secondary glioblastoma (derived from astrocytoma)
Colon:—adenocarcinoma (excluding mucinous type), primary;
Rectum:—adenocarcinoma, metastasis
Stomach:—adenocarcinoma (excluding signet ring cell type), primary
Kidney:—renal cell carcinoma, cell line;—renal cell carcinoma, clear cell type, metastasis, all secondary sites;—renal cell carcinoma, clear cell type, primary;—renal cell carcinoma, primary
Lung:—adenocarcinoma, primary;—adenosquamous carcinoma, primary;—primary cancer;—small cell carcinoma, primary;—squamous cell carcinoma, primary;
Pancreas:—adenocarcinoma, primary;—islet cell tumor, malignant, metastasis
Prostate:—adenocarcinoma, primary
Skin:—metastatic malignant melanoma, lymph node metastasis Therefore, a pharmaceutical composition containing a peptide according to SEQ ID NO:1 is particularly preferred for the treatment of
Brain:—glioblastoma;—secondary glioblastoma (derived from astrocytoma)
Colon:—adenocarcinoma (excluding mucinous type), primary;
Rectum:—adenocarcinoma, metastasis
Stomach:—adenocarcinoma (excluding signet ring cell type), primary
Kidney:—renal cell carcinoma, cell line; renal cell carcinoma, clear cell type, metastasis, all secondary sites; renal cell carcinoma, clear cell type, primary; renal cell carcinoma, primary
Lung:—adenocarcinoma, primary; stage I,—adenosquamous carcinoma, primary;—primary cancer;—small cell carcinoma, primary;—squamous cell carcinoma, primary;
Pancreas:—adenocarcinoma, primary;—islet cell tumor, malignant, metastasis
Prostate:—adenocarcinoma, primary
Skin:—metastatic malignant melanoma, lymph node metastasis Acyl-CoA Synthetase Bubblegum Family Member 1 (ACSBG1)

The protein encoded by this gene possesses long-chain acyl-CoA synthetase activity. It is thought to play a central role in brain in activation of very long-chain fatty acids metabolism and myelinogenesis. Activation of fatty acids by thioesterification to Acetyl-CoA is a prerequisite of most reactions involving this class of molecules. Cancer-specific functions or over-expression has not yet been described in literature. The expression pattern of ACSBG1 in brain, adrenal gland, testis, and ovary and its function suggests a role of this protein in the biochemical pathology of X-linked adrenoleukodystrophy (XALD). XALD is a severe, often fatal, neurodegenerative disorder characterized by elevated plasma and tissue levels of saturated very long-chain fatty acids (Asheuer et al., 2005; Pei et al., 2003).

Brevican (BCAN)

Brevican is an extracellular matrix protein that is highly expressed at birth expressed from birth through 8 years of age and is downregulated by 20 years of age to low levels that are maintained in the normal adult cortex. A GPI isoform is expressed at uniformly low levels throughout development (Gary et al., 2000). Malignant gliomas aggressively invade the surrounding normal brain which might be mediated by tissue- or tumor-specific extracellular proteins. Thus the extracellular matrix can modulate, in part, the permissiveness of a tissue to cell movement. Accordingly, the ability of gliomas to modify the ECM of the CNS may mediate the invasiveness of these cells. One ECM molecule that shows dramatic upregulation in gliomas is BCAN, a brain specific chondroitin sulfate proteoglycan. BCAN expression is also upregulated during periods of increased glial cell motility in development and following brain injury. In glioma an approximately sevenfold increase in expression over normal levels can be detected (Gary et al., 2000; Gary et al., 1998). In addition to upregulation of BCAN in glioma, proteolytic processing of the full-length protein also may contribute to invasion (Gary et al., 1998; Nutt et al., 2001). It could be shown that the proteolytic processing of BCAN by metalloproteases of the ADAMTS family is a necessary step in mediating its pro-invasive effect in glioma. The mutant, "uncleavable" form of BCAN is unable to enhance glioma cell invasion in vitro and tumor progression in vivo (Viapiano et al., 2008). mRNA for BCAN is not detectable in normal adult human cortex or in any nonglioma tumor, thus BCAN is considered to be a unique and selective marker in glioma (Jaworski et al., 1996). Furthermore, protein analysis disclosed not only an increased expression of the full-length BCAN but also the presence of additional, unique isoforms in glioma. Thus, $B/b_{Ag}$ is a full-length product of BCAN mRNA that arises from an incomplete or reduced glycosylation of the core protein. $B/b_{Ag}$ is absent from the normal adult brain but is found in high-grade glioma samples (Viapiano et al., 2005).

BCAN has been described as selectively overexpressed in a type of glioblastoma-derived stem-like tumor cell (Gunther et al., 2008). This subtype of stem-like cells showed highest pluripotency and tumorigenicity in vivo.

Chitinase 3-Like 1 (Cartilage Glycoprotein-39) (CHI3L1)

CHI3L1, a member of the "mammalian chitinase-like proteins" is expressed and secreted by several types of solid tumors. It is produced by cancer cells and tumor-associated macrophages, exhibits growth factor activity for cells involved in tissue remodeling processes and might play a role in cancer cell proliferation, differentiation, survival, invasiveness, metastasis, in angiogenesis and the inflammation and remodeling of the extracellular matrix surrounding the tumor (Johansen et al., 2006; Johansen et al., 2007; Ringsholt et al., 2007). Besides, CHI3L1 is a candidate autoantigen in rheumatoid arthritis. CD4 T cell lines from healthy donors directed against CHI3L1 expressed CD25, glucocorticoid-induced tumor necrosis factor receptor, and Foxp3 molecules and were capable of suppressing antigen-specific T cell responses. Responses in 50% of patients with rheumatoid arthritis exhibit polarization toward a proinflammatory T helper 1 phenotype and are significantly less powerful in suppressing antigen-specific recall responses (van Bilsen et al., 2004).

CHI3L1 is up-regulated by oncostatin M which is known to be induced in the nervous system as a result of cell stress, is expressed in most human brain tumors and activates the JAK/STAT signaling pathway (Krona et al., 2007). CHI3L1 expression was also associated with the expression of p-MAPK, p-mTOR and p-p70S6K in glioblastoma (Pelloski et al., 2006).

In several gene expression studies, CHI3L1 was shown to be more highly expressed in glioblastoma compared to normal brain with a range of 3- to 62-fold elevation over normal brain (Saidi et al., 2007; Kroes et al., 2007; Shostak et al., 2003; Tanwar et al., 2002). Immunohistochemical studies revealed that all cells with a functioning nucleus are capable of expressing CHI3L1 in their cytoplasm but the intensity of CHI3L1-expression was dependent on cellular activity. Thus cells known for exerting a high metabolic activity tended to show the most intense cytoplasmic staining (Ringsholt et al., 2007). Furthermore it could be shown by immunohistochemistry that glioblastoma show strikingly more CHI3L1 expression than anaplastic oligodendrogliomas (Nutt et al., 2005). Western blot analysis of glioma samples for CHI3L1 protein levels revealed substantial elevation in 65% of GBMs and undetectable levels in lower-grade gliomas (grade II and III) or normal brain tissue (Tanwar et al., 2002) In comparison to pilocytic astrocytoma, which does not spread and can be cured by surgery, only glioblastoma expresses CHI3L1 (Colin et al., 2006).

Serum levels of CHI3L1 are elevated in a variety of malignancies and have been associated with worse survival. Highest serum levels of CHI3L1 were found in patients with metastatic cancer with the shortest recurrence-free interval and shortest overall survival. Specifically in serum from glioblastoma patients CHI3L1 expression was elevated (Kim et al., 2007; Johansen et al., 2007; Johansen et al., 2006; Junker et al., 2005; Tanwar et al., 2002). GBM patients with active tumor have a significantly higher level of CHI3L1 than patients with no radiographic evidence of disease. Furthermore there is a significant inverse association between CHI3L1 and survival in GBM (Hormigo et al., 2006; Pelloski et al., 2005).

In addition, elevated CHI3L1-expression can be observed in breast cancer, where it correlates with larger tumor size, poorer tumor differentiation and a worse disease-free survival (Kim et al., 2007; Coskun et al., 2007). Moreover, in squamous cell carcinoma of the head and neck elevated CHI3L1 serum levels were detected in 53%. Patients with high serum CHI3L1 have shorter survival than patients with normal serum CHI3L1 (33 vs. 84 months) (Roslind et al., 2008).

Patients suffering from prostate cancer showed significantly higher serum levels of CHI3L1 in comparison to patients with BPH or healthy persons (Kucur et al., 2008).

CAP-GLY Domain Containing Linker Protein 2 (CLIP2)

The protein encoded by CLIP2 belongs to the family of cytoplasmic linker proteins, which have been proposed to mediate the interaction between specific membranous organelles and microtubules. CLIP2 was found to associate with both microtubules and an organelle called the dendritic lamellar body (general information from the NCBI-web page).

CLIP2 localizes to the ends of tyrosinated microtubules but not to the ends of detyrosinated microtubules. Tubulin-tyrosine ligase (TTL), the enzyme that catalyzes the addition of a C-terminal tyrosine residue to alpha-tubulin in the tubulin tyrosination cycle, is involved in tumor progression and has a vital role in neuronal organization (Peris et al., 2006). One study of genomic DNA from frozen sections of 30 cases of primary glioblastomas by GenoSensor Array 300 characterized gene amplifications, gene deletions, and chromosomal information in the whole genome. Genes that were frequently amplified included=CLIP2 (63.3%), EGFR (53.3%), IL6 (53.3%), ABCB1 (MDR1) (36.7%), and PDG-FRA (26.7%) (Suzuki et al., 2004).

Solute Carrier Organic Anion Transporter Family, Member 1C1 (SLCO1C1)

SLCO1C1 is selectively expressed at the blood-brain barrier (Chu et al., 2008). SLCO1C1 has selective substrate preference and may play an important role in the disposition of thyroid hormones in brain and testis (Pizzagalli et al., 2002). SLCO1C1 was not specifically detectable by immunofluorescence. SLCO1A2 and SLCO2B1 were detectable by immunofluorescence microscopy in the luminal membrane of endothelial cells forming the blood-brain barrier and the blood-tumor barrier, but not in the glioma cells (Bronger et al., 2005).

Dystrobrevin, Alpha (DTNA)

Alpha-dystrobrevin has been described primarily as a cytoplasmic component of the dystrophin-glycoprotein complex in skeletal muscle cells. Isoforms of DTNA show different localization in cells and tissues; at basolateral membranes in epithelial cells, dystrobrevins mediate contact with the extracellular matrix, peripheral and transmembrane proteins and the filamentous actin cytoskeleton. Beside their structural role, DTNAs are assumed to be important in cell signalling and cell differentiation and are associated with the tight junctions during their reorganization (Sjo et al., 2005). DTNA may be involved in the formation and stability of synapses as well as the clustering of nicotinic acetylcholine receptors.

Epidermal Growth Factor Receptor (Erythroblastic Leukemia Viral (v-erb-b) Oncogene Homolog, Avian) (EGFR)

A recent area of interest is the epidermal growth factor receptor (EGFR), since its abnormalities are one of the most common molecular aberrations in glioblastoma. Especially EGFRvIII (epidermal growth factor receptor variant III) is an oncogenic, constitutively active mutant form of the EGFR that is commonly expressed in glioblastoma (Zawrocki and Biernat, 2005). EGFR is involved in the activation of a number of pathways that regulate the phenotype of progenitor cells. Activated EGFR tyrosine kinase activity enhances neural stem cell migration, proliferation and survival. As EGFR signaling is also known to play a role in glioblastoma, it can be concluded that glioblastoma derives from a cancer stem cell and that EGFR signals are commonly altered in these precursor cells (Yuso-Sacido et al., 2006).

Primary glioblastomas arise de novo in older patients and often overexpress EGFR. EGFR overexpression correlates with increased angiogenesis, edema and invasion (Aghi et al., 2005). Furthermore, EGFR-amplified glioblastomas are radiation resistant (Barker et al., 2001) and recur more rapidly after treatment (Schlegel et al., 1994).

GBM is the only nonepithelial human tumor for which excessive activation of EGFR has been linked to tumor growth and patient survival, and EGFR activation promotes GBM infiltration in vitro (Penar et al., 1997).

EGFR is the proto-oncogene of erbB. Overexpression of EGFR can augment cell growth because of increased formation of active ligand:receptor complexes. Gene amplification is the mechanism underlying overexpression of EGF receptors in GBM tumors (Thompson and Gill, 1985). The EGFR gene on chromosome 7 is known to gain in copy number frequently in high-grade gliomas (Okada et al., 2007). Depletion of EGFR by short interference RNA abolishes the tumorigenesis of glioblastoma cells (Huang et al., 2007).

EGFR overexpression is detected in 40-70% of GBM whereas pilocytic, low-grade or anaplastic astrocytoma are invariably EGFR negative. (Agosti et al., 1992; Schwechheimer et al., 1995; Eppenberger and Mueller, 1994; Huncharek and Kupelnick, 2000; Liu et al., 2006a). High serum levels of EGFR indicate reduced survival (Quaranta et al., 2007). Furthermore, it was shown that long-term survivors with high grade astrocytomas are EGFRvIII negative (Liang et al., 2008).

Notch-1 up-regulates EGFR expression and correlations between levels of EGFR and Notch-1 mRNA can be found in primary high-grade human gliomas (Purow et al., 2008). EGFR itself is involved in constitutive activation of c-Jun NH2-terminal kinase (JNK), which contributes to proliferation, survival and tumorigenesis in some tumors, including gliomas (Li et al., 2008a).

Although EGFRvIII is only expressed by a small percentage of glioma cells, most of the cells exhibit a transformed phenotype. It was shown that EGFRvIII expression in indolent glioma cells stimulates formation of lipid-raft related microvesicles containing EGFRvIII which are released to cellular surroundings and can merge with the plasma membranes of cancer cells lacking EGFRvIII leading to the transfer of oncogenic activity (Al-Nedawi et al., 2008).

Fatty Acid Binding Protein 7, Brain (FABP7)

Fatty acid-binding proteins (FABPs) are cytosolic 14-15 kDa proteins, which are supposed to be involved in fatty acid (FA) uptake, transport, and targeting. They may modulate FA concentration and in this way influence function of enzymes, membranes, ion channels and receptors, and gene expression and cellular growth and differentiation. Nine FABP types can be discerned with a specific tissue distribution. In spite of 30-70% amino acid sequence identity, they have a similar tertiary, beta-clam structure in which the FA is bound. Nervous tissue contains four FABP types with a distinct spatio-temporal distribution (Veerkamp and Zimmerman, 2001). FABP7 is highly expressed in the developing brain and retina and its expression decreases significantly in the adult CNS (Godbout et al., 1998). Based on in vitro results, it has been suggested that FABP7 is required for the establishment of the radial glial system of the developing brain (Mita et al., 2007). In normal brain FABP7 protein is barely detectable but shows moderate to strong nuclear and cytoplasmic expression in several GBMs. FABP7-transfected cells display 5-fold greater migration than control cells. Thus, the shorter overall survival associated with FABP7 overexpression especially in glioblastoma may be due to increased migration and invasion of tumor cells into the surrounding brain parenchyma (Liang et al., 2005). Nuclear translocation of FABP7 is specifically related to EGFR amplification and more invasive tumors (Kaloshi et al., 2007). Thus, nuclear FABP7 may be induced by EGFR activation to promote migration of GBM tumor cells (Liang et al., 2006).

FABP7 expression has also been shown to be a marker for renal cell carcinoma. FABP7-expression can be detected only in carcinoma tissues but not in noncancerous parts of kidney samples (Teratani et al., 2007). The expression of FABP7 in renal cell carcinoma was shown to be 20-fold higher in the tumor in comparison to normal kidney tissue (Domoto et al., 2007; Buchner et al., 2007). It was also shown that FABP7 is frequently expressed in melanoma where it may be involved in cell proliferation and invasion (Goto et al., 2006).

Glial Fibrillary Acidic Protein (GFAP)

GFAP encodes one of the major intermediate filament proteins of mature astrocytes. It is used as a marker to distinguish astrocytes from other glial cells during development. Mutations in this gene cause Alexander disease, a rare disorder of astrocytes in the central nervous system. An additional transcript variant has been described, but its full length sequence has not been determined. Increased levels have been reported in autistic brains whereas brains from people with severe depression showed decreased GFAP.

Brains from primates that developed de novo tumors ten years after whole brain radiation were analyzed. Tumor precursors demonstrated cellular atypia and mitoses, and were negative for tumor-associated markers GFAP, EGFR and p53 (Lubensky et al., 2006).

In astrocytic neoplasms the number of GFAP positive cells and the intensity of the stain were directly proportional to the degree of malignancy. All the 3 cases of oligodendroglioma showed a negative reaction to GFAP (Reyaz et al., 2005). Pure oligodendrogliomas are immunohistologically negative for GFAP (Mokhtari et al., 2005). GFAP serum levels in patients with high grade glioma demonstrated a linear correlation to tumour volume (Brommeland et al., 2007). Even among GB patients a significant correlation between tumour volume, tumour necrosis volume, the amount of necrotic GFAP positive cells and serum GFAP level can be detected (Jung et al., 2007).

Following treatment of glioblastoma cell lines with the histone deacetylase inhibitor 4-phenylbutyrate, increased concentrations of non-phosphorylated GFAP were seen, while phosphorylated isoforms remained intact (Asklund et al., 2004).

In a glioblastoma cell line treated with TGF-alpha, GFAP gene transcription, mRNA level, and specific protein synthesis decreased by approximately 50% (Zhou and Skalli, 2000).

Technically, the GFAP promoter is frequently used as a tool in mouse models to induce the expression of desired proteins specifically in the nervous system.

Pancreatic islets of Langerhans are enveloped by peri-islet Schwann cells (pSC), which express GFAP. Autoimmune targeting of pancreatic nervous system tissue elements seems to be an integral, early part of natural type 1 diabetes (Winer et al., 2003). This pancreatic expression is not reflected by immatics or external gene expression data from bulk tissues. GFAP-001 has been published as an epitope against which type 1 diabetic patients as well as their non-diabetic relatives with antibody responses against diabetes autoantigens (increased risk for diabetes) showed enhanced reactivity of granzyme B-secreting CTLs (ex vivo ELISPOT) compared with healthy donors (Standifer et al., 2006).

Interestingly, an inverse correlation between the manifestation of autoimmune diseases, especially diabetes, and the risk of glioma development seems to exist (Aronson and Aronson, 1965; Schlehofer et al., 1999; Brenner et al., 2002; Schwartzbaum et al., 2003; Schwartzbaum et al., 2005).

G Protein-Coupled Receptor 56 (GPR56)

GPR56 is an atypical G protein-coupled receptor (GPCR) with an unusually large N-terminal extracellular region, which contains a long Ser/Thr-rich region forming a mucin-like stalk and due to this feature, GPR56 is thought to play a role in cell-cell, or cell-matrix interactions. Together with the high level of mRNA expression and its wide distribution, a possible role for this receptor in cell-cell interaction processes has been suggested (Liu et al., 1999). GPR56 belongs to the GPCR of the secretin family which has a role in the development of neural progenitor cells and has been linked to developmental malformations of the human brain. Higher GPR56 expression is correlated with the cellular transformation phenotypes of several cancer tissues compared with their normal counterparts, implying a potential oncogenic function. RNA interference-mediated GPR56 silencing results in apoptosis induction and reduced anchorage-independent growth of cancer cells via increased anoikis. GPR56 silencing also reduces cell adhesion to the extracellular matrix (Ke et al., 2007). Upregulation of GPR56 has been demonstrated in glioblastoma multiforme using functional genomics. Immunohistochemistry studies confirmed the expression of GPR56 in a majority of glioblastoma/astrocytoma tumor samples with undetectable levels of expression in normal adult brain (Shashidhar et al., 2005). In pancreatic cancer cells, GPR56 mRNA is expressed at high levels whereas GPR56 protein is either negligible or undetectable in these cells suggesting that the expression of GPR56 protein is suppressed in human pancreatic cancer cells (Huang et al., 2008). Earlier studies concerning metastasis showed that GPR56 is markedly down-regulated in highly metastatic variants from a human melanoma cell line implying that overexpression of GPR56 suppresses tumor growth and metastasis. This growth suppression is thought to be mediated by interaction of GPR56 with tissue transglutaminase (TG2), a widespread component of tissue and stroma, which has been implicated in suppression of tumor progression itself (Xu et al., 2006; Xu and Hynes, 2007). Another inhibitory impact of GPR56 has been reported for the migration of neural progenitor cells (NPCs). GPR56 is highly expressed in NPCs and probably participates in the regulation of NPC movement through the Galpha(12/13) and Rho signaling pathway, suggesting that GPR56 plays an important role in the development of the central nervous system (Iguchi et al., 2008).

Glutamate Receptor, Ionotropic, AMPA 4 (GRIA4)

α-amino-3-hydroxy-5-methyl-4-isoxazolepropionate (AMPA)-type glutamate receptors (AMPARs) mediate fast neurotransmission in excitatory synapses in the CNS and are composed of subunits taken from a set of four proteins, GluR1 through GluR4 (GRIA4).

GRIA4 subunits are ubiquitously expressed in human glioblastoma cells, operating as $Ca^{2+}$-permeable AMPARs. Conversion to $Ca^{2+}$-impermeable receptors inhibits cell locomotion and induces apoptosis whereas overexpression of $Ca^{2+}$-permeable AMPA receptors facilitates migration and proliferation of the tumor cells. Therefore $Ca^{2+}$-permeable AMPA receptors seem to have crucial roles in growth of glioblastoma (Ishiuchi et al., 2002).

Insulin-like growth factor 2 mRNA binding protein 3 (IGF2BP3) IGF2BP3 is a member of the insulin-like growth factor-II mRNA-binding protein family, implicated in mRNA localization, turnover and translational control. The encoded protein contains several KH domains, which are important in RNA binding and are known to be involved in RNA synthesis and metabolism. It is expressed mainly during embryonic development and in some tumors. Thus, IGF2BP3 is considered to be an oncofetal protein (Liao et al., 2005). Specific information about IGF2BP3 expression in glioblastoma was not found, but IGF2BP3 is described to be overexpressed in several other malignancies. Thus, IGF2BP3 is expressed in 30% of 716 analyzed clear cell renal cell carcinoma specimen. In this study, its expression was associated with advanced stage and grade of primary tumors as well as other adverse features including coagulative tumor necrosis and sarcomatoid differentiation. Furthermore, positive IGF2BP3 expression was associated with a 5-10 fold increased risk of distant metastases and with a 42%-50% increase in the risk of death from RCC, suggesting that IGF2BP3 expression represents an independent predictor of aggressive clear cell renal cell carcinoma tumor behavior (Hoffmann et al., 2008; Jiang et al., 2006; Jiang et al., 2008). IGF2BP3 expression was also detectable in malignant melanoma in comparison to benign nevi, where no expression was to be determined, even when dysplastic features are present (Pryor et al., 2008). In endometrial cancer, expression of IGF2BP3 is closely associated with type II endometrial cancer and an aggressive histologic phenotype among endometrial neoplastic lesions (Zheng et al., 2008). In 20 patients suffering from esophageal squamous cell carcinoma, induction of specific T-cell responses in TILs, regional lymph node lymphocytes and peripheral blood lymphocytes against a HLA-A2402-restricted epitope peptide from IGF2BP3 could be observed in 40% of all cases (Mizukami et al., 2008). IGF2BP3 is also highly expressed in pancreatic carcinomas. In 2 studies >90% of pancreatic tumor tissue samples showed IGF2BP3 expression after immunostaining whereas non-neoplastic pancreatic tissues were negative for IGF2BP3. Furthermore, IGF2BP3 mRNA was overexpressed in pancreatic carcinomas in comparison to non-neoplastic tissue samples and the expression increased progressively with tumor stage (Yantiss et al., 2005; Yantiss et al., 2008). IGF2BP3 expression was also found to be significantly increased in high-grade urothelial tumors while it is generally not expressed in benign urothelium or low-grade urothelial tumors. Moreover, patients with IGF2BP3-positive tumors have a much lower progression-free survival and disease-free survival rate than those with IGF2BP3-negative tumors. IGF2BP3-positive patients with superficial invasive urothelial carcinoma at initial diagnosis also went on to develop metastases, whereas no metastasis was found in IGF2BP3-negative patients. In addition, data from these studies suggested that IGF2BP3 may be involved in the progression of urothelial tumors from low grade to high grade in both papillary and flat lesions (Li et al., 2008b; Sitnikova et al., 2008).

Megalencephalic leukoencephalopathy with subcortical cysts 1 (MLC1) Megalencephalic leukoencephalopathy with subcortical cysts (MLC) is an autosomal recessive cerebral white matter disorder in children. MLC is caused by mutations in the gene MLC1 (Ilja Boor et al., 2006). According to the understanding of the inventors, no reports about any association of MLC1 with brain tumors are found in the literature.

One paper investigated the cellular and regional distribution of MLC1 in mouse brain (Schmitt et al., 2003). Highest MLC1 expression was found during the pre- and perinatal period in multipotential neural precursor cells. In the adult mouse brain MLC1 mRNA was exclusively detected in glial cells. In contrast to developing and mature astrocytes, oligodendrocytes were devoid of MLC1 expression.

Nestin (NES)

During development, there is extensive expression of the intermediate filament nestin in neuroepithelial cells in the ventricular layer at 11 weeks post-conceptional age in all parts of the CNS, whereas nestin immunoreactivity diminishes during the second and third trimesters (Takano and Becker, 1997; Lendahl et al., 1990; Zimmerman et al., 1994; Tohyama et al., 1992). During or after migration away from the proliferative ventricular layer, nestin expression is sharply downregulated in post-mitotic neurons (Arnold and Trojanowski, 1996). Nestin-staining of non-neoplastic adult human brain tissue showed only weak staining of a very small number of endothelial cells (Dahlstrand et al., 1992). Nestin can be re-expressed during neoplastic transformation (Veselska et al., 2006). In glioma tissues, nestin immunoreactivity occurs only in tumor cells and the quantity of nestin produced increases as the grade of glioma becomes more malignant toward glioblastoma. Glioblastomas (malignancy grade IV) express the highest incidence of nestin-positive cells and in general the highest levels of nestin staining. Nestin expression can be detected in tumor cells of various types of primary CNS tumors, which are of neuroectodermal origin, but not in metastasizing carcinoma cells (Dahlstrand et al., 1992; Tohyama et al., 1992). Nestin is almost not expressed in diffuse astrocytomas, variably expressed in anaplastic astrocytomas and strongly and irregularly expressed in glioblastomas, where its distribution varies in a complementary way with GFAP and Vimentin (Schiffer et al., 2006). Clinically, nestin-negative CNS germ cell tumors did not exhibit dissemination, while all tumors that exhibited dissemination also strongly expressed nestin protein (Sakurada et al., 2007).

Tumor cells strongly expressing nestin are often located close to blood vessels (Dahlstrand et al., 1992), (Kurihara et al., 2000; Sugawara et al., 2002; Florenes et al., 1994; Strojnik et al., 2007) and nestin expression by activated endothelium has been suggested as an angiogenesis marker (Teranishi et al., 2007; Maderna et al., 2007; Amoh et al., 2005; Mokry et al., 2004).

GBM comprises transformed precursors that bear the full complement of functional characteristics expected from stem cells, including the capacity for tumor generation. These cells can establish GBM even upon serial transplantation and can therefore be identified as tumor neural stem cells (Galli et al., 2004). These cells belong to the CD133+ cell subpopulation from human brain tumors and co-express the NSC marker nestin, but not differentiated neural lineage markers (Singh et al., 2004b; Singh et al., 2003; Singh et al., 2004a; Mao et al., 2007). The presence of a CD133+/nestin+ population in brain tumors suggests that a normal neural stem cell may be the cell of origin for gliomas (Shiras et al., 2007). As Notch signaling is active in brain tumor and stem cells, it has been shown that the nestin promoter is activated in culture through Notch activity (Shih and Holland, 2006).

Transfecting the rat astrocytoma C6 cell line with nestin siRNA duplex revealed an effective suppression influence of nestin siRNA on cell growth of cultured astrocytoma cells in a dose-dependent manner (Wei et al., 2008).

Nestin expression has also been reported for cancer stem cells in prostate (Gu et al., 2007; Gipp et al., 2007) and pancreatic cancer (Carriere et al., 2007) as well as melanoma (Klein et al., 2007). Furthermore, nestin is also expressed in the following tumors: GIST (Tsujimura et al., 2001; Sarlomo-Rikala et al., 2002), melanomas (Florenes et al., 1994; Brychtova et al., 2007), Colorectal cancer (Teranishi et al., 2007) and pancreatic tumors (Ohike et al., 2007; Kleeberger et al., 2007).

Nestin expression can also be found in various normal tissues: Nestin expression has been reported in podocytes of normal mature human kidney glomeruli. In normal conditions nestin is expressed in several glomerular cell types at early stages of development and becomes confined to podocytes in mature glomeruli (Ishizaki et al., 2006), indicating that nestin is critical for some aspect of podocyte function. Adult glomeruli display nestin immunoreactivity in vimentin-expressing cells with the podocyte morphology (Bertelli et al., 2007). Possibly nestin serves through an interaction with vimentin to bolster the mechanical strength of podocytes which experience high tensile stress during glomerular filtration (Perry et al., 2007). Thus, in human kidney, nestin is expressed from the first steps of glomerulogenesis within podocytes, mesangial, and endothelial cells. This expression is then restricted to podocytes in mature glomeruli and can not be detected in other structures of the adult human kidney (Su et al., 2007). Immunohistochemistry revealed constant nestin expression in the cortex of normal human adrenal glands. Nestin expressing cells are prevalently located in the zona reticularis whereas adrenal carcinomas display a variable number of nestin-immunoreactive cells (Toti et al., 2005).

Nestin expression is also reported from interstitial cells of Cajal (ICC) in the normal gastrointestinal tract. Thus most intramuscular ICC in antrum and all myenteric ICC in small intestine are nestin-immunoreactive as well as some myenteric ICC and most ICC in the circular musculature of the colon (Vanderwinden et al., 2002). In pancreas, nestin-immunoreactive cells can be found in islets and in the exocrine portion. In the area of big pancreatic ducts, nestin-positive cells represent small capillaries scattered in the connective tissue surrounding the duct epithelium. Thus, nestin is expressed by vascular endothelial cells in human pancreas (Klein et al., 2003). In the islets themselves islet progenitor cells that express nestin can be found. It is hypothesized that these nestin-positive islet-derived progenitor cells are a distinct population of cells that reside within pancreatic islets and may participate in the neogenesis of islet endocrine cells (Zulewski et al., 2001). In the adult normal liver a population of human liver stem cells that are positive for vimentin and nestin can be isolated (Herrera et al., 2006). In cell culture assays, analysis of cytoskeleton and matrix composition by immunostaining revealed that fetal lung- and adult marrow-derived cells express vimentin and nestin proteins in intermediate filaments (Sabatini et al., 2005). In young permanent teeth, nestin is found in functional odontoblasts. Its expression is down-regulated and nestin is absent from older permanent teeth while it is up-regulated again in carious and injured teeth (About et al., 2000).

Nestin-expressing adult stem cells can also be found in the perilumenal region of the mature anterior pituitary and, using genetic inducible fate mapping, it was demonstrated that they serve to generate subsets of all six terminally differentiated endocrine cell types of the pituitary gland.

These stem cells, while not playing a significant role in organogenesis, undergo postnatal expansion and start producing differentiated progeny, which colonize the organ that initially entirely consisted of differentiated cells derived from embryonic precursors (Gleiberman et al., 2008).

Nuclear Receptor Subfamily 2, Group E, Member 1 (NR2E1)

NR2E1 (TLX) is a transcription factor that is essential for neural stem cell proliferation and self-renewal by recruiting histone deacetylases (HDACs) to its downstream target genes to repress their transcription, which in turn regulates neural stem cell proliferation. Recruitment of HDACs leads to transcriptional repression of TLX target genes, the cyclin-dependent kinase inhibitor, p21(CIP1/WAF1)(p21), and the tumor suppressor gene, PTEN (Sun et al., 2007). The TLX/HOX11 subfamily of divergent homeobox genes are involved in various aspects of embryogenesis and, in the case of TLX1/HOX11 and TLX3/HOX11L2, feature prominently as oncogenes in human T-cell acute lymphoblastic leukemia (Dixon et al., 2007). NR2E1 underlies a fundamental developmental program of retinal organization and controls the generation of the proper numbers of retinal progenies and development of glial cells during the protracted period of retinogenesis (Miyawaki et al., 2004). No glioblastoma specific information found.

Neuronal Cell Adhesion Molecule (NRCAM)

Human NRCAM (Neuroglia related Cell Adhesion Molecule) is over expressed in glioblastoma multiforme tissue (GMT) as compared to normal brain tissue (NBT). NRCAM is described as single-pass type I transmembrane protein interacting with ankyrin. Antisense hNRCAM caused reduction in the native hNRCAM expression, changes in cell morphology, reduced cell proliferation rate and lengthening of the cell cycle. Furthermore, antisense hNRCAM overexpression in these cells caused extensive reduction in the number of soft agar colonies and invasion through extra cellular matrix (ECM) gel in vitro. Subcutaneous injection of antisense hNRCAM overexpressing glioblastoma cells into nude mice caused complete inhibition of tumor formation as compared to vector only transfected cells. Intratumoral inoculation of antisense hNRCAM expressing plasmid also caused slow tumor growth in nude mice in vivo (Sehgal et al., 1999). Gene-specific RT-PCR analysis indicated that hNRCAM is over-expressed in high-grade astrocytomas, gliomas and glioblastoma tumor tissues as compared to normal brain tissue (Sehgal et al., 1998). NRCAM, a cell-cell adhesion molecule of the immunoglobulin-like cell adhesion molecule family, known for its function in neuronal outgrowth and guidance, was recently identified as a target gene of beta-catenin signaling in human melanoma and colon carcinoma cells and tissue. Retrovirally mediated transduction of NRCAM into fibroblasts induces cell motility and tumorigenesis (Conacci-Sorrell et al., 2005). Induction of NRCAM transcription by beta-catenin or plakoglobin plays a role in melanoma and colon cancer tumorigenesis, probably by promoting cell growth and motility (Conacci-Sorrell et al., 2002). Also other targets in beta-catenin signalling are upregulated—such as MYC (Liu et al., 2008). NrCAM is overexpressed in human papillary thyroid carcinomas at the mRNA and protein levels, whatever the tumor stage (Gorka et al., 2007).

Overexpression of NRCAM mRNA in tumors is associated with high proliferation indices and was associated with a poor outcome in ependymomas (Zangen et al., 2007).

Podoplanin (PDPN)

PDPN is a mucin-like type-I integral membrane glycoprotein with diverse distribution in human tissues. It is involved in cancer cell migration, invasion, metastasis and malignant progression and is involved in platelet aggregation. CLEC-2 is the first identified pathophysiological receptor of podoplanin (Kato et al., 2008). 115 glioblastomas were investigated using immunohistochemistry with an anti-PDPN antibody. 47% of glioblastomas expressed PDPN on surface cells, especially around necrotic areas and proliferating endothelial cells. Furthermore, PDPN mRNA and protein expression were markedly higher in glioblastoma than in anaplastic astrocytomas suggesting that PDPN expression might be associated with malignancy of astrocytic (Mishima et al., 2006). PDPN was also shown to be expressed in 82.9% of glioblastomas (29/35) in another analyses (Shibahara et al., 2006). In a study investigating PDPN expression and platelet-aggregating activites of glioblastoma cell lines, LN319 highly expressed PDPN and induced platelet aggregation. NZ-1, a highly reactive anti-PDPN antibody, neutralized platelet aggregation by LN319 suggesting that PDPN is a main reason for platelet aggregation induced by (Kato et al., 2006). PDPN gene expression levels were significantly higher in glioblastomas than in non-neoplastic white matter, which was confirmed by immunohistochemistry (Scrideli et al., 2008). PDPN is specifically expressed by lymphatic but not blood vascular endothelial cells in culture and in tumor-associated lymphangiogenesis. Although PDPN was primarily absent from normal human epidermis, its expression was strongly induced in 22 of 28 squamous cell carcinomas suggesting a role for PDPN in tumor progression (Schacht et al., 2005). PDPN is upregulated in the invasive front of a number of human carcinomas. Investigation of PDPN expression in cultured human breast cancer cells, in a mouse model of pancreatic beta cell carcinogenesis, and in human cancer biopsies indicated that PDPN promotes tumor cell invasion in vitro and in vivo. PDPN induces collective cell migration by filopodia formation via the downregulation of the activities of small Rho family GTPases. In conclusion, PDPN induces an alternative pathway of tumor cell invasion in the absence of epithelial-mesenchymal transition (Wicki et al., 2006) PDPN expression level was enhanced in most colorectal tumor patients (Kato et al., 2003) TGF-beta is supposed to be a physiological regulator of PDPN in tumor cells (Suzuki et al., 2008) PDPN is expressed by cancer cells derived from esophagus, lung, liver, colon and breast as well as lymphatic endothelial cells (Kono et al., 2007).

Tenascin C (Hexabrachion) (TNC)

The expression of the extracellular matrix glycoprotein TNC in glioblastoma but not in normal brain and its association with glioblastoma-proliferative endothelium basement membranes suggested already in 1983 that TNC may be a useful marker of gliomas (Bourdon et al., 1983). During tumor progression, the ECM of tumor tissues is remodeled and now provides an environment that is more conductive for tumor progression, of which angiogenesis is a crucial step (Carnemolla et al., 1999). TNC is overexpressed in tumor vessels that have a high proliferative index which indicates that TNC is involved in neoplastic angiogenesis (Kim et al., 2000). In tumors, TNC-expression can be induced by hypoxia (Lal et al., 2001). TNC induction is mediated by TGF-beta1, providing a mechanism for the invasion of high-grade gliomas into healthy parenchyma (Hau et al., 2006). Also, TNC overexpression is a consequence of the specific activation of the tenascin-C gene promoter by gastrin, which is known to significantly modulate the migration of human glioblastoma cells (Kucharczak et al., 2001). TNC down-regulates tropomyosin-1 and thus destabilizes actin stress fibers. It additionally causes downregulation of the Wnt inhibitor Dickkopf1. As reduced tropomyosin-1 expression and increased Wnt signaling are closely linked to transformation and tumorigenesis, TNC specifically modulates these signaling pathways to enhance proliferation of glioma cells (Ruiz et al., 2004).

Perivascular staining of TNC around tumor-supplying blood vessels is observed in glioblastoma tissues, whereas in WHOII and III gliomas, perivascular TNC staining is less frequent, indicating that the intensity of TNC staining correlates with the tumor grade and the strongest staining indicates poor prognosis (Herold-Mende et al., 2002; Zukiel et al., 2006). Highest TNC-expression is observed in connective tissue surrounding tumors (Chiquet-Ehrismann and Tucker, 2004). TNC also contributes to the generation of a stem cell niche within the subventricular zone (SVZ), acting to orchestrate growth factor signaling to accelerate neural stem cell development. TNC is essential for the timely expression of the EGFR in neural stem cells and enhances FGF2 signalling. The predominant effect of TNC on cells in the SVZ is the regulation of developmental progression (Garcion et al., 2004). TNC is the strongest inducer of directed human NSC migration (haptotaxis). The tumor-produced ECM thus provides a permissive environment for NSC tropism to disseminated tumor cells (Ziu et al., 2006).

The TNC pathway also plays an important role in mammary tumor growth and metastases. Thus, signaling blockade or knockdown of TNC in MDA-MB-435 cells resulted in a significant impairment of cell migration and anchorage-independent cell proliferation. Mice injected with clonal MDA-MB-435 cells with reduced expression of TNC demonstrated a significant decrease in primary tumor growth as well as a decrease in tumor relapse after surgical removal of the primary tumor and a decrease in the incidence of lung metastasis (Calvo et al., 2008).

Survivin (BIRC5)

Expression of BIRC5 (survivin), a member of the inhibitor of apoptosis protein (IAP) family, is elevated in fetal tissues and in various human cancers, with greatly reduced expression in adult normal differentiated tissues, particularly if their proliferation index is low. Survivin seems to be capable of regulating both cellular proliferation and apoptotic cell death. Although survivin is usually located in the cell cytoplasmic region and associated with poor prognosis in cancer, nuclear localization, indicative of favorable prognosis, has also been reported (O'Driscoll et al., 2003). Regulation of and through survivin has been described by several mechanisms. Survivin seems to be associated with the molecular chaperone Hsp60. In vivo, Hsp60 is abundantly expressed in primary human tumors as compared with matched normal tissues. Acute ablation of Hsp60 by small interfering RNA destabilizes the mitochondrial pool of survivin, induces mitochondrial dysfunction, and activates caspase-dependent apoptosis (Ghosh et al., 2008). Furthermore, Ras inhibition results in release of the survivin "brake" on apoptosis and in activation of the mitochondrial apoptotic pathway. Especially in glioblastoma, resistance to apoptosis can be abolished by a Ras inhibitor that targets survivin (Blum et al., 2006). There also seems to be a correlation between NF-kappaB hyperactivity in gliomas and hyperexpression of survivin, one of NF-kappaB target genes. Thus, NF-kappaB-activated anti-apoptotic genes are hyperexpressed in tumor samples. Especially in glioblastoma, very high levels of survivin expression are detectable (Angileri et al., 2008). It is suggested that survivin overexpression in brain gliomas might play an important role in malignant proliferation, anti-apoptosis and angiogenesis (Zhen et al., 2005; Liu et al., 2006b). Several analyses were performed to study survivin expression and its impact on survival in glioblastoma. To summarize, survivin expression, especially the simultaneous expression in nucleus and cytoplasm in astrocytic tumors was significantly associated with malignancy grade (with highest survivin expression in glioblastoma) and shorter overall survival times compared with patients who had survivin-negative tumors (Kajiwara et al., 2003; Saito et al., 2007; Uematsu et al., 2005; Mellai et al., 2008; Grunda et al., 2006; Xie et al., 2006; Sasaki et al., 2002; Chakravarti et al., 2002).

Survivin-overexpression has also been described for other tumor entities. In breast cancer, survivin expression is associated with higher grade and shorter disease-free survival (Yamashita et al., 2007; Al-Joudi et al., 2007; Span et al., 2004). In esophageal cancer cell lines, the promoter activity of survivin was shown to be 28.5 fold higher than in normal tissues (Sato et al., 2006). In colorectal cancer, survivin expression is also associated with pathological grade and lymph node metastasis (Tan et al., 2005). The aggressiveness of clear cell renal cell carcinoma was shown to be associated with survivin expression. Furthermore, expression of survivin is inversely associated with cancer-specific survival (Kosari et al., 2005). Survivin expression can be detected in a panel of keratinocytic neoplasms and hyperproliferative skin lesions but not in normal skin (Bowen et al., 2004). In pancreatic cancer cell lines, survivin was amplified in 58% of the tested cell lines (Mahlamaki et al., 2002). In squamous cell carcinoma, survivin expression can help to identify cases with more aggressive and invasive clinical phenotype (Lo et al., 2001).

As survivin is such a promising target for cancer therapy, studies using survivin-derived peptides showed that survivin is immunogenic in tumor patients by eliciting CD8+ T cell-mediated responses. In addition, survivin specifically stimulated CD4+ T-cell reactivity in peripheral blood lymphocytes from the same patients (Casati et al., 2003; Piesche et al., 2007).

Survivin (SVN, BIR0) is overexpressed in a multitude of cancer entities. Thus, in general, overexpression of survivin is thought to be associated with shorter overall-survival and higher malignancy grades.

The present invention further relates to particular marker proteins that can be used in the prognosis of glioblastoma. Further, the present invention further relates to the use of these novel targets for cancer treatment.

As provided herein, the proteins GFAP, FABP7, DTNA, NR2E1, SLCO1C1, CHI3L1, ACSBG1, IGF2BP3, NLGN4X, MLC1, NRCAM, BCAN, EGFR, PDPN, NES, and CLIP2 are highly over-expressed in glioblastomas compared with normal brain and other vital tissues (e.g. liver kidney, heart). The proteins GRP56, CSPG4, NRCAM, TNC, BIRC5, CLIP2, NES, PDPN, EGFR, BCAN, and GRIA4 are shown to have an important role in tumorigenesis as they are in involved in malignant transformation, cell growth, proliferation, angiogenesis or invasion into normal tissue.

The proteins NES, TNC, BIRC5, EGFR are associated with cancer stem cells or stem cell niches in glioblastoma. Cancer stem cells are a tumor cell subpopulation with self-renewing potential required for sustained tumor growth. These cells reside in specialized and highly organized structures, so called cancer stem cell niches that are required for the maintenance of the self-renewing potential of cancer stem cells. Overexpression of the proteins BIRC5, NRCAM, IGF2BP3 in tumors has been shown to be associated with advanced disease stages and poor prognosis for the patients.

BCA, CLIP2, DTNA, NLGNAX, NR2E1, NRCAM and PDPN, are shown to play an important role in tissue remodeling required for tumor growth in the nervous system. Therefore, the expression of BCA, CLIP2, DTNA, NLGNAX, NR2E1, NRCAM and PDPN can be used as a marker to distinguish glioblastoma from other forms of cancer.

Thus, the present invention provides methods of identifying an animal, preferably a human that is likely to have glioblastoma. In one embodiment the likelihood determined is from 80% to 100%. One such method comprises determining the level of at least one of the proteins BCA, CLIP2, DTNA, NLGNAX, NR2E1, NRCAM and PDPN in a tumor sample from the animal subject. In one embodiment, the sample is obtained by radical surgery. In another embodiment, the sample is obtained by needle biopsy.

When the level of BCA, CLIP2, DTNA, NLGNAX, NR2E1, NRCAM or PDPN as determined is 20% or more up-regulated in cells relative to that determined in benign epithelial cells of the same specimen, the animal subject is identified as being likely to have glioblastoma.

The more different proteins of the group comprising BCA, CLIP2, DTNA, NLGNAX, NR2E1, NRCAM, and PDPN are up-regulated the higher the possibility of the animal subject is identified as being likely to have glioblastoma.

In one embodiment, the determination of the level of BCA, CLIP2, DTNA, NLGNAX, NR2E1, NRCAM or PDPN is performed in situ. In another embodiment, the determination of the level of BCA, CLIP2, DTNA, NLGNAX, NR2E1, NRCAM or PDPN is performed in vitro. In still another embodiment, the determination of the level of BCA, CLIP2, DTNA, NLGNAX, NR2E1, NRCAM or PDPN is performed in vivo. In a preferred embodiment, the determination of the level of BCA, CLIP2, DTNA, NLGNAX, NR2E1, NRCAM or PDPN is performed by Laser Capture Microscopy coupled with a Western blot.

In a particular embodiment, the determination of the level of BCA, CLIP2, DTNA, NLGNAX, NR2E1, NRCAM or PDPN is performed with an antibody specific for BCA, CLIP2, DTNA, NLGNAX, NR2E1, NRCAM or PDPN. In another embodiment, the determination of the level of BCA, CLIP2, DTNA, NLGNAX, NR2E1, NRCAM or PDPN is performed by PCR with a primer specific for an mRNA encoding BCA, CLIP2, DTNA, NLGNAX, NR2E1, NRCAM or PDPN. In still another embodiment, the determination of the level of BCA, CLIP2, DTNA, NLGNAX, NR2E1, NRCAM or PDPN is performed with a nucleotide probe specific for an mRNA encoding BCA, CLIP2, DTNA, NLGNAX, NR2E1, NRCAM or PDPN. In one embodiment, the determination of the level of BCA, CLIP2, DTNA, NLGNAX, NR2E1, NRCAM or PDPN is performed using a Northern blot. In another embodiment, the determination of the level of BCA, CLIP2, DTNA, NLGNAX, NR2E1, NRCAM or PDPN is achieved using a ribonuclease protection assay. In other embodiments, immunological tests such as enzyme-linked immunosorbent assays (ELISA), radioimmunoassays (RIA), and Western blots may be used to detect BCA, CLIP2, DTNA, NLGNAX, NR2E1, NRCAM, and PDPN polypeptides in a body fluid sample (such as blood, serum, sputum, urine, or peritoneal fluid). Biopsies, tissue samples, and cell samples (such as ovaries, lymph nodes, ovarian surface epithelial cell scrapings, lung biopsies, liver biopsies, and any fluid sample containing cells (such as peritoneal fluid, sputum, and pleural effusions) may be tested by disaggregating and/or solubilizing the tissue or cell sample and subjecting it to an immunoassay for polypeptide detection, such as ELISA, RIA, or Western blotting. Such cell or tissue samples may also be analyzed by nucleic acid-based methods, e.g., reverse transcription-polymerase chain reaction (RT-PCR) amplification, Northern hybridization, or slot- or dot-blotting. To visualize the distribution of tumor cells within a tissue sample, diagnostic tests that preserve the tissue structure of a sample, e.g., immunohistological staining, in situ RNA hybridization, or in situ RT-PCR may be employed to detect glioblastoma marker polypeptide or mRNA, respectively. For in vivo localization of tumor masses, imaging tests such as magnetic resonance imaging (MRI) may be employed by introducing into the subject an antibody that specifically binds a BCA, CLIP2, DTNA, NLGNAX, NR2E1, NRCAM or PDPN polypeptide (particularly a cell surface-localized polypeptide), wherein the antibody is conjugated or otherwise coupled to a paramagnetic tracer (or other appropriate detectable moiety, depending upon the imaging method used); alternatively, localization of an unlabeled tumor marker-specific antibody may be detected using a secondary antibody coupled to a detectable moiety.

In addition, the present invention further provides chimeric/fusion proteins/peptides comprising the BCA, CLIP2, DTNA, NLGNAX, NR2E1, NRCAM and/or PDPN polypeptides, and fragments thereof, including functional, proteolytic and antigenic fragments.

The fusion partner or sections of a hybrid molecule suitably provide epitopes that stimulate CD4$^+$ T-cells. CD4$^+$ stimulating epitopes are well known in the art and include those identified in tetanus toxoid. In a further preferred embodiment the peptide is a fusion protein, in particular comprising N-terminal amino acids of the HLA-DR antigen-associated invariant chain (Ii). In one embodiment the peptide of the invention is a truncated human protein or a fusion protein of a protein fragment and another polypeptide portion provided that the human portion includes one or more inventive amino acid sequences.

Antibodies to the BCA, CLIP2, DTNA, NLGNAX, NR2E1, NRCAM or PDPN polypeptides, to the chimeric/fusion proteins comprising the BCA, CLIP2, DTNA, NLGNAX, NR2E1, NRCAM or PDPN polypeptides, as well as to the fragments of the BCA, CLIP2, DTNA, NLGNAX, NR2E1, NRCAM or PDPN polypeptides, including proteolytic, and antigenic fragments, and to the chimeric/fusion proteins/peptides comprising these fragments are also part of the present invention. In addition, methods of using such antibodies for the prognosis of cancer, and glioblastoma in particular, are also part of the present invention.

The antibodies of the present invention can be polyclonal antibodies, monoclonal antibodies and/or chimeric antibodies. Immortal cell lines that produce a monoclonal antibody of the present invention are also part of the present invention.

One of ordinary skill in the art will understand that in some instances, higher expression of BCA, CLIP2, DTNA, NLGNAX, NR2E1, NRCAM or PDPN as a tumor marker gene will indicate a worse prognosis for a subject having glioblastoma. For example, relatively higher levels BCA, CLIP2, DTNA, NLGNAX, NR2E1, NRCAM or PDPN expression may indicate a relative large primary tumor, a higher tumor burden (e.g., more metastases), or a relatively more malignant tumor phenotype.

The more the overexpression of the different proteins of the group comprising BCA, CLIP2, DTNA, NLGNAX, NR2E1, NRCAM and PDPN is different, the worse is the prognosis for a patient.

The diagnostic and prognostic methods of the invention involve using known methods, e.g., antibody-based methods to detect BCA, CLIP2, DTNA, NLGNAX, NR2E1, NRCAM and PDPN polypeptides and nucleic acid hybridization- and/or amplification-based methods to detect BCA, CLIP2, DTNA, NLGNAX, NR2E1, NRCAM and/or PDPN mRNA.

In addition, since rapid tumor cell destruction often results in autoantibody generation, the glioblastoma tumor markers of the invention may be used in serological assays (e.g., an ELISA test of a subject's serum) to detect autoantibodies against BCA, CLIP2, DTNA, NLGNAX, NR2E1, NRCAM or PDPN in a subject. BCA, CLIP2, DTNA, NLGNAX, NR2E1, NRCAM and PDPN polypeptide-specific autoantibody levels that are at least about 3-fold higher (and preferably at least 5-fold or 7-fold higher, most preferably at least 10-fold or 20-fold higher) than in a control sample are indicative of glioblastoma.

Cell-surface localized, intracellular, and secreted BCA, CLIP2, DTNA, NLGNAX, NR2E1, NRCAM and PDPN polypeptides may all be employed for analysis of biopsies, e.g., tissue or cell samples (including cells obtained from liquid samples such as peritoneal cavity fluid) to identify a tissue or cell biopsy as containing glioblastoma cells. A biopsy may be analyzed as an intact tissue or as a whole-cell sample, or the tissue or cell sample may be disaggregated and/or solubilized as necessary for the particular type of diagnostic test to be used. For example, biopsies or samples may be subjected to whole-tissue or whole-cell analysis of BCA, CLIP2, DTNA, NLGNAX, NR2E1, NRCAM and PDPN polypeptide or mRNA levels in situ, e.g., using immunohistochemistry, in situ mRNA hybridization, or in situ RT-PCR. The skilled artisan will know how to process tissues or cells for analysis of polypeptide or mRNA levels using immunological methods such as ELISA, immunoblotting, or equivalent methods, or analysis of mRNA levels by nucleic acid-based analytical methods such as RT-PCR, Northern hybridization, or slot- or dot-blotting.

Kits for Measuring Expression Levels of BCA, CLIP2, DTNA, NLGNAX, NR2E1, NRCAM and PDPN The present invention provides kits for detecting an increased expression level of BCA, CLIP2, DTNA, NLGNAX, NR2E1, NRCAM and PDPN as a glioblastoma marker gene in a subject. A kit for detecting glioblastoma marker polypeptide preferably contains an antibody that specifically binds a chosen glioblastoma marker polypeptide. A kit for detecting glioblastoma marker mRNA preferably contains one or more nucleic acids (e.g., one or more oligonucleotide primers or probes, DNA probes, RNA probes, or templates for generating RNA probes) that specifically hybridize with BCA, CLIP2, DTNA, NLGNAX, NR2E1, NRCAM and PDPN mRNA.

Particularly, the antibody-based kit can be used to detect the presence of, and/or measure the level of, a BCA, CLIP2, DTNA, NLGNAX, NR2E1, NRCAM and/or PDPN polypeptide that is specifically bound by the antibody or an immunoreactive fragment thereof. The kit can include an antibody reactive with the antigen and a reagent for detecting a reaction of the antibody with the antigen. Such a kit can be an ELISA kit and can contain a control (e.g., a specified amount of a particular glioblastoma marker polypeptide), primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

A nucleic acid-based kit can be used to detect and/or measure the expression level of BCA, CLIP2, DTNA, NLGNAX, NR2E1, NRCAM and PDPN by detecting and/or measuring the amount of BCA, CLIP2, DTNA, NLGNAX, NR2E1, NRCAM and PDPN mRNA in a sample, such as a tissue or cell biopsy. For example, an RT-PCR kit for detection of elevated expression of BCA, CLIP2, DTNA, NLGNAX, NR2E1, NRCAM and PDPN preferably contains oligonucleotide primers sufficient to perform reverse transcription of glioblastoma marker mRNA to cDNA and PCR amplification of glioblastoma marker cDNA, and will preferably also contain control PCR template molecules and primers to perform appropriate negative and positive controls, and internal controls for quantization. One of ordinary skill in the art will understand how to select the appropriate primers to perform the reverse transcription and PCR reactions, and the appropriate control reactions to be performed. Such guidance is found, for example, in F. Ausubel et al., Current Protocols in Molecular Biology, John Wiley & Sons, New York, N.Y., 1997. Numerous variations of RT-PCR are known in the art. Targeted Delivery of immunotoxins to BCA, CLIP2, DTNA, NLGNAX, NR2E1, NRCAM and PDPN can be employed as therapeutic targets for the treatment or prevention of glioblastoma. For example, an antibody molecule that specifically binds a cell surface-localized BCA, CLIP2, DTNA, NLGNAX, NR2E1, NRCAM and PDPN polypeptide can be conjugated to a radioisotope or other toxic compound. Antibody conjugates are administered to the subject so that the binding of the antibody to its cognate glioblastoma polypeptide results in the targeted delivery of the therapeutic compound to glioblastoma cells, thereby treating an ovarian cancer.

The therapeutic moiety can be a toxin, radioisotope, drug, chemical, or a protein (see, e.g., Bera et al. "Pharmacokinetics and antitumor activity of a bivalent disulfide-stabilized Fv immunotoxin with improved antigen binding to erbB2" Cancer Res. 59:4018-4022 (1999)). For example, the antibody can be linked or conjugated to a bacterial toxin (e.g., diptheria toxin, pseudomonas exotoxin A, cholera toxin) or plant toxin (e.g., ricin toxin) for targeted delivery of the toxin to a cell expressing BCA, CLIP2, DTNA, NLGNAX, NR2E1, NRCAM and PDPN. This immunotoxin can be delivered to a cell and upon binding the cell surface-localized glioblastoma marker polypeptide, the toxin conjugated to the glioblastoma marker-specific antibody will be delivered to the cell.

Yet another aspect of the present invention relates to an antibody that specifically binds to a human major histocompatibility complex (MHC) class I or II being complexed with a HLA-restricted antigen (in the following also designate as "complex-specific antibody"). Yet another aspect of the present invention then relates to a method of producing said antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, Denkberg G, Lev A, Epel M, Reiter Y. Recombinant antibodies with MHC-restricted, peptide-specific, T-cell receptor-like specificity: new tools to study antigen presentation and TCR-peptide-MHC interactions. J Mol Recognit. 2003 Septmber-October; 16(5):324-32; Denkberg G, Lev A, Eisenbach L, Benhar I, Reiter Y. Selective targeting of melanoma and APCs using a recombinant antibody with TCR-like specificity directed toward a melanoma differentiation antigen. J Immunol. 2003 Sep. 1; 171(5):2197-207; and Cohen C J, Sarig O, Yamano Y, Tomaru U, Jacobson S, Reiter Y. Direct phenotypic analysis of human MHC class I antigen presentation: visualization, quantitation, and in situ detection of human viral epitopes using peptide-specific, MHC-restricted human recombinant antibodies. J Immunol. 2003 Apr. 15; 170(8): 4349-61, which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

The term "antibody" is used herein in a broad sense and includes both polyclonal and monoclonal antibodies. In addition to intact immunoglobulin molecules, also included in the term "antibodies" are fragments or polymers of those immunoglobulin molecules and humanized versions of immunoglobulin molecules, so long as they exhibit any of the desired properties (e.g., being a complex-specific antibody as above, delivery of a toxin to a cancer cell expressing an cancer preferred a glioblastoma marker gene at an increased level, and/or inhibiting the activity of an cancer marker polypeptide, such as survivin) described herein.

In addition, for any BCA, CLIP2, DTNA, NLGNAX, NR2E1, NRCAM and PDPN polypeptide for which there is a specific ligand (e.g., a ligand that binds a cell surface-localized protein), the ligand can be used in place of an antibody to target a toxic compound to a glioblastoma cell, as described above.

Whenever possible, the antibodies of the invention may be purchased from commercial sources. The antibodies of the invention may also be generated using well-known methods. The skilled artisan will understand that either full length glioblastoma marker polypeptides or fragments thereof may be used to generate the antibodies of the invention. A polypeptide to be used for generating an antibody of the invention may be partially or fully purified from a natural source, or may be produced using recombinant DNA techniques. For example, a cDNA encoding a BCA, CLIP2, DTNA, NLGNAX, NR2E1, NRCAM or PDPN polypeptide, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the glioblastoma marker polypeptide used to generate the antibody.

One of skill in the art will know that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistiy, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988). For example, the antibodies may be tested in ELISA assays, Western blots, immunohistochemical staining of formalin-fixed glioblastomas or frozen tissue sections. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, published 22 Dec. 1994, and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The antibody fragments, whether attached to other sequences or not, can also include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Antibodies in Human Diagnosis and Therapy, Haber et al, eds. Raven Press, New York (1977) pp. 365-389. A typical daily dosage of the antibody used alone might range from about 1 (μg/kg to up to 100 mg/kg of body weight or more per day, depending on the factors mentioned above. Following administration of an antibody for treating glioblastoma, the efficacy of the therapeutic antibody can be assessed in various ways well known to the skilled practitioner. For instance, the size, number, and/or distribution of glioblastoma in a subject receiving treatment may be monitored using standard tumor imaging techniques. A therapeutically-administered antibody that arrests tumor growth, results in tumor shrinkage, and/or prevents the development of new tumors, compared to the disease course that would occurs in the absence of antibody administration, is an efficacious antibody for treatment of glioblastoma.

Because the glioblastoma tumor marker BCA, CLIP2, DTNA, NLGNAX, NR2E1, NRCAM and PDPN of the invention are highly expressed in glioblastoma cells and is expressed at extremely low levels in normal cells, inhibition of BCA, CLIP2, DTNA, NLGNAX, NR2E1, NRCAM or PDPN expression or polypeptide activity may be integrated into any therapeutic strategy for treating or preventing glioblastoma.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of glioblastoma marker function by antisense gene therapy may be accomplished by direct administration of antisense glioblastoma marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of antisense tumor marker RNA to cells can be carried out by any of the methods for direct nucleic acid administration described below.

An alternative strategy for inhibiting BCA, CLIP2, DTNA, NLGNAX, NR2E1, NRCAM and/or PDPN function using gene therapy involves intracellular expression of an anti-BCA, CLIP2, DTNA, NLGNAX, NR2E1, NRCAM or PDPN antibody or a portion of an anti-BCA, CLIP2, DTNA, NLGNAX, NR2E1, NRCAM or PDPN antibody. For example, the gene (or gene fragment) encoding a monoclonal antibody that specifically binds to a BCA, CLIP2, DTNA, NLGNAX, NR2E1, NRCAM or PDPN polypeptide and inhibits its biological activity is placed under the transcriptional control of a specific (e.g., tissue- or tumor-specific) gene regulatory sequence, within a nucleic acid expression vector. The vector is then administered to the subject such that it is taken up by glioblastoma cells or other cells, which then secrete the anti-BCA, CLIP2, DTNA, NLGNAX, NR2E1, NRCAM or PDPN antibody and thereby block biological activity of the BCA, CLIP2, DTNA, NLGNAX, NR2E1, NRCAM and PDPN polypeptide. Preferably, the BCA, CLIP2, DTNA, NLGNAX, NR2E1, NRCAM and PDPN polypeptides are present at the extracellular surface of glioblastoma cells.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of glioblastoma marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system that can package a recombinant retroviral genome. The recombinant retrovirus can then be used to infect and thereby deliver to the infected cells antisense nucleic acid that inhibits expression of BCA, CLIP2, DTNA, NLGNAX, NR2E1, NRCAM or PDPN. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more BCA, CLIP2, DTNA, NLGNAX, NR2E1, NRCAM and PDPN targets and the affinity value (Kd) is less than 1×10 µM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the BCA, CLIP2, DTNA, NLGNAX, NR2E1, NRCAM and PDPN proteins express in situ or in vitro.

The present invention in another preferred aspect thereof provides a peptide comprising a sequence that is selected from the group of SEQ ID NO:1 to SEQ ID NO:30 or a variant thereof which is 85% homologous to SEQ ID NO:1 to SEQ ID NO:30 or a variant thereof that will induce T cells cross-reacting with said peptide.

In a preferred embodiment the peptide is selected from a group of the peptides comprising a sequence that is selected from the group of SEQ ID NO:1 to SEQ ID NO:24 or a variant thereof which is 85% homologous to SEQ ID NO:1 to SEQ ID NO:24 or a variant thereof that will induce T cells cross-reacting with said peptide.

The peptides of the invention have the ability to bind to a molecule of the human major histocompatibility complex (MHC) class-I or -II.

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared herein may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994). Commonly available sequence analysis software, more specifically, Vector NTI, GENETYX or analysis tools provided by public databases.

A person skilled in the art will be able to assess, whether T cells induced by a variant of a specific peptide will be able to cross-react with the peptide itself (Fong et al., 2001); (Zaremba et al., 1997; Colombetti et al., 2006; Appay et al., 2006).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in SEQ ID NO:1 to 30. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL. These CTL can subsequently cross-react with cells and kill cells that express a polypeptide which contains the natural amino acid sequence of the cognate peptide as defined in the aspects of the invention. As can be derived from the scientific literature (Rammensee et al., 1997) and databases (Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID NO:1 to 30, by maintaining the known anchor residues, and would be able to determine whether such variants maintain the ability to bind MHC class I or II molecules. The variants of the present invention retain the ability to bind to the TCR of activated CTL, which can subsequently cross-react with- and kill cells that express a polypeptide containing the natural amino acid sequence of the cognate peptide as defined in the aspects of the invention.

Those amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

TABLE 2

Variants and motif of the peptides according to SEQ ID NO: 1 to 25

| | | | Position | | | | | | | | |
|---|---|---|---|---|---|---|---|---|---|---|---|
| | | | 1 | 2 | 3 | 4 | 5 | 6 | 7 | 8 | 9 |
| CSP-001 SEQ ID NO: 25 | Pep-tide Code Variants | | T | M | L | A | R | L | A | S | A |
| | | | | | L | | | | | | L |
| | | | | | | | E | | | | K |
| | | | I | | A | G | I | I | A | E | |
| | | | L | | Y | P | K | | Y | | |
| | | | F | | F | T | Y | T | H | | |
| | | | K | | P | | N | | | | |
| | | | M | | M | | F | | | | |
| | | | Y | | S | | V | | | | |
| | | | V | | R | | | | | | |

TABLE 2-continued

Variants and motif of the peptides according to SEQ ID NO: 1 to 25

| | | | Position | | | | | | | | |
|---|---|---|---|---|---|---|---|---|---|---|---|
| | | | 1 | 2 | 3 | 4 | 5 | 6 | 7 | 8 | 9 |
| ACS-001 SEQ ID NO: 3 | Pep-tide Code Variants | | K | I | M | E | R | I | Q | E | V |
| | | | | | M | | | | | | L |
| | | | | | L | | | | | | L |
| | | | | | | | | | | | K |
| | | | I | | A | G | I | | A | | |
| | | | L | | Y | P | K | | L | Y | |
| | | | F | | F | T | Y | | T | H | |
| | | | | | P | | N | | | | |
| | | | M | | | | F | | | | |
| | | | Y | | S | | V | | | | |
| | | | V | | R | | | | | | |
| BCA-001 SEQ ID NO: 4 | Pep-tide Code Variants | | F | L | G | D | P | P | E | K | L |
| | | | | | M | | | | | | |
| | | | | | | | E | | | | |
| | | | I | | A | G | I | I | A | E | |
| | | | L | | Y | P | K | | L | Y | |
| | | | | | F | T | Y | | T | H | |
| | | | K | | P | | N | | | | |
| | | | M | | M | | F | | | | |
| | | | Y | | S | | V | | | | |
| | | | V | | R | | | | | | |
| BCA-002 SEQ ID NO: 5 | Pep-tide Code Variants | | A | L | W | A | W | P | S | E | L |
| | | | | | M | | | | | | |
| | | | | | | | E | | | | K |
| | | | I | | A | G | I | I | A | | |
| | | | L | | Y | P | K | | L | Y | |
| | | | F | | F | T | | Y | T | H | |
| | | | K | | P | | N | | | | |
| | | | M | | M | | F | | | | |
| | | | Y | | S | | V | | | | |
| | | | V | | R | | | | | | |
| CHI3L1-010 SEQ ID NO: 6 | Pep-tide Code Variants | | T | L | Y | G | M | L | N | T | L |
| | | | | | M | | | | | | |
| | | | | | | | E | | | | K |
| | | | I | | A | | I | I | A | E | |
| | | | L | | | P | K | | Y | | |
| | | | F | | F | T | Y | | T | H | |
| | | | K | | P | | N | | | | |
| | | | M | | M | | F | | | | |
| | | | Y | | S | | V | | | | |
| | | | V | | R | | | | | | |
| CLIP2-001 SEQ ID NO: 7 | Pep-tide Code Variants | | S | L | N | E | L | R | V | L | L |
| | | | | | M | | | | | | |
| | | | | | | | | | | | K |
| | | | I | | A | G | I | I | A | E | |
| | | | L | | Y | P | K | | L | Y | |
| | | | F | | F | T | Y | | T | H | |
| | | | K | | P | | N | | | | |
| | | | M | | M | | F | | | | |
| | | | Y | | S | | V | | | | |
| | | | V | | R | | | | | | |
| SLCO1C1-001 SEQ ID NO: 2 | Pep-tide Code Variants | | Y | L | I | A | G | I | I | S | L |
| | | | | | M | | | | | | |
| | | | | | | | E | | | | K |
| | | | I | | A | G | I | | A | E | |
| | | | L | | Y | P | K | | L | Y | |
| | | | F | | F | T | Y | | T | H | |
| | | | K | | P | | N | | | | |
| | | | M | | M | | F | | | | |
| | | | | | S | | V | | | | |
| | | | V | | R | | | | | | |

TABLE 2-continued

Variants and motif of the peptides according to SEQ ID NO: 1 to 25

| | | Position | | | | | | | | |
|---|---|---|---|---|---|---|---|---|---|---|
| | | 1 | 2 | 3 | 4 | 5 | 6 | 7 | 8 | 9 |
| DTNA-001 SEQ ID NO: 8 | Peptide Code Variants | K | L M | Q | D | E | A | Y | Q | V L L |
| | | | | | E | | | | K | |
| | | I | A | G | I | | I | A | E | |
| | | L | Y | P | K | | L | | | |
| | | F | F | T | Y | | T | H | | |
| | | | | P | | | N | | | |
| | | | M | M | F | | | | | |
| | | Y | S | V | | | | | | |
| | | V | R | | | | | | | |
| EGFR-007 SEQ ID NO: 9 | Peptide Code Variants | A | L M | A | V | L | S | N | Y | D L L |
| | | | | | E | | | | K | |
| | | I | A | G | I | | I | A | E | |
| | | L | Y | P | K | | L | Y | | |
| | | F | F | T | Y | | T | H | | |
| | | K | | P | | | N | | | |
| | | M | M | | F | | | | | |
| | | Y | S | | | | | | | |
| | | V | R | | | | | | | |
| FABP7-001 SEQ ID NO: 10 | Peptide Code Variants | L | T M L | F | G | D | V | V | A | V L L |
| | | | | | E | | | | K | |
| | | I | A | | I | | I | A | E | |
| | | | Y | | P | K | | L | Y | |
| | | F | | | T | Y | | T | H | |
| | | K | | | P | | | N | | |
| | | M | M | | | F | | | | |
| | | Y | S | | | V | | | | |
| | | V | R | | | | | | | |
| GFAP-001 SEQ ID NO: 11 | Peptide Code Variants | N | L M | A | Q | D | L | A | T | V L L |
| | | | | | E | | | | K | |
| | | I | G | | | | | | E | |
| | | L | Y | | P | K | | Y | | |
| | | F | F | | T | Y | | T | H | |
| | | K | | | P | | | N | | |
| | | M | M | | | F | | | | |
| | | Y | S | | | | | | | |
| | | V | R | | | V | | | | |
| GPR56-002 SEQ ID NO: 12 | Peptide Code Variants | F | L M | L | S | E | P | V | A | L |
| | | | | | E | | | | K | |
| | | I | A | G | I | | I | A | E | |
| | | L | Y | P | K | | L | Y | | |
| | | | F | T | Y | | T | H | | |
| | | K | P | | N | | | | | |
| | | M | M | | F | | | | | |
| | | Y | S | | V | | | | | |
| | | V | R | | | | | | | |
| GRI-001 SEQ ID NO: 13 | Peptide Code Variants | N | I M L | L | E | Q | I | V | S | V L L |
| | | | | | E | | | | K | |
| | | I | A | G | I | | I | A | E | |
| | | L | Y | P | K | | L | Y | | |
| | | F | F | T | Y | | T | H | | |
| | | K | | P | | | N | | | |
| | | M | M | | F | | | | | |
| | | Y | S | | V | | | | | |
| | | V | R | | | | | | | |
| IGF2BP3-001 SEQ ID NO: 14 | Peptide Code Variants | K | I M L | Q | E | I | L | T | Q | V L L |
| | | | | | | | | | K | |
| | | I | A | G | | | I | A | E | |
| | | L | Y | P | K | | | Y | | |
| | | F | F | T | Y | | T | H | | |
| | | | | P | | | N | | | |
| | | M | M | | F | | | | | |
| | | Y | S | | V | | | | | |
| | | V | R | | | | | | | |
| MLC-001 SEQ ID NO: 15 | Peptide Code Variants | S | V M L | V | E | V | I | A | G | I L L |
| | | | | | | | | | K | |
| | | I | A | G | I | | | | E | |
| | | L | Y | P | K | | L | Y | | |
| | | F | F | T | Y | | T | H | | |
| | | K | | P | | | N | | | |
| | | M | M | | F | | | | | |
| | | Y | S | | | | | | | |
| | | V | R | | | | | | | |
| NES-001 SEQ ID NO: 16 | Peptide Code Variants | G | L M | Q | S | Q | I | A | Q | V L L |
| | | | | | E | | | | K | |
| | | I | A | G | I | | | | E | |
| | | L | Y | P | K | | L | Y | | |
| | | F | F | T | Y | | T | H | | |
| | | K | | P | | | N | | | |
| | | M | M | | F | | | | | |
| | | Y | S | | V | | | | | |
| | | V | R | | | | | | | |
| NES-002 SEQ ID NO: 17 | Peptide Code Variants | S | L M | Q | E | N | L | E | S | L |
| | | | | | | | | | K | |
| | | I | A | G | I | | I | A | E | |
| | | L | Y | P | K | | | Y | | |
| | | F | F | T | Y | | T | H | | |
| | | K | | P | | | | | | |
| | | M | M | | F | | | | | |
| | | Y | S | | V | | | | | |
| | | V | R | | | | | | | |
| NES-003 SEQ ID NO: 18 | Peptide Code Variants | F | L M | F | P | G | T | E | N | Q L |
| | | | | | E | | | | K | |
| | | I | A | G | I | | I | A | E | |
| | | L | Y | | K | | L | Y | | |
| | | | | T | Y | | | H | | |
| | | K | | P | | | N | | | |
| | | M | M | | F | | | | | |
| | | Y | S | | V | | | | | |
| | | V | R | | | | | | | |
| NES-004 SEQ ID NO: 19 | Peptide Code Variants | N | L M | A | E | E | L | E | G | V L L |
| | | | | | | | | | K | |
| | | I | | G | I | | I | A | E | |
| | | L | Y | P | K | | | Y | | |
| | | F | F | T | Y | | T | H | | |
| | | K | | P | | | N | | | |
| | | M | M | | F | | | | | |
| | | Y | S | | V | | | | | |
| | | V | R | | | | | | | |

TABLE 2-continued

Variants and motif of the peptides according to SEQ ID NO: 1 to 25

| | | Position | | | | | | | | |
|---|---|---|---|---|---|---|---|---|---|---|
| | | 1 | 2 | 3 | 4 | 5 | 6 | 7 | 8 | 9 |
| NLGN4X-001 SEQ ID NO: 1 | Peptide Code Variants | N | L M | D | T | L | M | T | Y | V L L K E |
| | | I L F K M Y V | A Y F P M S R | G P | I K Y N F V | I L T | A Y H | E |
| NR2E1-001 SEQ ID NO: 20 | Peptide Code Variants | K | I M L | I | S | E | I Q A L L L K E |
| | | I L F M Y V | A Y F P M S R | G P T P M S R | I K Y N F V | A L T | E Y H |
| NRCAM-001 SEQ ID NO: 21 | Peptide Code Variants | G | L M | W | H | H | Q T E V L L K E |
| | | I L F K M Y V | A Y F P M S R | G P T | I K Y N F V | I L T | A Y H | E |
| PDPN-001 SEQ ID NO: 22 | Peptide Code Variants | T | L M | V | G | I | I V G V L L K E |
| | | I L F K M Y V | A Y F P M S R | P T P M S R | K Y N F V | A L T | E Y H |
| TNC-001 SEQ ID NO: 23 | Peptide Code Variants | A | M L | T | Q | L | L A G V L L K E |
| | | I L F K M Y V | A Y F P M S R | G P T | I K Y N F V | I L T | E Y H | |
| TNC-002 SEQ ID NO: 24 | Peptide Code Variants | Q | L M | L | A | G | V F L A L L K E |
| | | I L F K M Y V | A Y F P M S R | G P T | I K Y N F V | I L T | A Y H | E |

It is furthermore known for MHC-class II-presented peptides that these peptides are composed of a "core sequence" having an amino acid sequence fitting to a certain HLA-allele-specific motif and, optionally, N- and/or C-terminal extensions that do not interfere with the function of the core sequence (i.e. are deemed as irrelevant for the interaction of the peptide and all or a subset of T cell clones recognizing the natural counterpart). The N- and/or C-terminal extensions can, for example, be between 1 to 10 amino acids in length, respectively. These peptides can be used either directly in order to load MHC class II molecules or the sequence can be cloned into the vectors according to the description herein below. As these peptides constitute the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1,000 residues, preferably fewer than 500 residues, more preferably fewer than 100, more preferably fewer than 100 and most preferably between 30 and 8 residues. Accordingly, the present invention also provides peptides and variants thereof wherein said peptide or variant has an overall length of between 8 and 100, preferably between 8 and 30, and most preferred between 8 and 16, namely 8, 9, 10, 11, 12, 13, 14, 15, 16 amino acids.

Longer peptides may also be suitable, 9-mer or 10-mer peptides as described in the above Table 2 are preferred for MHC class I-peptides, while 12- to 15-mers are preferred for MHC class II peptides.

For MHC class II restricted peptides, several different peptides with the same core sequence may be presented in the MHC molecule. As the interaction with the recognizing T (helper) cell is defined by a core sequence of 9 to 11 amino acids, several length variants may be recognized by the same T (helper) cell clone. Thus, several different lengths variants of a core binding sequence may be used for direct loading of MHC class II molecules without the nee for further processing and trimming at the N- or C-terminal ends. Correspondingly, naturally occurring or artificial variants that induce T cells cross-reacting with a peptide of the invention are often length variants.

If a peptide that is longer than around 12 amino acid residues is used directly to bind to a MHC class II molecule, it is preferred that the residues that flank the core HLA binding region are residues that do not substantially affect the ability of the peptide to bind specifically to the binding groove of the MHC class II molecule or to present the peptide to the T (-helper) cell. However, as already indicated above, it will be appreciated that larger peptides may be used, e.g. when encoded by a polynucleotide, since these larger peptides may be fragmented by suitable antigen-presenting cells. However, in same cases it has been shown that the core sequence flanking regions can influence the peptide binding to MHC class II molecule or the interaction of the dimeric MHC:peptide complex with the TCR in both directions compared to a reference peptide with the same core sequence. Intramolecular tertiary structures within the peptide (e.g. loop formation) normally decrease the affinities to the MHC or TCR. Intermolecular interactions of the flanking regions with parts of the MHC or TCR beside the peptide binding grooves may stabilize the interaction. These changes in affinity can have a dramatic influence on the potential of a MHC class II peptide to induce T (helper) cell responses.

It is also possible that MHC class I epitopes, although usually between 8-10 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Preferred are therefore peptides with a core sequence selected from a group consisting of SEQ ID No 1 to SEQ ID No 30 with extensions of 1 to 10 amino acids on the C-terminal and/or the N-terminal, more preferred the overall number of these flanking amino acids is 1 to 12, more preferred 1 to 10, more preferred 1 to 8, more preferred 1 to 6, more preferred 1 to 4 and even more preferred 1 to 2, wherein the flanking amino acids can be distributed in any ratio to the C-terminus and the N-terminus (for example all flanking amino acids can be added to one terminus, or the amino acids can be added equally to both termini or in any other ratio), provided that the peptide is still able to bind to an HLA molecule in the same way as said peptide according to any of the SEQ ID No 1 to SEQ ID No 30.

The flanking amino acids can also reduce the speed of peptide degradation in vivo so that the amount of the actual peptide available to the CTLs is higher compared to the peptide without flanking amino acids, thus acting as a prodrug.

Accordingly, the present invention also provides peptides and variants of MHC class I epitopes wherein the peptide or variant has an overall length of between 8 and 100, preferably between 8 and 30, and most preferred between 8 and 16, namely 8, 9, 10, 11, 12, 13, 14, 15, 16 amino acids.

Of course, the peptide or variant according to the present invention will have the ability to bind to a molecule of the human major histocompatibility complex (MHC) class I or II. Binding of a peptide or a variant to a MHC complex may be tested by methods known in the art, for example those described in the literature for different MHC class II alleles (e.g. (Vogt et al., 1994; Malcherek et al., 1994; Manici et al., 1999; Hammer et al., 1995; Tompkins et al., 1993; Boyton et al., 1998)).

In a particularly preferred embodiment of the invention the peptide consists or consists essentially of an amino acid sequence according to SEQ ID NO: 1 to SEQ ID NO: 30.

"Consisting essentially of" shall mean that a peptide according to the present invention, in addition to the sequence according to any of SEQ ID No. 1 to SEQ ID No. 30 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein which comprises, for example, the 80 N-terminal amino acids of the HLA-DR antigen-associated invariant chain (p33, in the following "Ii") as derived from the NCBI, GenBank™ Accession-number X00497 (Strubin, M. et al 1984).

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —$CH_2$—NH, —$CH_2$S—, —$CH_2CH_2$—, —CH=CH—, —$COCH_2$—, —CH(OH)$CH_2$—, and —$CH_2$SO—. U.S. Pat. No. 4,897,445 provides a method for the solid phase synthesis of non-peptide bonds (—$CH_2$—NH) in polypeptide chains which involves polypeptides synthesized by standard procedures and the non-peptide bond synthesized by reacting an amino aldehyde and an amino acid in the presence of $NaCNBH_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulfonic acid (TNBS), amide modification of carboxyl groups and sulfhydryl modification by performic acid oxidation of cysteine to cysteic acid, formation of mercurial derivatives, formation of mixed disulfides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lu et al (1981) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, Bruckdorfer et al. 2004, and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitrile/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, CNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc, New Haven, Conn., USA.

A desirable method of modifying the DNA encoding the polypeptide of the invention employs the polymerase chain reaction as disclosed by (Saiki et al (1988)). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the beta-lactamase gene for ampicillin resistance selection in bacteria, hGH polyA, and the f1 origin. Vectors containing the preprotrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) are currently under investigation for the treatment of prostate cancer (Sipuleucel-T) (Small E J et al 2006; Rini et al 2006).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 μg, of peptide or DNA may be given and will depend on the respective peptide or DNA. Doses of this range were successfully used in previous trials (Brunsvig et al 2006; Staehler et al 2007).

Another aspect of the present invention includes an in vitro method for producing activated T cells, the method comprising contacting in vitro T cells with antigen loaded human class I or II MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

In the case of a MHC class II epitope being used as an antigen, the T cells are CD4-positive helper cells, preferably of $T_{H1}$-type. The MHC class II molecules may be expressed on the surface of any suitable cell. Preferably the cell does not naturally express MHC class II molecules (in which case the cell has been transfected in order to express such a molecule). Alternatively, if the cell naturally expresses MHC class II molecules, it is preferred that it is defective in the antigen-processing or antigen-presenting pathways. In this way, it is possible for the cell expressing the MHC class II molecule to be completely loaded with a chosen peptide antigen before activating the T cell.

The antigen-presenting cell (or stimulator cell) typically has MHC class II molecules on its surface and preferably is itself substantially incapable of loading said MHC class II molecule with the selected antigen. The MHC class II molecule may readily be loaded with the selected antigen in vitro.

Preferably, the mammalian cell lacks or has a reduced level or function of the TAP peptide transporter. Suitable cells that lack the TAP peptide transporter include T2, RMA-S and *Drosophila* cells. TAP is the Transporter associated with Antigen Processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Kane et al 1985.

Preferably, the host cell before transfection expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class II molecules and of the costimulator molecules are publicly available from the GenBank™ and EMBL databases.

Similarly, in case of a MHC class I epitope being used as an antigen, the T cells are CD8-positive CTLs.

If an antigen-presenting cell is transfected to express such an epitope, preferably the cell comprises an expression vector capable of expressing a peptide containing SEQ ID NO: 1 to SEQ ID NO: 30 or a variant amino acid sequence thereof.

A number of other methods may be used for generating CTL in vitro. For example, the methods described in Peoples et al (1995) and Kawakami et al (1992) use autologous tumor-infiltrating lymphocytes in the generation of CTL. Plebanski et al (1995) makes use of autologous peripheral blood lymphocytes (PLBs) in the preparation of CTL. Jochmus et al (1997) describes the production of autologous CTL by pulsing dendritic cells with peptide or polypeptide, or via infection with recombinant virus. Hill et al (1995) and Jerome et al (1993) make use of B cells in the production of autologous CTL. In addition, macrophages pulsed with peptide or polypeptide, or infected with recombinant virus, may be used in the preparation of autologous CTL. S. Walter et al. 2003 describe the in vitro priming of T cells by using artificial antigen presenting cells (aAPCs), which is also a suitable way for generating T cells against the peptide of choice. In this study, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC: peptide complexes, aAPCs should carry other proteins with co-stimulatory activity like anti-CD28 antibodies coupled to their surface. Furthermore such aAPC-based systems often require the addition of appropriate soluble factors, e. g. cytokines like interleukin-12.

Allogeneic cells may also be used in the preparation of T cells and a method is described in detail in WO 97/26328. For example, in addition to *Drosophila* cells and T2 cells, other cells may be used to present antigens such as CHO cells, baculovirus-infected insect cells, bacteria, yeast, vaccinia-infected target cells. In addition plant viruses may be used (see, for example, Porta et al (1994)) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to 30.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease which can be readily tested for, and detected.

In vivo, the target cells for the CD4-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art and can be found, e.g. in (Rosenberg et al., 1987; Rosenberg et al., 1988; Dudley et al., 2002; Yee et al., 2002; Dudley et al., 2005); reviewed in (Gattinoni et al., 2006) and (Morgan et al., 2006).

Any molecule of the invention, i.e. the peptide, nucleic acid, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al (1993)). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth in SEQ ID NO:1 or 20 and at least one additional peptide, preferably two to 50, more preferably two to 25, even more preferably two to 15 and most preferably two, three, four, five, six, seven, eight, nine, ten, eleven, twelve or thirteen peptides. The peptide(s) may be derived from one or more specific TAAs and may bind to MHC class I and/or class II molecules.

The polynucleotide may be substantially pure, or contained in a suitable vector or delivery system. The nucleic acid may be DNA, cDNA, PNA, CNA, RNA or a combination thereof. Methods for designing and introducing such a nucleic acid are well known in the art. An overview is provided by e.g. Pascolo S. 2006; Stan R. 2006, or A Mandavi 2006. Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T ($T_H$) cells to an antigen, and would thus be considered useful in the medicament of the present invention. Suitable adjuvants include, but are not limited to, 1018 ISS, aluminum salts, Amplivax, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA), resimiquimod, ImuFact IMP321, Interleukins as IL-2, IL-13, IL-21, Interferon-alpha or -beta, or pegylated derivatives thereof, IS Patch, ISS, ISCOMATRIX, ISCOMs, Juvlmmune, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, PLG and dextran microparticles, resiquimod, SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Dupuis M et al 1998; Allison 1998). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immuno-adjuvants (e.g., IL-12, IL-15, IL-23, IL-7, IFN-alpha. IFN-beta) (Gabrilovich et al 1996).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_H1$ cells and strong cytotoxic T-lymphocyte (CTL) generation, even in the absence of CD4 T cell help. The $T_H1$ bias induced by TLR9 stimulation is maintained even in the presence of vaccine adjuvants such as alum or incomplete Freund's adjuvant (IFA) that normally promote a $T_H2$ bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg et al 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and AmpliGen, non-CpG bacterial DNA or RNA as well as immunoactive small molecules and antibodies such as cyclophosphamide, sunitinib, Bevacizumab, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4 and SC58175, which may act therapeutically and/or as an adjuvant. The amounts and concentrations of adjuvants and additives useful in the context of the present invention can readily be determined by the skilled artisan without undue experimentation. Preferred adjuvants are dSLIM, Interferon-alpha,—beta, CpG7909, IC31, Imiquimod, resimiquimod, PeviTer, RNA, tadalafil, temozolomide, and JuvImmune.

Preferred adjuvants are dSLIM, BCG, OK432, imiquimod, resimiquimod, GMCSF, interferon-alpha, PeviTer and JuvImmune or combinations thereof.

In a preferred embodiment the pharmaceutical composition according to the invention the adjuvant is selected from the group consisting of colony-stimulating factors, such as Granulocyte Macrophage Colony Stimulating Factor (GM-CSF, sargramostim), imiquimod, resiquimod, and interferon-alpha.

In a still further preferred embodiment of the pharmaceutical composition according to the invention, the adjuvant is imiquimod or resimiquimod. In an even more preferred embodiment of the pharmaceutical composition according to the invention, the adjuvant is the combination of GM-CSF and imiquimod.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed. 2000, American Pharmaceutical Association and pharmaceutical press. The composition can be used for a prevention, prophylaxis and/or therapy of adenomatous or cancerous diseases.

The present invention provides a medicament that useful in treating cancer, in particular glioma and brain cancer, breast cancer, prostate cancer, esophagus cancer, colorectal cancer, renal cancer, pancreatic cancer, squamous cell carcinomas and keratinocytic neoplasms of the skin, leukemia, lung cancer, ovarian cancer, and melanoma.

The present invention includes a kit comprising:
(a) a container that contains a pharmaceutical composition as described above, in solution or in lyophilized form;
(b) optionally a second container containing a diluent or reconstituting solution for the lyophilized formulation; and
(c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 μg) and preferably not more than 3 mg/mL/peptide (=1500 μg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

Since the peptides of the invention derived from BCA, CLIP2, DTNA, NLGNAX, NR2E1, NRCAM and PDPN were isolated from glioblastoma, the medicament of the invention is preferably used to treat glioblastoma.

The present invention will now be described in the following examples and Figures that describe preferred embodiments thereof, nevertheless, without being limited thereto. For the purposes of the present invention, all references as cited herein are incorporated by reference in their entireties.

Figure 1B:
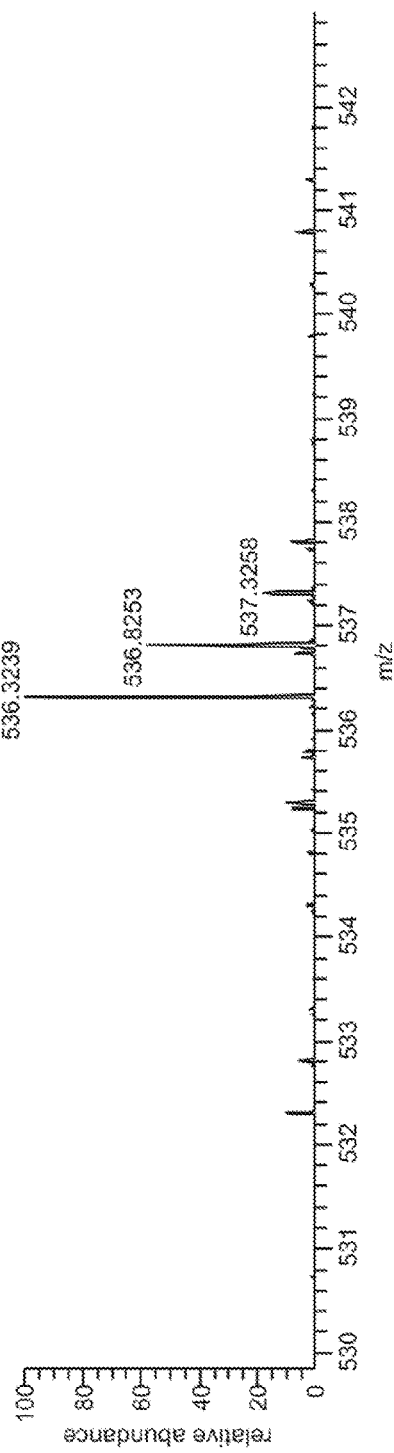
Figure 1C:
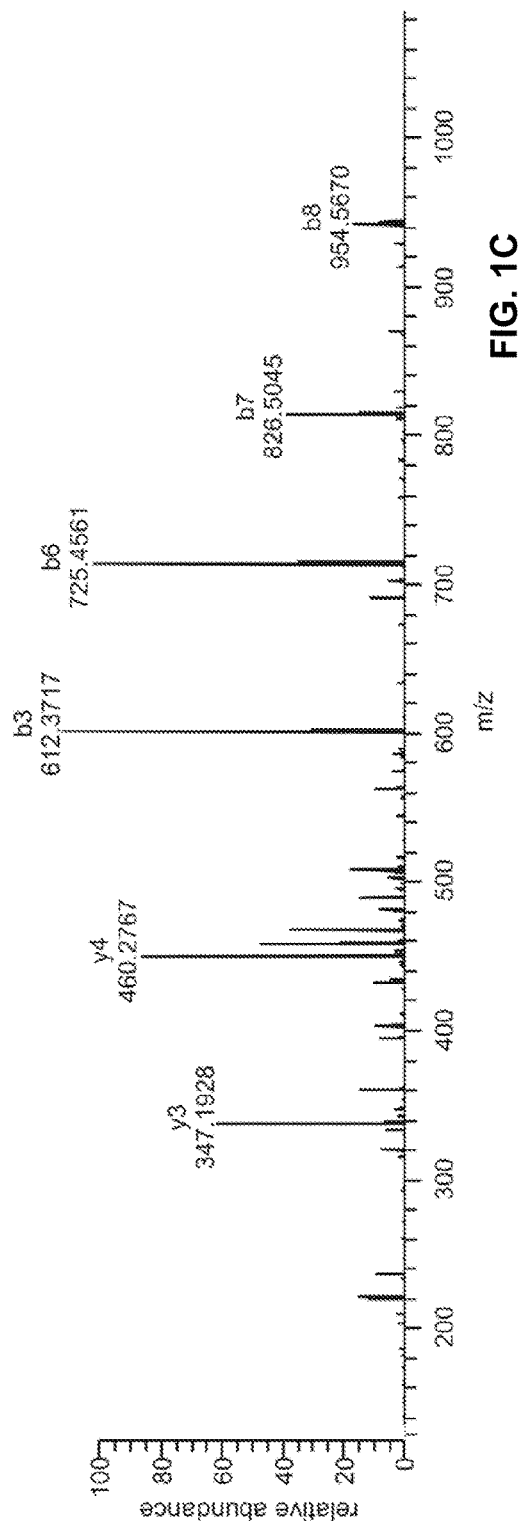
Figure 1D:
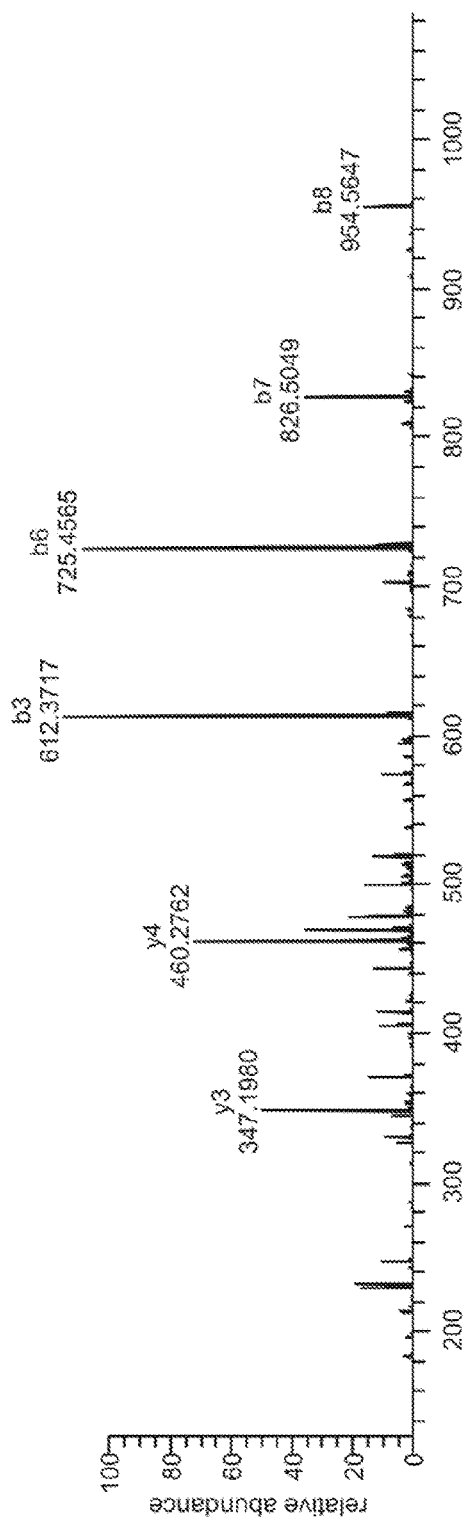

FIGS. 1A through 1D: FIG. 1A) Exemplary mass spectrum from IGF2BP3-001 demonstrating its presentation on primary tumor sample GB6010. NanoESI-LCMS was performed on a peptide pool eluted from the GBM sample GB6010. The mass chromatogram for m/z 536.3238±0.001 Da, z=2 shows a peptide peak at the retention time 49.89 min. FIG. 1B) The detected peak in the mass chromatogram at 48.76 min revealed a signal of m/z 536.3239 in the MS spectrum. FIG. 1C) A collisionally induced decay mass spectrum from the selected precursor m/z 536.3239 recorded in the nanoESI-LCMS experiment at the given retention time confirmed the presence of IGF2BP3-001 in the GB6010 tumor sample. FIG. 1D) The fragmentation pattern of the synthetic IGF2BP3-001 reference peptide was recorded and compared to the generated natural TUMAP fragmentation pattern shown in C for sequence verification.

Figure 2A:
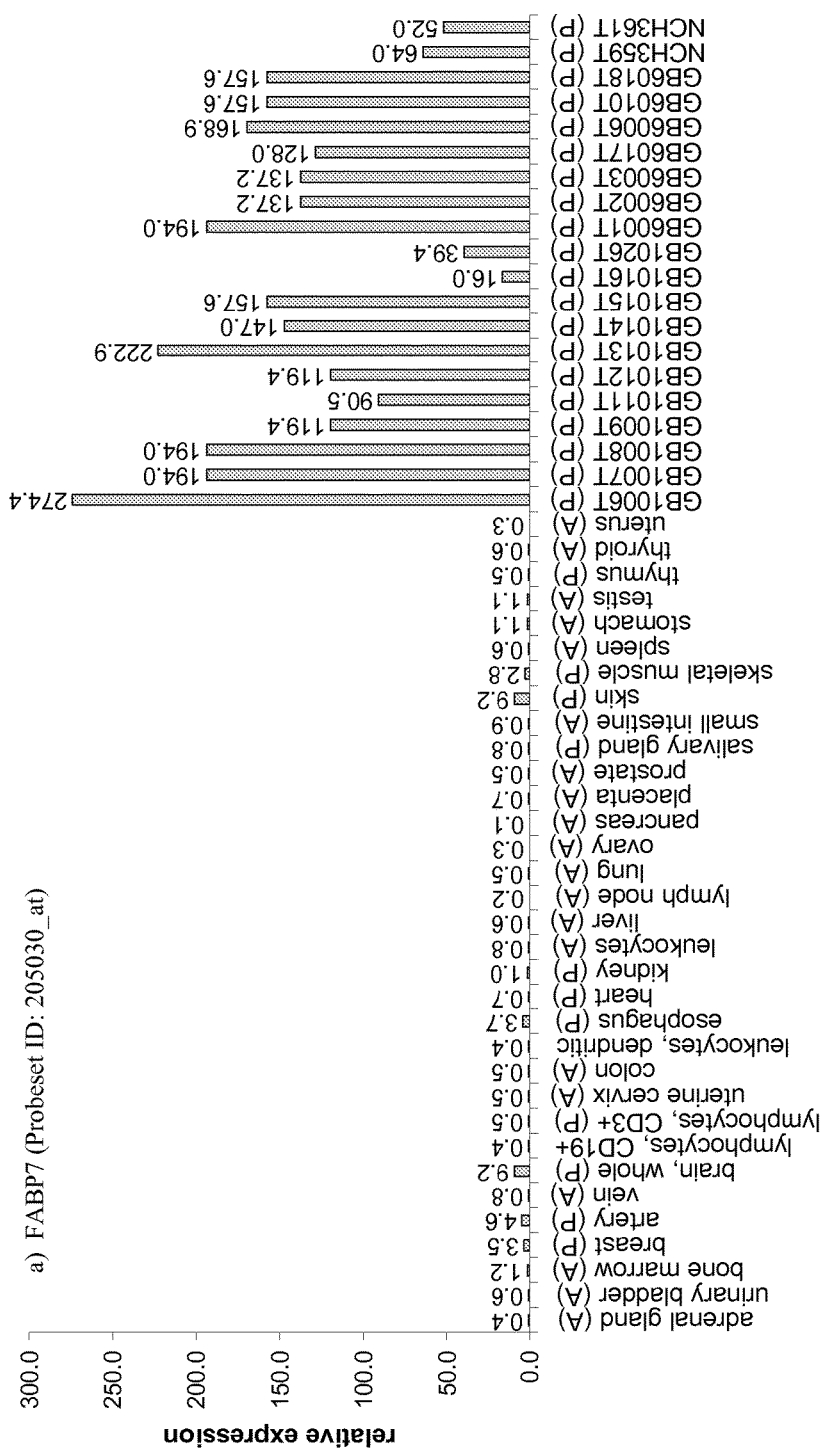
FIGS. 2A through 2D depict the mRNA expression profile of the target genes of the invention that are highly-overexpressed in glioblastoma samples. Expression of these genes is absent or very low in normal tissues while it is strongly increased in glioblastoma samples. Relative mRNA expressions are shown for several normal tissues and individual glioblastoma multiforme (GBM) samples measured by gene chip analysis. Values are relative to expression levels on normal kidney (value always arbitrarily set to 1.0). Values for normal tissues were generated with commercially available mRNA pools. Letters in brackets indicate the "detection call" as given by the analysis software. The "detection call" designates whether a transcript was specifically detected in the sample at all or whether no significant detection could be observed. It can take the values "P" (present), "A" (absent), or "M" (marginally detected).
Figure 2B:
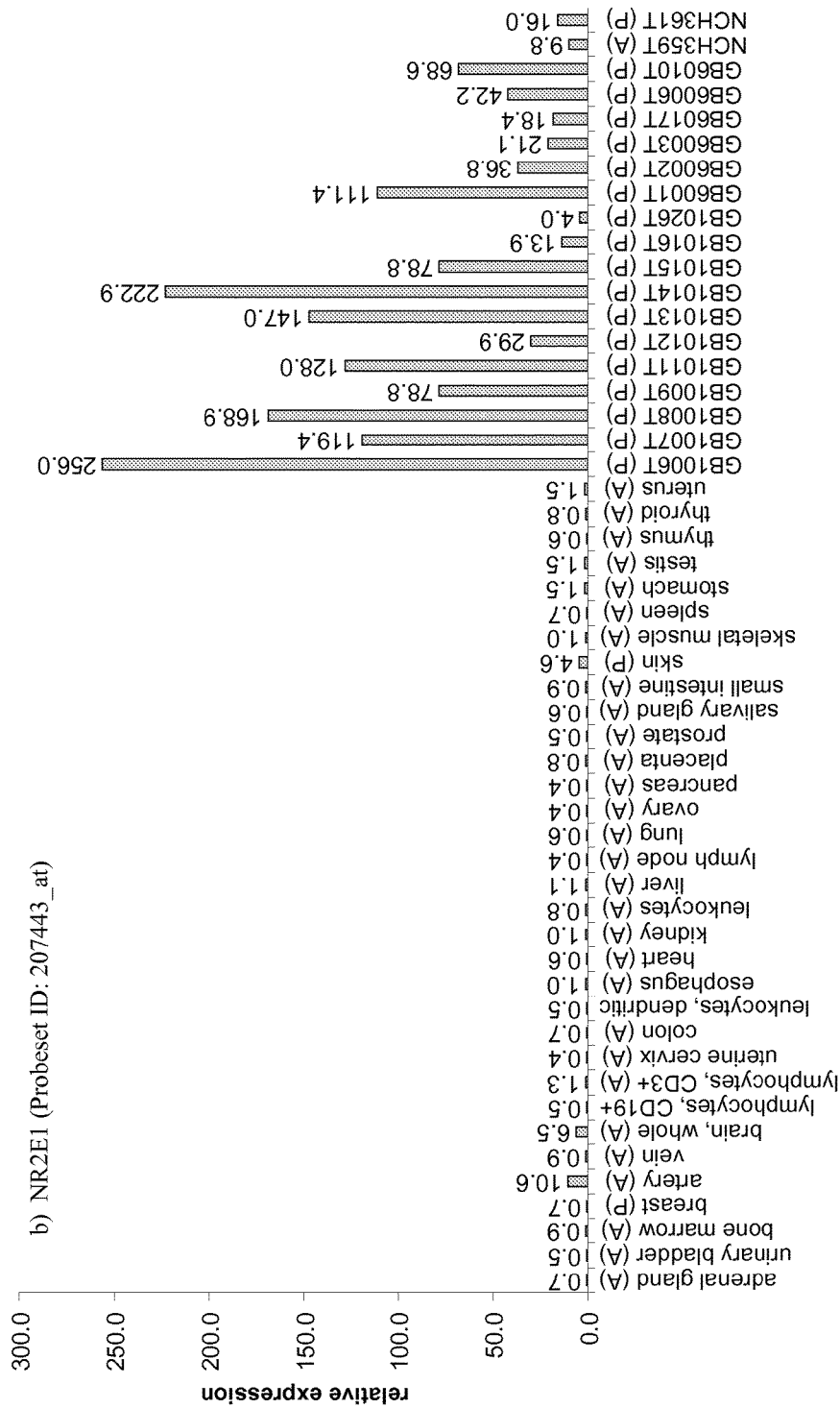

FIGS. 2A and 2B show the expression profiles of mRNA of selected proteins in normal tissues and in 19 glioblastoma samples.

Figure 2C:
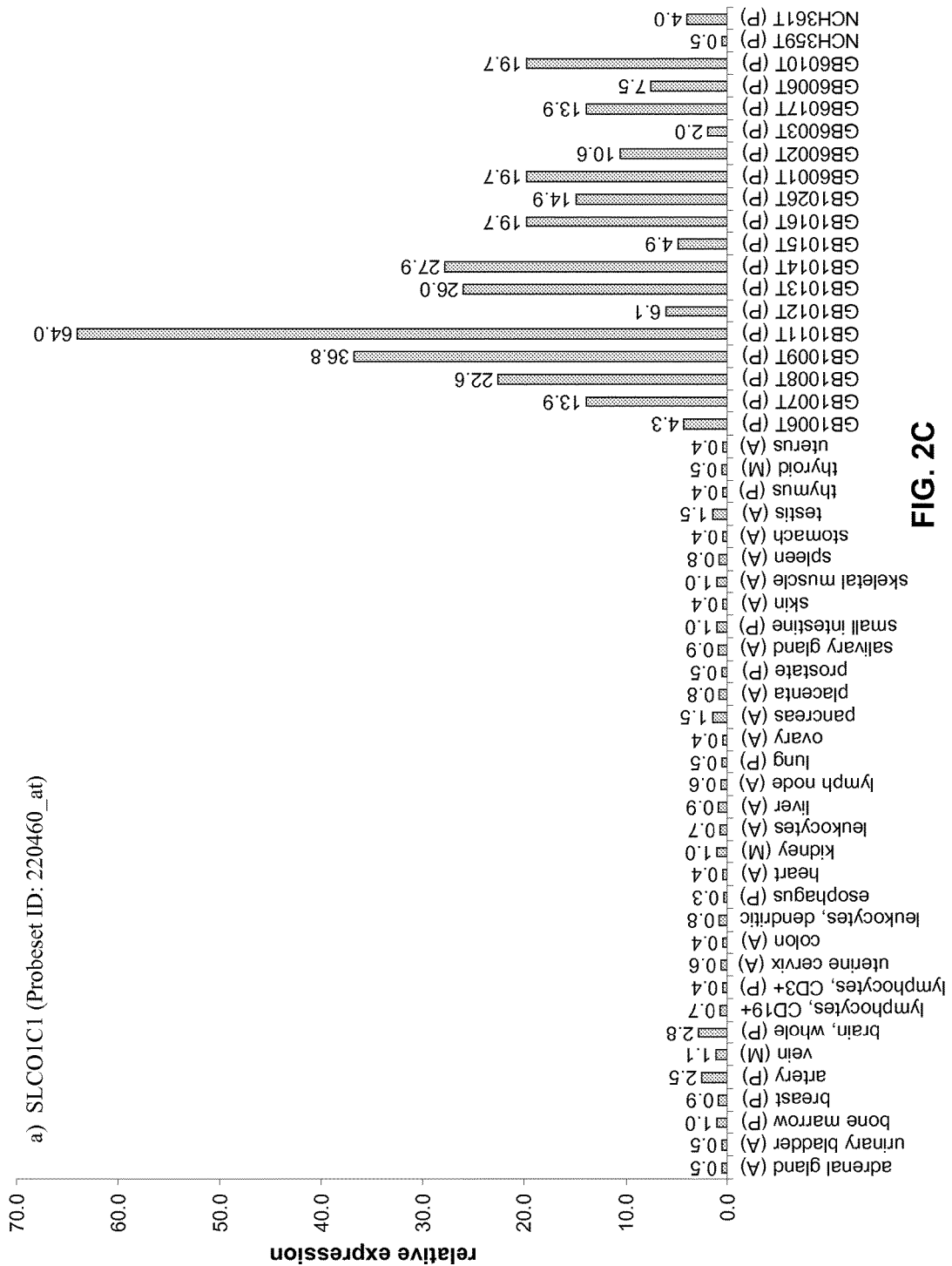
Figure 2D:
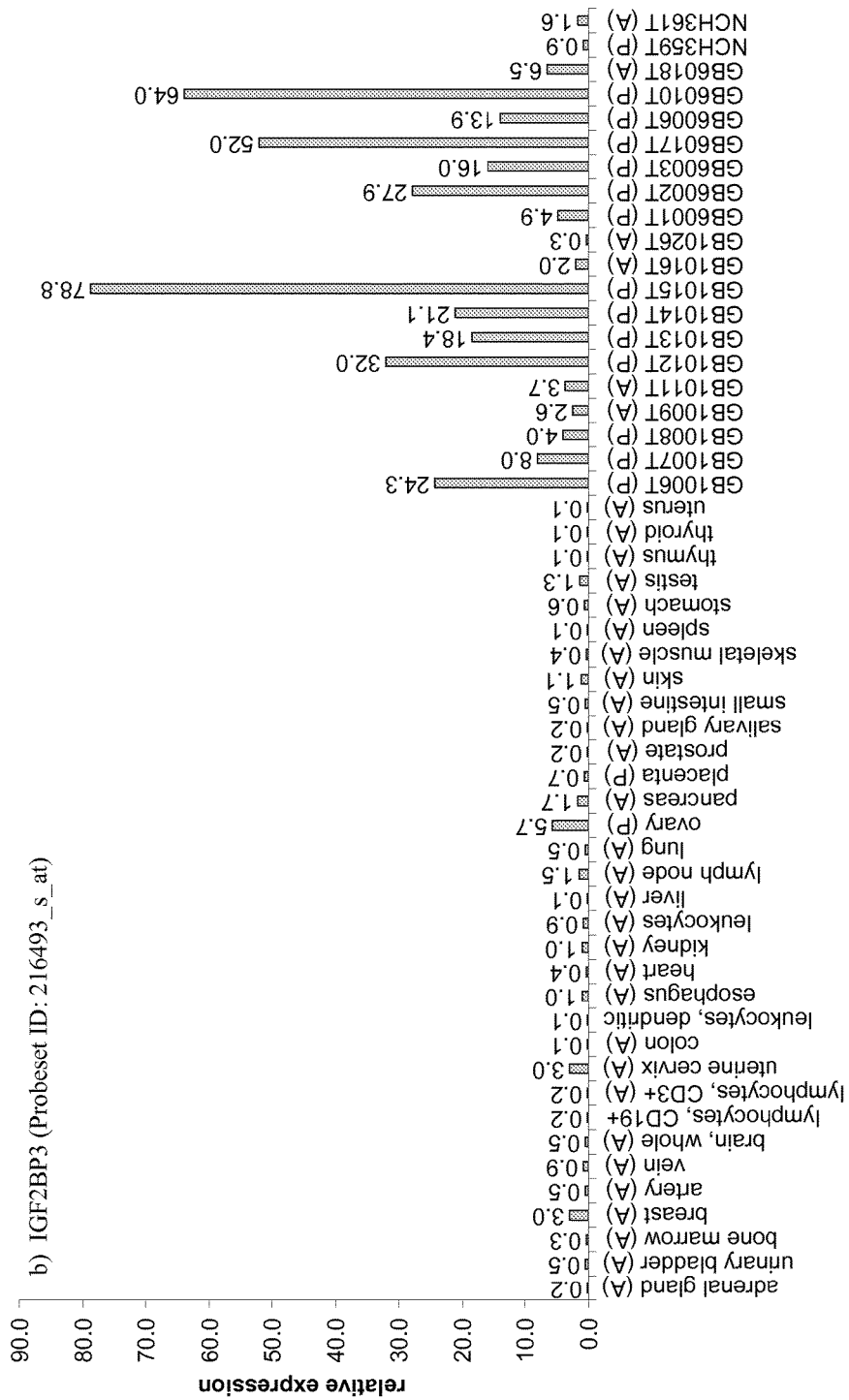
Figure 4:
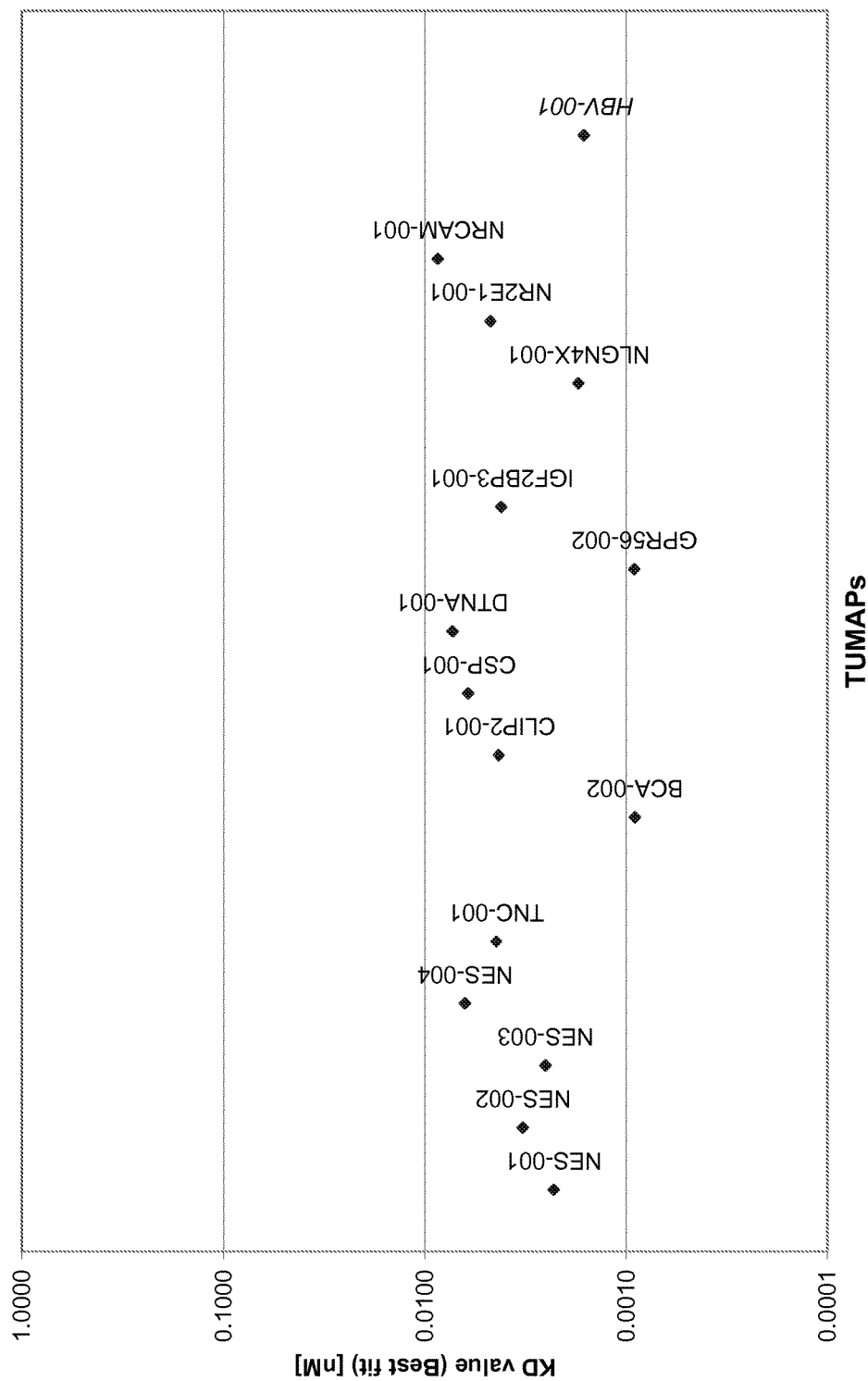
FIG. 4 shows the affinity of HLA class I peptides of the invention to the MHC molecule coded by the HLA-A*0201 allele. Dissociation constants ($K_D$) of HLA class I TUMAPs from the invention and the control peptide HBV-001 (strong A*02 binder) were measured by an ELISA-based MHC refolding assay.

FIGS. 2C and 2D show the expression profiles of mRNA of selected proteins in normal tissues and in 19 glioblastoma samples FIG. 3 shows the exemplary in vitro immunogenicity of IMA950 class I TUMAPs FIG. 4 shows the exemplary binding affinities of HLA class I peptides of the invention to A*02

SEQ ID Nos 1 to 24 show the sequences of preferred tumor associated peptides according to the present invention.

EXAMPLES

The peptides FTELTLGEF (HLA-A1; PolyPeptide Laboratories, Wolfenbüttel, Germany), LMLGEFLKL (HLA-A2; Clinalfa, Sissach, Switzerland), and EPDLAQCFY (HLA-B35; PolyPeptide Laboratories) were all obtained in pharmaceutical quality.

Example 1

Identification of Tumor Associated Peptides Presented on Cell Surface

Tissue Samples

Patients' tumor tissues were provided by Hôpital Cantonal Universitaire de Genève (Medical Oncology Laboratory of Tumor Immunology) and Neurochirurgische Universitäts-Klinik Heidelberg (Molekularbiologisches Labor). Written informed consents of all patients had been given before surgery. Tissues were shock-frozen in liquid nitrogen immediately after surgery and stored until isolation of TUMAPs at −80° C.

Isolation of HLA Peptides From Tissue Samples

HLA peptide pools from shock-frozen tissue samples were obtained by immune precipitation from solid tissues according to a slightly modified protocol (Falk, K. et al 1991; Seeger, F. H. et al. T 1999) using the HLA-A*02-specific antibody BB7.2 or the HLA-A,—B,—C-specific antibody W6/32, CNBr-activated sepharose, acid treatment, and ultrafiltration.

Methods:

The HLA peptide pools as obtained were separated according to their hydrophobicity by reversed-phase chromatography (Acquity UPLC system, Waters) and the eluting peptides were analyzed in an LTQ-Orbitrap hybrid mass spectrometer (ThermoElectron) equipped with an ESI source. Peptide pools were loaded directly onto the analytical fused-silica micro-capillary column (75 µm i.d.×250 mm) packed with 1.7 µm C18 reversed-phase material (Waters) applying a flow rate of 400 nL per minute. Subsequently, the peptides were separated using a two-step 180 minute-binary gradient from 10% to 33% B at flow rates of 300 nL per minute. The gradient was composed of Solvent A (0.1% formic acid in water) and solvent B (0.1% formic acid in acetonitrile). A gold coated glass capillary (PicoTip, New Objective) was used for introduction into the micro-ESI source. The LTQ-Orbitrap mass spectrometer was operated in the data-dependent mode using a TOPS strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide. FIGS. 1A through 1D show an exemplary spectrum obtained from tumor tissue for the MHC class I associated peptide IGF2BP3-001 and its elution profile on the UPLC system.

Example 2

Expression Profiling of Genes Encoding the Peptides of the Invention

Not all peptides identified as being presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. In order to identify such peptides and minimize the risk for autoimmunity induced by vaccination the inventors focused on those peptides that are derived from proteins that are over-expressed on tumor cells compared to the majority of normal tissues.

The ideal peptide will be derived from a protein that is unique to the tumor and not present in any other tissue. To identify peptides that are derived from genes with an expression profile similar to the ideal one the identified peptides were assigned to the proteins and genes, respectively, from which they were derived and expression profiles of these genes were generated.

RNA Sources and Preparation

Surgically removed tissue specimens were provided by two different clinical sites (see Example 1) after written informed consent had been obtained from each patient. Tumor tissue specimens were snap-frozen in liquid nitrogen immediately after surgery and later homogenized with mortar and pestle under liquid nitrogen. Total RNA was prepared from these samples using TRIzol (Invitrogen, Karlsruhe, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed such that RNA from each individual was equally weighted. Leukocytes were isolated from blood samples of 4 healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analyzed with the GCOS software (Affymetrix), using default settings for all parameters. For normalisation, 100 housekeeping genes provided by Affymetrix were used. Relative expression values were calculated from the signal log ratios given by the software and the normal kidney sample was arbitrarily set to 1.0.

The expression profiles of the source genes of the present invention that highly over-expressed in glioblastoma of the present invention are shown in FIGS. 2A through 2D.

Example 3

In Vitro Immunogenicity for IMA950 MHC Class I Presented Peptides

In order to obtain get information regarding the immunogenicity of the TUMAPs of the present invention, we performed investigations using a well established in vitro stimulation platform already described by (Walter, S, Herrgen, L, Schoor, O, Jung, G, Wernet, D, Buhring, H J, Rammensee, H G, and Stevanovic, S; 2003, Cutting edge: predetermined avidity of human CD8 T cells expanded on calibrated MHC/anti-CD28-coated microspheres, J.Immunol., 171, 4974-4978). This way we could show considerably high immunogenicity for 13 HLA-A*0201 restricted TUMAPs of the invention (in >=50% of tested donors TUMAP-specific CTLs could be detected) demonstrating that these peptides are T-cell eptiopes against which CD8+ precursor T cells exist in humans (Table 3).

In Vitro Priming of CD8+ T Cells

To perform in vitro stimulations by artificial antigen presenting cells (aAPC) loaded with peptide-MHC complex (pMHC) and anti-CD28 antibody, first we isolated PBMCs (peripheral blood mononuclear cells) from fresh HLA-A*02+ buffy coats by using standard density gradient separation medium (PAA, Colbe, Germany). Buffy coats were either obtained from the Blood Bank Tubingen or from the Katharinenhospital Stuttgart. Isolated PBMCs were incubated overnight in T-cell medium (TCM) for human in vitro priming consisting of RPMI-Glutamax (Invitrogen, Karlsruhe, Germany) supplemented with 10% heat inactivated human AB serum (PAA, Colbe, Germany), 100 U/ml Penicillin/100 µg/ml Streptomycin (Cambrex, Verviers, Belgium), 1 mM sodium pyruvate (CC Pro, Neustadt, Germany) and 20 µg/ml Gentamycin (Cambrex). CD8+ lymphocytes were isolated using the CD8+ MACS positive selection kit (Miltenyi, Bergisch Gladbach, Germany) according to the manufacturer's instructions. Obtained CD8+ T-cells were incubated until use in TCM supplemented with 2.5 ng/ml IL-7 (PromoCell, Heidelberg, Germany) and 10 U/ml IL-2 (Chiron, Munich, Gemany). Generation of pMHC/anti-CD28 coated beads, T-cell stimulations and readout was performed as described before (Walter et al., 2003) with minor modifications. Briefly, biotinylated recombinant HLA-A*0201 molecules lacking the transmembrane domain and biotinylated at the carboxy terminus of the heavy chain were produced following a method described by (Altman et al., 1996). The purified costimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). Beads used were 5.60 µm large streptavidin coated polystyrene particles (Bangs Laboratories, Illinois/USA). pMHC used as positive and negative controls were A*0201/MLA-001 (peptide ELAGIGILTV from modified Melan-A/MART-1) and A*0201/DDX5-001 (YLLPAIVHI from DDX5) or A*0201/HBV-001 (FLPSDFFPSV), respectively. 800.000 beads/200 µl were coated in 96-well plates in the presence of 600 ng biotin anti-CD28 plus 200 ng relevant biotin-pMHC (high density beads) or 2 ng relevant plus 200 ng irrelevant (pMHC library) MHC (low density beads). Stimulations were initiated in 96-well plates by co-incubating 1×10$^6$ CD8+ T cells with 2×10$^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. Finally, tetrameric analyses were performed with fluorescent MHC tetramers (produced as described by (Altman et al., 1996)) plus antibody CD8-FITC clone SK1 (BD, Heidelberg, Germany) on a four-color FACSCalibur (BD). Peptide specific cells were calculated as percentage of total CD8+ T cells. Evaluation of tetrameric analysis was done using the software FCS Express (De Novo Software). In vitro priming of specific tetramer+ CD8+ lymphocytes was detected by appropriate gating and by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T-cells and the percentage of specific tetramer+ cells was at least 10× the median of the negative control stimulations).

In Vitro Immunogenicity for IMA950 Peptides

For tested HLA class I peptides, in vitro immunogenicity could be demonstrated by generation of peptide specific T-cell lines. Exemplary flow cytometry results after TUMAP-specific tetramer staining for two peptides of the invention are shown in FIG. 3. Results for 13 peptides from the invention are summarized in Table 3.

TABLE 3

In vitro immunogenicity of highly immunogenic HLA class I peptides of the invention

| Antigen | Positive donors/ donors tested | Positive wells/ wells tested |
|---|---|---|
| BCA-001 | 60% | 5% |
| BCA-002 | 75% | 35% |
| CLIP2-001 | 75% | 6% |
| CSP-001 | 100% | 57% |
| FABP7-001 | 100% | 27% |
| IGF2BP3-001 | 50% | 21% |
| NES-001 | 75% | 38% |
| NLGN4X-001 | 100% | 62% |
| NRCAM-001 | 86% | 39% |
| PDPN-001 | 60% | 11% |
| SLCO1C1-001 | 60% | 7% |
| TNC-001 | 60% | 30% |
| TNC-002 | 50% | 14% |

In addition to these results obtained from healthy blood donors, the peptides BCA-002, CHI3L1-001, and NLGN4X-001 were also tested in a small number of glioblastoma patients. All peptides proved to be immunogenic to a similar extent compared with healthy donors, demonstrating the existence of precursor T cells in a relevant target population for the vaccine.

Example 4

Binding of HLA Class I-Restricted Peptides of the Invention to HLA-A*0201

Objective and Summary

The objective of this analysis was to evaluate the affinity of the HLA class I peptides to the MHC molecule coded by the HLA-A*0201 allele as this is an important parameter for the mode of action of peptides as part of cancer immunotherapies. Affinities to HLA-A*0201 were medium to high for all tested HLA class I-restricted peptide 0 of the invention, with dissociation constants in the range of the positive control peptide HBV-001, a known strong A*02 binder derived from hepatitis B virus core antigen. These results confirmed the strong binding affinity of all tested HLA class I peptides of the present invention.

Principle of Test

Stable HLA/peptide complexes consist of three molecules: HLA heavy chain, beta-2 microglobulin (b2m) and the peptidic ligand. The activity of denatured recombinant HLA-A*0201 heavy chain molecules alone can be preserved making them functional equivalents of "empty HLA-A*0201 molecules". When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule (Sylvester-Hvid et al., 2002).

Purified recombinant HLA-A*0201 molecules were incubated together with b2m and graded doses of the peptide of interest. The amount of de novo-folded HLA/peptide complexes was determined by a quantitative ELISA. Dissociation constants (KD values) were calculated using a standard curve recorded from dilutions of a calibrant HLA/peptide complex.

Results

Results are shown in FIG. 4. A lower KD value reflects higher affinity to HLA-A*0201. All tested peptides of the invention had a strong affinities to HLA-A*0201 around the KD for the positive control peptide HBV-001, a known strong A*02 binder. Thereby, all class I TUMAPs of the invention have a strong binding affinity to the MHC molecule A*02.

REFERENCE LIST

About I, Laurent-Maquin D, Lendahl U, Mitsiadis T A (2000). Nestin expression in embryonic and adult human teeth under normal and pathological conditions. Am J Pathol. 157, 287-295.

Aghi M, Gaviani P, Henson J W, Batchelor T T, Louis D N, Barker F G (2005). Magnetic resonance imaging characteristics predict epidermal growth factor receptor amplification status in glioblastoma. Clin Cancer Res. 11, 8600-8605.

Agosti R M, Leuthold M, Gullick W J, Yasargil M G, Wiestler O D (1992). Expression of the epidermal growth factor receptor in astrocytic tumours is specifically associated with glioblastoma multiforme. Virchows Arch. A Pathol. Anat. Histopathol. 420, 321-325.

Al-Joudi F S, Iskandar Z A, Imran A K (2007). Survivin expression correlates with unfavourable prognoses in invasive ductal carcinoma of the breast. Med J Malaysia 62, 6-8.

Al-Nedawi K, Meehan B, Micallef J, Lhotak V, May L, Guha A, Rak J (2008). Intercellular transfer of the oncogenic receptor EGFRvIII by microvesicles derived from tumour cells. Nat. Cell Biol.

Altman J D, Moss P A, Goulder P J, Barouch D H, Heyzer-Williams M G, Bell J I, McMichael A J, Davis M M (1996). Phenotypic analysis of antigen-specific T lymphocytes. Science 274, 94-96.

Amoh Y, Yang M, Li L, Reynoso J, Bouvet M, Moossa A R, Katsuoka K, Hoffman R M (2005). Nestin-linked green fluorescent protein transgenic nude mouse for imaging human tumor angiogenesis. Cancer Res. 65, 5352-5357.

Angileri F F, Aguennouz M, Conti A, La T D, Cardali S, Crupi R, Tomasello C, Germano A, Vita G, Tomasello F (2008). Nuclear factor-kappaB activation and differential expression of survivin and Bcl-2 in human grade 2-4 astrocytomas. Cancer.

Appay V, Speiser D E, Rufer N, Reynard S, Barbey C, Cerottini J C, Leyvraz S, Pinilla C, Romero P (2006). Decreased specific CD8+ T cell cross-reactivity of antigen recognition following vaccination with Melan-A peptide. Eur. J Immunol. 36, 1805-1814.

Arnold S E, Trojanowski J Q (1996). Human fetal hippocampal development: II. The neuronal cytoskeleton. J Comp Neurol. 367, 293-307.

ARONSON S M, ARONSON B E (1965). CENTRAL NERVOUS SYSTEM IN DIABETES MELLITUS: LOWERED FREQUENCY OF CERTAIN INTRACRANIAL NEOPLASMS. Arch. Neurol. 12, 390-398.

Asheuer M, Bieche I, Laurendeau I, Moser A, Hainque B, Vidaud M, Aubourg P (2005). Decreased expression of ABCD4 and BG1 genes early in the pathogenesis of X-linked adrenoleukodystrophy. Hum. Mol. Genet. 14, 1293-1303.

Asklund T, Appelskog I B, Ammerpohl O, Ekstrom T J, Almqvist P M (2004). Histone deacetylase inhibitor 4-phenylbutyrate modulates glial fibrillary acidic protein and connexin 43 expression, and enhances gap-junction communication, in human glioblastoma cells. Eur. J Cancer 40, 1073-1081.

Barker F G, Simmons M L, Chang S M, Prados M D, Larson D A, Sneed P K, Wara W M, Berger M S, Chen P, Israel M A, Aldape K D (2001). EGFR overexpression and radiation response in glioblastoma multiforme. Int. J Radiat. Oncol Biol. Phys. 51, 410-418.

Bertelli E, Regoli M, Fonzi L, Occhini R, Mannucci S, Ermini L, Toti P (2007). Nestin expression in adult and developing human kidney. J Histochem. Cytochem. 55, 411-421.

Blum R, Jacob-Hirsch J, Rechavi G, Kloog Y (2006). Suppression of survivin expression in glioblastoma cells by the Ras inhibitor farnesylthiosalicylic acid promotes caspase-dependent apoptosis. Mol. Cancer Ther. 5, 2337-2347.

Bourdon M A, Wikstrand C J, Furthmayr H, Matthews T J, Bigner D D (1983). Human glioma-mesenchymal extracellular matrix antigen defined by monoclonal antibody. Cancer Res. 43, 2796-2805.

Bowen A R, Hanks A N, Murphy K J, Florell S R, Grossman D (2004). Proliferation, apoptosis, and survivin expression in keratinocytic neoplasms and hyperplasias. Am J Dermatopathol. 26, 177-181.

Boyton R J, Lohmann T, Londei M, Kalbacher H, Halder T, Frater A J, Douek D C, Leslie D G, Flavell R A, Altmann D M (1998). Glutamic acid decarboxylase T lymphocyte responses associated with susceptibility or resistance to type I diabetes: analysis in disease discordant human twins, non-obese diabetic mice and HLA-DQ transgenic mice. Int. Immunol. 10, 1765-1776.

Brekke C, Lundervold A, Enger P O, Brekken C, Stalsett E, Pedersen T B, Haraldseth O, Kruger P G, Bjerkvig R, Chekenya M (2006). NG2 expression regulates vascular morphology and function in human brain tumours. Neuroimage. 29, 965-976.

Brenner A V, Linet M S, Fine H A, Shapiro W R, Selker R G, Black P M, Inskip P D (2002). History of allergies and autoimmune diseases and risk of brain tumors in adults. Int. J Cancer 99, 252-259.

Brommeland T, Rosengren L, Fridlund S, Hennig R, Isaksen V (2007). Serum levels of glial fibrillary acidic protein correlate to tumour volume of high-grade gliomas. Acta Neurol. Scand. 116, 380-384.

Bronger H, Konig J, Kopplow K, Steiner H H, Ahmadi R, Herold-Mende C, Keppler D, Nies A T (2005). ABCC drug efflux pumps and organic anion uptake transporters in human gliomas and the blood-tumor barrier. Cancer Res. 65, 11419-11428.

Brychtova S, Fiuraskova M, Hlobilkova A, Brychta T, Hirnak J (2007). Nestin expression in cutaneous melanomas and melanocytic nevi. J Cutan. Pathol. 34, 370-375.

Buchner A, Castro M, Hennig A, Popp T, Assmann G, Hofstetter A, Stief C, Zimmermann W (2007). [Transcriptome analyses in renal cell carcinoma. Combination of laser microdissection and microarrays]. Urologe A 46, 1170-1175.

Calvo A, Catena R, Noble M S, Carbott D, Gil-Bazo I, Gonzalez-Moreno O, Huh J I, Sharp R, Qiu T H, Anver M R, Merlino G, Dickson R B, Johnson M D, Green J E (2008). Identification of VEGF-regulated genes associated with increased lung metastatic potential: functional involvement of tenascin-C in tumor growth and lung metastasis. Oncogene.

Campoli M R, Chang C C, Kageshita T, Wang X, McCarthy J B, Ferrone S (2004). Human high molecular weight-melanoma-associated antigen (HMW-MAA): a melanoma cell surface chondroitin sulfate proteoglycan (MSCP) with biological and clinical significance. Crit Rev. Immunol. 24, 267-296.

Carnemolla B, Castellani P, Ponassi M, Borsi L, Urbini S, Nicolo G, Dorcaratto A, Viale G, Winter G, Neri D, Zardi L (1999). Identification of a glioblastoma-associated tenascin-C isoform by a high affinity recombinant antibody. Am J Pathol. 154, 1345-1352.

Carriere C, Seeley E S, Goetze T, Longnecker D S, Korc M (2007). The Nestin progenitor lineage is the compartment of origin for pancreatic intraepithelial neoplasia. Proc Natl. Acad. Sci. U.S.A 104, 4437-4442.

Casati C, Dalerba P, Rivoltini L, Gallino G, Deho P, Rini F, Belli F, Mezzanzanica D, Costa A, Andreola S, Leo E, Parmiani G, Castelli C (2003). The apoptosis inhibitor protein survivin induces tumor-specific CD8+ and CD4+ T cells in colorectal cancer patients. Cancer Res. 63, 4507-4515.

Castellino F, Huang A Y, tan-Bonnet G, Stoll S, Scheinecker C, Germain R N (2006). Chemokines enhance immunity by guiding naive CD8+ T cells to sites of CD4+ T cell-dendritic cell interaction. Nature 440, 890-895.

Chakravarti A, Noll E, Black P M, Finkelstein D F, Finkelstein D M, Dyson N J, Loeffler J S (2002). Quantitatively determined survivin expression levels are of prognostic value in human gliomas. J Clin Oncol 20, 1063-1068.

Cheever M A, Chen W, Disis M L, Takahashi M, Peace D J (1993). T-cell immunity to oncogenic proteins including mutated ras and chimeric bcr-abl. Ann N. Y. Acad. Sci. 690, 101-112.

Chekenya M, Enger P O, Thorsen F, Tysnes B B, Al-Sarraj S, Read T A, Furmanek T, Mahesparan R, Levine J M, Butt A M, Pilkington G J, Bjerkvig R (2002a). The glial precursor proteoglycan, NG2, is expressed on tumour neovasculature by vascular pericytes in human malignant brain tumours. Neuropathol. Appl. Neurobiol. 28, 367-380.

Chekenya M, Hjelstuen M, Enger P O, Thorsen F, Jacob A L, Probst B, Haraldseth O, Pilkington G, Butt A, Levine J M, Bjerkvig R (2002b). NG2 proteoglycan promotes angiogenesis-dependent tumor growth in CNS by sequestering angiostatin. FASEB J 16, 586-588.

Chekenya M, Immervoll H (2007). NG2/HMP proteoglycan as a cancer therapeutic target. Methods Mol. Biol. 361, 93-117.

Chekenya M, Krakstad C, Svendsen A, Netland I A, Staalesen V, Tysnes B B, Selheim F, Wang J, Sakariassen P O, Sandal T, Lonning P E, Flatmark T, Enger P O, Bjerkvig R, Sioud M, Stallcup W B (2008). The progenitor cell marker NG2/MPG promotes chemoresistance by activation of integrin-dependent PI3K/Akt signaling. Oncogene.

Chekenya M, Pilkington G J (2002). NG2 precursor cells in neoplasia: functional, histogenesis and therapeutic implications for malignant brain tumours. J Neurocytol. 31, 507-521.

Chekenya M, Rooprai H K, Davies D, Levine J M, Butt A M, Pilkington G J (1999). The NG2 chondroitin sulfate proteoglycan: role in malignant progression of human brain tumours. Int J Dev. Neurosci. 17, 421-435.

Chiquet-Ehrismann R, Tucker RP (2004). Connective tissues: signalling by tenascins. Int. J Biochem. Cell Biol. 36, 1085-1089.

Chu C, Li J Y, Boado R J, Pardridge W M (2008). Blood-brain barrier genomics and cloning of a novel organic anion transporter. J Cereb. Blood Flow Metab 28, 291-301.

Colin C, Baeza N, Bartoli C, Fina F, Eudes N, Nanni I, Martin P M, Ouafik L, Figarella-Branger D (2006). Identification of genes differentially expressed in glioblastoma versus pilocytic astrocytoma using Suppression Subtractive Hybridization. Oncogene 25, 2818-2826.

Colombetti S, Basso V, Mueller D L, Mondino A (2006). Prolonged TCR/CD28 engagement drives IL-2-independent T cell clonal expansion through signaling mediated by the mammalian target of rapamycin. J Immunol. 176, 2730-2738.

Conacci-Sorrell M, Kaplan A, Raveh S, Gavert N, Sakurai T, Ben-Ze'ev A (2005). The shed ectodomain of Nr-CAM stimulates cell proliferation and motility, and confers cell transformation. Cancer Res. 65, 11605-11612.

Conacci-Sorrell M E, Ben-Yedidia T, Shtutman M, Feinstein E, Einat P, Ben-Ze'ev A (2002). Nr-CAM is a target gene of the beta-catenin/LEF-1 pathway in melanoma and colon cancer and its expression enhances motility and confers tumorigenesis. Genes Dev. 16, 2058-2072.

Coskun U, Yamac D, Gulbahar O, Sancak B, Karaman N, Ozkan S (2007). Locally advanced breast carcinoma treated with neoadjuvant chemotherapy: are the changes in serum levels of YKL-40, MMP-2 and MMP-9 correlated with tumor response? Neoplasma 54, 348-352.

Cresswell P (1994). Assembly, transport, and function of MHC class II molecules. Annu. Rev. Immunol. 12, 259-293.

Dahlstrand J, Collins V P, Lendahl U (1992). Expression of the class VI intermediate filament nestin in human central nervous system tumors. Cancer Res. 52, 5334-5341.

Dengjel J, Nastke M D, Gouttefangeas C, Gitsioudis G, Schoor O, Altenberend F, Muller M, Kramer B, Missiou A, Sauter M, Hennenlotter J, Wernet D, Stenzl A, Rammensee H G, Klingel K, Stevanovic S (2006). Unexpected Abundance of HLA Class II Presented Peptides in Primary Renal Cell Carcinomas. Clin Cancer Res. 12, 4163-4170.

Dixon D N, Izon D J, Dagger S, Callow M J, Taplin R H, Kees U R, Greene W K (2007). TLX transcription factor inhibits differentiation and promotes a non-haemopoietic phenotype in murine bone marrow cells. Br. J Haematol. 138, 54-67.

Domoto T, Miyama Y, Suzuki H, Teratani T, Arai K, Sugiyama T, Takayama T, Mugiya S, Ozono S, Nozawa R (2007). Evaluation of S100A10, annexin II and B-FABP expression as markers for renal cell carcinoma. Cancer Sci. 98, 77-82.

Dudley M E, Wunderlich J R, Robbins P F, Yang J C, Hwu P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A (2002). Cancer regression and autoimmunity in patients after clonal repopulation with antitumor lymphocytes. Science 298, 850-854.

Dudley M E, Wunderlich J R, Yang J C, Sherry R M, Topalian S L, Restifo N P, Royal R E, Kammula U, White D E, Mavroukakis S A, Rogers L J, Gracia G J, Jones S A, Mangiameli D P, Pelletier M M, Gea-Banacloche J, Robinson M R, Berman D M, Filie A C, Abati A, Rosenberg S A (2005). Adoptive cell transfer therapy following non-myeloablative but lymphodepleting chemotherapy for the treatment of patients with refractory metastatic melanoma. J. Clin. Oncol. 23, 2346-2357.

Eppenberger U, Mueller H (1994). Growth factor receptors and their ligands. J Neurooncol. 22, 249-254.

Erfurt C, Sun Z, Haendle I, Schuler-Thurner B, Heirman C, Thielemans K, van der B P, Schuler G, Schultz E S (2007). Tumor-reactive CD4+ T cell responses to the melanoma-associated chondroitin sulphate proteoglycan in melanoma patients and healthy individuals in the absence of autoimmunity. J Immunol. 178, 7703-7709.

Florenes V A, Holm R, Myklebost O, Lendahl U, Fodstad O (1994). Expression of the neuroectodermal intermediate filament nestin in human melanomas. Cancer Res. 54, 354-356.

Fong L, Hou Y, Rivas A, Benike C, Yuen A, Fisher G A, Davis M M, Engleman E G (2001). Altered peptide ligand vaccination with Flt3 ligand expanded dendritic cells for tumor immunotherapy. Proc. Natl. Acad. Sci. U.S.A 98, 8809-8814.

Galli R, Binda E, Orfanelli U, Cipelletti B, Gritti A, De V S, Fiocco R, Foroni C, Dimeco F, Vescovi A (2004). Isolation and characterization of tumorigenic, stem-like neural precursors from human glioblastoma. Cancer Res. 64, 7011-7021.

Galon J, Costes A, Sanchez-Cabo F, Kirilovsky A, Mlecnik B, Lagorce-Pages C, Tosolini M, Camus M, Berger A, Wind P, Zinzindohoue F, Bruneval P, Cugnenc P H, Trajanoski Z, Fridman W H, Pages F (2006). Type, density, and location of immune cells within human colorectal tumors predict clinical outcome. Science 313, 1960-1964.

Garcion E, Halilagic A, Faissner A, ffrench-Constant C (2004). Generation of an environmental niche for neural stem cell development by the extracellular matrix molecule tenascin C. Development 131, 3423-3432.

Gary S C, Kelly G M, Hockfield S (1998). BEHAB/brevican: a brain-specific lectican implicated in gliomas and glial cell motility. Curr. Opin. Neurobiol. 8, 576-581.

Gary S C, Zerillo C A, Chiang V L, Gaw J U, Gray G, Hockfield S (2000). cDNA cloning, chromosomal localization, and expression analysis of human BEHAB/brevican, a brain specific proteoglycan regulated during cortical development and in glioma. Gene 256, 139-147.

Gattinoni L, Powell D J, Jr., Rosenberg S A, Restifo N P (2006). Adoptive immunotherapy for cancer: building on success. Nat. Rev. Immunol. 6, 383-393.

Ghosh J C, Dohi T, Kang B H, Altieri D C (2008). Hsp60 regulation of tumor cell apoptosis. J Biol. Chem. 283, 5188-5194.

Gipp J, Gu G, Crylen C, Kasper S, Bushman W (2007). Hedgehog pathway activity in the LADY prostate tumor model. Mol. Cancer 6, 19.

Gleiberman A S, Michurina T, Encinas J M, Roig J L, Krasnov P, Balordi F, Fishell G, Rosenfeld M G, Enikolopov G (2008). Genetic approaches identify adult pituitary stem cells. Proc Natl. Acad. Sci. U.S.A 105, 6332-6337.

Gnjatic S, Atanackovic D, Jager E, Matsuo M, Selvakumar A, Altorki N K, Maki R G, Dupont B, Ritter G, Chen Y T, Knuth A, Old L J (2003). Survey of naturally occurring CD4+ T cell responses against NY-ESO-1 in cancer patients: correlation with antibody responses. Proc Natl. Acad. Sci. U.S.A 100, 8862-8867.

Godbout R, Bisgrove D A, Shkolny D, Day R S, III (1998). Correlation of B-FABP and GFAP expression in malignant glioma. Oncogene 16, 1955-1962.

Gorka B, Skubis-Zegadlo J, Mikula M, Bardadin K, Paliczka E, Czarnocka B (2007). NrCAM, a neuronal system cell-adhesion molecule, is induced in papillary thyroid carcinomas. Br. J Cancer 97, 531-538.

Goto Y, Matsuzaki Y, Kurihara S, Shimizu A, Okada T, Yamamoto K, Murata H, Takata M, Aburatani H, Hoon D S, Saida T, Kawakami Y (2006). A new melanoma antigen fatty acid-binding protein 7, involved in proliferation and invasion, is a potential target for immunotherapy and molecular target therapy. Cancer Res. 66, 4443-4449.

Grunda J M, Nabors L B, Palmer C A, Chhieng D C, Steg A, Mikkelsen T, Diasio R B, Zhang K, Allison D, Grizzle W E, Wang W, Gillespie G Y, Johnson M R (2006). Increased expression of thymidylate synthetase (TS), ubiquitin specific protease 10 (USP10) and survivin is associated with poor survival in glioblastoma multiforme (GBM). J Neurooncol. 80, 261-274.

Gu G, Yuan J, Wills M, Kasper S (2007). Prostate cancer cells with stem cell characteristics reconstitute the original human tumor in vivo. Cancer Res. 67, 4807-4815.

Gunther H S, Schmidt N O, Phillips H S, Kemming D, Kharbanda S, Soriano R, Modrusan Z, Meissner H, Westphal M, Lamszus K (2008). Glioblastoma-derived stem cell-enriched cultures form distinct subgroups according to molecular and phenotypic criteria. Oncogene 27, 2897-2909.

Hammer J, Gallazzi F, Bono E, Karr R W, Guenot J, Valsasnini P, Nagy Z A, Sinigaglia F (1995). Peptide binding specificity of HLA-DR4 molecules: correlation with rheumatoid arthritis association. J Exp. Med 181, 1847-1855.

Hanada K, Yewdell J W, Yang J C (2004). Immune recognition of a human renal cancer antigen through post-translational protein splicing. Nature 427, 252-256.

Hau P, Kunz-Schughart L A, Rummele P, Arslan F, Dorfelt A, Koch H, Lohmeier A, Hirschmann B, Muller A, Bogdahn U, Bosserhoff A K (2006). Tenascin-C protein is induced by transforming growth factor-beta1 but does not correlate with time to tumor progression in high-grade gliomas. J Neurooncol. 77, 1-7.

Heimberger A B, Hussain S F, Aldape K, Sawaya R, Archer G A, Friedman H, Reardon D, Friedman A, Bigner D D, Sampson J H. Tumor-specific peptide vaccination in newly-diagnosed patients with GBM. Journal of Clinical Oncology, 2006 ASCO Annual Meeting Proceedings Part I Vol 24, No. 18S (June 20 Supplement), 2006: 2529. 6-20-2006.

Herold-Mende C, Mueller M M, Bonsanto M M, Schmitt H P, Kunze S, Steiner H H (2002). Clinical impact and functional aspects of tenascin-C expression during glioma progression. Int. J Cancer 98, 362-369.

Herrera M B, Bruno S, Buttiglieri S, Tetta C, Gatti S, Deregibus M C, Bussolati B, Camussi G (2006). Isolation and characterization of a stem cell population from adult human liver. Stem Cells 24, 2840-2850.

Hoffmann N E, Sheinin Y, Lohse C M, Parker A S, Leibovich B C, Jiang Z, Kwon E D (2008). External validation of IMP3 expression as an independent prognostic marker for metastatic progression and death for patients with clear cell renal cell carcinoma. Cancer 112, 1471-1479.

Hormigo A, Gu B, Karimi S, Riedel E, Panageas K S, Edgar M A, Tanwar M K, Rao J S, Fleisher M, DeAngelis L M, Holland E C (2006). YKL-40 and matrix metalloproteinase-9 as potential serum biomarkers for patients with high-grade gliomas. Clin Cancer Res. 12, 5698-5704.

Huang J, Hu J, Bian X, Chen K, Gong W, Dunlop N M, Howard O M, Wang J M (2007). Transactivation of the epidermal growth factor receptor by formylpeptide receptor exacerbates the malignant behavior of human glioblastoma cells. Cancer Res. 67, 5906-5913.

Huang Y, Fan J, Yang J, Zhu G Z (2008). Characterization of GPR56 protein and its suppressed expression in human pancreatic cancer cells. Mol. Cell Biochem. 308, 133-139.

Huncharek M, Kupelnick B (2000). Epidermal growth factor receptor gene amplification as a prognostic marker in glioblastoma multiforme: results of a meta-analysis. Oncol Res. 12, 107-112.

Hwang M L, Lukens J R, Bullock T N (2007). Cognate memory CD4+ T cells generated with dendritic cell priming influence the expansion, trafficking, and differentiation of secondary CD8+ T cells and enhance tumor control. J Immunol. 179, 5829-5838.

Iguchi T, Sakata K, Yoshizaki K, Tago K, Mizuno N, Itoh H (2008). Orphan G protein-coupled receptor GPR56 regulates neural progenitor cell migration via a Galpha 12/13 and Rho pathway. J Biol. Chem.

Ilja Boor P K, de G K, Mejaski-Bosnjak V, Brenner C, van der Knaap M S, Scheper G C, Pronk J C (2006). Megalencephalic leukoencephalopathy with subcortical cysts: an update and extended mutation analysis of MLC1. Hum. Mutat. 27, 505-512.

Ishiuchi S, Tsuzuki K, Yoshida Y, Yamada N, Hagimura N, Okado H, Miwa A, Kurihara H, Nakazato Y, Tamura M, Sasaki T, Ozawa S (2002). Blockage of Ca(2+)-permeable AMPA receptors suppresses migration and induces apoptosis in human glioblastoma cells. Nat. Med 8, 971-978.

Ishizaki M, Ishiwata T, Adachi A, Tamura N, Ghazizadeh M, Kitamura H, Sugisaki Y, Yamanaka N, Naito Z, Fukuda Y (2006). Expression of nestin in rat and human glomerular podocytes. J Submicrosc. Cytol. Pathol. 38, 193-200.

Janssen E M, Lemmens E E, Wolfe T, Christen U, von Herrath M G, Schoenberger SP (2003). CD4+ T cells are required for secondary expansion and memory in CD8+ T lymphocytes. Nature 421, 852-856.

Jaworski D M, Kelly G M, Piepmeier J M, Hockfield S (1996). BEHAB (brain enriched hyaluronan binding) is expressed in surgical samples of glioma and in intracranial grafts of invasive glioma cell lines. Cancer Res. 56, 2293-2298.

Jiang Z, Chu P G, Woda B A, Rock K L, Liu Q, Hsieh C C, Li C, Chen W, Duan H O, McDougal S, Wu C L (2006). Analysis of RNA-binding protein IMP3 to predict metastasis and prognosis of renal-cell carcinoma: a retrospective study. Lancet Oncol 7, 556-564.

Jiang Z, Lohse C M, Chu P G, Wu C L, Woda B A, Rock K L, Kwon ED (2008). Oncofetal protein IMP3: a novel molecular marker that predicts metastasis of papillary and chromophobe renal cell carcinomas. Cancer 112, 2676-2682.

Johansen J S, Jensen B V, Roslind A, Nielsen D, Price P A (2006). Serum YKL-40, a new prognostic biomarker in cancer patients? Cancer Epidemiol. Biomarkers Prev. 15, 194-202.

Johansen J S, Jensen B V, Roslind A, Price P A (2007). Is YKL-40 a new therapeutic target in cancer? Expert. Opin. Ther. Targets. 11, 219-234.

Jung C S, Foerch C, Schanzer A, Heck A, Plate K H, Seifert V, Steinmetz H, Raabe A, Sitzer M (2007). Serum GFAP is a diagnostic marker for glioblastoma multiforme. Brain 130, 3336-3341.

Jung G, Ledbetter J A, Muller-Eberhard H J (1987). Induction of cytotoxicity in resting human T lymphocytes bound to tumor cells by antibody heteroconjugates. Proc Natl Acad Sci USA 84, 4611-4615.

Junker N, Johansen J S, Hansen L T, Lund E L, Kristjansen P E (2005). Regulation of YKL-40 expression during genotoxic or microenvironmental stress in human glioblastoma cells. Cancer Sci. 96, 183-190.

Kajiwara Y, Yamasaki F, Hama S, Yahara K, Yoshioka H, Sugiyama K, Arita K, Kurisu K (2003). Expression of survivin in astrocytic tumors: correlation with malignant grade and prognosis. Cancer 97, 1077-1083.

Kaloshi G, Mokhtari K, Carpentier C, Taillibert S, Lejeune J, Marie Y, Delattre J Y, Godbout R, Sanson M (2007). FABP7 expression in glioblastomas: relation to prognosis, invasion and EGFR status. J Neurooncol. 84, 245-248.

Kato Y, Fujita N, Kunita A, Sato S, Kaneko M, Osawa M, Tsuruo T (2003). Molecular identification of Aggrus/T1alpha as a platelet aggregation-inducing factor expressed in colorectal tumors. J Biol. Chem. 278, 51599-51605.

Kato Y, Kaneko M K, Kunita A, Ito H, Kameyama A, Ogasawara S, Matsuura N, Hasegawa Y, Suzuki-Inoue K, Inoue O, Ozaki Y, Narimatsu H (2008). Molecular analysis of the pathophysiological binding of the platelet aggregation-inducing factor podoplanin to the C-type lectin-like receptor CLEC-2. Cancer Sci. 99, 54-61.

Kato Y, Kaneko M K, Kuno A, Uchiyama N, Amano K, Chiba Y, Hasegawa Y, Hirabayashi J, Narimatsu H, Mishima K, Osawa M (2006). Inhibition of tumor cell-induced platelet aggregation using a novel anti-podoplanin antibody reacting with its platelet-aggregation-stimulating domain. Biochem. Biophys. Res. Commun. 349, 1301-1307.

Ke N, Sundaram R, Liu G, Chionis J, Fan W, Rogers C, Awad T, Grifman M, Yu D, Wong-Staal F, Li Q X (2007). Orphan G protein-coupled receptor GPR56 plays a role in cell transformation and tumorigenesis involving the cell adhesion pathway. Mol. Cancer Ther. 6, 1840-1850.

Kennedy R C, Shearer M H, Watts A M, Bright R K (2003). CD4+ T lymphocytes play a critical role in antibody production and tumor immunity against simian virus 40 large tumor antigen. Cancer Res. 63, 1040-1045.

Kim C H, Bak K H, Kim Y S, Kim J M, Ko Y, Oh S J, Kim K M, Hong E K (2000). Expression of tenascin-C in astrocytic tumors: its relevance to proliferation and angiogenesis. Surg Neurol. 54, 235-240.

Kim S H, Das K, Noreen S, Coffman F, Hameed M (2007). Prognostic implications of immunohistochemically detected YKL-40 expression in breast cancer. World J Surg Oncol 5,17.

Kleeberger W, Bova G S, Nielsen M E, Herawi M, Chuang A Y, Epstein J I, Berman D M (2007). Roles for the stem cell associated intermediate filament Nestin in prostate cancer migration and metastasis. Cancer Res. 67, 9199-9206.

Klein T, Ling Z, Heimberg H, Madsen O D, Heller R S, Serup P (2003). Nestin is expressed in vascular endothelial cells in the adult human pancreas. J Histochem. Cytochem. 51, 697-706.

Klein W M, Wu B P, Zhao S, Wu H, Klein-Szanto A J, Tahan S R (2007). Increased expression of stem cell markers in malignant melanoma. Mod. Pathol. 20, 102-107.

Kobayashi H, Omiya R, Ruiz M, Huarte E, Sarobe P, Lasarte J J, Herraiz M, Sangro B, Prieto J, Borras-Cuesta F, Celis E (2002). Identification of an antigenic epitope for helper T lymphocytes from carcinoembryonic antigen. Clin Cancer Res. 8, 3219-3225.

Kono T, Shimoda M, Takahashi M, Matsumoto K, Yoshimoto T, Mizutani M, Tabata C, Okoshi K, Wada H, Kubo H (2007). Immunohistochemical detection of the lymphatic marker podoplanin in diverse types of human cancer cells using a novel antibody. Int J Oncol 31, 501-508.

Kosari F, Parker A S, Kube D M, Lohse C M, Leibovich B C, Blute M L, Cheville J C, Vasmatzis G (2005). Clear cell renal cell carcinoma: gene expression analyses identify a potential signature for tumor aggressiveness. Clin Cancer Res. 11, 5128-5139.

Kroes R A, Dawson G, Moskal J R (2007). Focused microarray analysis of glyco-gene expression in human glioblastomas. J Neurochem. 103 Suppl 1, 14-24.

Krona A, Aman P, Orndal C, Josefsson A (2007). Oncostatin M-induced genes in human astrocytomas. Int. J Oncol 31, 1457-1463.

Kucharczak J, Pannequin J, Camby I, Decaestecker C, Kiss R, Martinez J (2001). Gastrin induces over-expression of genes involved in human U373 glioblastoma cell migration. Oncogene 20, 7021-7028.

Kucur M, Isman F K, Balci C, Onal B, Hacibekiroglu M, Ozkan F, Ozkan A (2008). Serum YKL-40 levels and chitotriosidase activity as potential biomarkers in primary prostate cancer and benign prostatic hyperplasia. Urol. Oncol 26, 47-52.

Kurihara H, Zama A, Tamura M, Takeda J, Sasaki T, Takeuchi T (2000). Glioma/glioblastoma-specific adenoviral gene expression using the nestin gene regulator. Gene Ther. 7, 686-693.

Lal A, Peters H, St C B, Haroon Z A, Dewhirst M W, Strausberg R L, Kaanders J H, van der Kogel A J, Riggins G J (2001). Transcriptional response to hypoxia in human tumors. J Natl. Cancer Inst. 93, 1337-1343.

Lemmel C, Weik S, Eberle U, Dengjel J, Kratt T, Becker H D, Rammensee H G, Stevanovic S (2004). Differential quantitative analysis of MHC ligands by mass spectrometry using stable isotope labeling. Nat. Biotechnol. 22, 450-454.

Lendahl U, Zimmerman L B, McKay R D (1990). CNS stem cells express a new class of intermediate filament protein. Cell 60, 585-595.

Li J Y, Wang H, May S, Song X, Fueyo J, Fuller G N, Wang H (2008a). Constitutive activation of c-Jun N-terminal kinase correlates with histologic grade and EGFR expression in diffuse gliomas. J Neurooncol. 88, 11-17.

Li L, Xu H, Spaulding B O, Cheng L, Simon R, Yao J L, di Sant'agnese P A, Bourne P A, Huang J (2008b). Expression of RNA-binding protein IMP3 (KOC) in benign urothelium and urothelial tumors. Hum. Pathol.

Liang M L, Ma J, Ho M, Solomon L, Bouffet E, Rutka J T, Hawkins C (2008). Tyrosine kinase expression in pediatric high grade astrocytoma. J Neurooncol. 87, 247-253.

Liang Y, Bollen A W, Aldape K D, Gupta N (2006). Nuclear FABP7 immunoreactivity is preferentially expressed in infiltrative glioma and is associated with poor prognosis in EGFR-overexpressing glioblastoma. BMC. Cancer 6, 97.

Liang Y, Diehn M, Watson N, Bollen A W, Aldape K D, Nicholas M K, Lamborn K R, Berger M S, Botstein D, Brown P O, Israel M A (2005). Gene expression profiling reveals molecularly and clinically distinct subtypes of glioblastoma multiforme. Proc. Natl. Acad. Sci. U.S.A 102, 5814-5819.

Liao B, Hu Y, Herrick D J, Brewer G (2005). The RNA-binding protein IMP-3 is a translational activator of insulin-like growth factor II leader-3 mRNA during proliferation of human K562 leukemia cells. J Biol. Chem. 280, 18517-18524.

Littaua R A, Takeda A, Cruz J, Ennis F A (1992). Vaccinia virus-specific human CD4+ cytotoxic T-lymphocyte clones. J Virol. 66, 2274-2280.

Liu M, Parker R M, Darby K, Eyre H J, Copeland N G, Crawford J, Gilbert D J, Sutherland G R, Jenkins N A, Herzog H (1999). GPR56, a novel secretin-like human G-protein-coupled receptor gene. Genomics 55, 296-305.

Liu S, Ginestier C, Charafe-Jauffret E, Foco H, Kleer C G, Merajver S D, Dontu G, Wicha M S (2008). BRCA1 regulates human mammary stem/progenitor cell fate. Proc Natl. Acad. Sci. U.S.A 105, 1680-1685.

Liu W, Putnam A L, Xu-Yu Z, Szot G L, Lee M R, Zhu S, Gottlieb P A, Kapranov P, Gingeras T R, de St Groth B F, Clayberger C, Soper D M, Ziegler S F, Bluestone J A (2006a). CD127 expression inversely correlates with FoxP3 and suppressive function of human CD4(+) T reg cells. J Exp. Med 203, 1701-1711.

Liu X, Chen N, Wang X, He Y, Chen X, Huang Y, Yin W, Zhou Q (2006b). Apoptosis and proliferation markers in diffusely infiltrating astrocytomas: profiling of 17 molecules. J Neuropathol. Exp. Neurol. 65, 905-913.

Lo M L, Staibano S, Pannone G, Mignogna M D, Mariggio A, Salvatore G, Chieffi P, Tramontano D, De R G, Altieri D C (2001). Expression of the apoptosis inhibitor survivin in aggressive squamous cell carcinoma. Exp. Mol. Pathol. 70, 249-254.

Lubensky I A, Vortmeyer A O, Kim S, Lonser R R, Park D M, Ikejiri B, Li J, Okamoto H, Walbridge S, Ryschkewitsch C, Major E, Oldfield E H, Zhuang Z (2006). Identification of tumor precursor cells in the brains of primates with radiation-induced de novo glioblastoma multiforme. Cell Cycle 5, 452-456.

Mach B, Steimle V, Martinez-Soria E, Reith W (1996). Regulation of MHC class II genes: lessons from a disease. Annu. Rev. Immunol. 14, 301-331.

Maderna E, Salmaggi A, Calatozzolo C, Limido L, Pollo B (2007). Nestin, PDGFRbeta, CXCL12 and VEGF in Glioma Patients: Different Profiles of (Pro-Angiogenic) Molecule Expression Are Related with Tumor Grade and May Provide Prognostic Information. Cancer Biol. Ther. 6.

Mahlamaki E H, Barlund M, Tanner M, Gorunova L, Hoglund M, Karhu R, Kallioniemi A (2002). Frequent amplification of 8q24, 11q, 17q, and 20q-specific genes in pancreatic cancer. Genes Chromosomes. Cancer 35, 353-358.

Malcherek G, Gnau V, Stevanovic S, Rammensee H G, Jung G, Melms A (1994). Analysis of allele-specific contact sites of natural HLA-DR17 ligands. J Immunol. 153, 1141-1149.

Manici S, Sturniolo T, Imro M A, Hammer J, Sinigaglia F, Noppen C, Spagnoli G, Mazzi B, Bellone M, Dellabona P, Protti M P (1999). Melanoma cells present a MAGE-3 epitope to CD4(+) cytotoxic T cells in association with histocompatibility leukocyte antigen DR11. J Exp. Med 189, 871-876.

Mao Y, Zhou L, Zhu W, Wang X, Yang G, Xie L, Mao X, Jin K (2007). Proliferative status of tumor stem cells may be correlated with malignancy grade of human astrocytomas. Front Biosci. 12, 2252-2259.

Marzo A L, Kinnear B F, Lake R A, Frelinger J J, Collins E J, Robinson B W, Scott B (2000). Tumor-specific CD4+ T cells have a major "post-licensing" role in CTL mediated anti-tumor immunity. J Immunol. 165, 6047-6055.

Mellai M, Caldera V, Patrucco A, Annovazzi L, Schiffer D (2008). Survivin expression in glioblastomas correlates with proliferation, but not with apoptosis. Anticancer Res. 28, 109-118.

Mishima K, Kato Y, Kaneko M K, Nishikawa R, Hirose T, Matsutani M (2006). Increased expression of podoplanin in malignant astrocytic tumors as a novel molecular marker of malignant progression. Acta Neuropathol. 111, 483-488.

Mita R, Coles J E, Glubrecht D D, Sung R, Sun X, Godbout R (2007). B-FABP-expressing radial glial cells: the malignant glioma cell of origin? Neoplasia. 9, 734-744.

Miyawaki T, Uemura A, Dezawa M, Yu R T, Ide C, Nishikawa S, Honda Y, Tanabe Y, Tanabe T (2004). Tlx, an orphan nuclear receptor, regulates cell numbers and astrocyte development in the developing retina. J Neurosci. 24, 8124-8134.

Mizukami Y, Kono K, Daigo Y, Takano A, Tsunoda T, Kawaguchi Y, Nakamura Y, Fujii H (2008). Detection of novel cancer-testis antigen-specific T-cell responses in TIL, regional lymph nodes, and PBL in patients with esophageal squamous cell carcinoma. Cancer Sci.

Mokhtari K, Paris S, guirre-Cruz L, Privat N, Criniere E, Marie Y, Hauw J J, Kujas M, Rowitch D, Hoang-Xuan K, Delattre J Y, Sanson M (2005). Olig2 expression, GFAP, p53 and 1p loss analysis contribute to glioma subclassification. Neuropathol. Appl. Neurobiol. 31, 62-69.

Mokry J, Cizkova D, Filip S, Ehrmann J, Osterreicher J, Kolar Z, English D (2004). Nestin expression by newly formed human blood vessels. Stem Cells Dev. 13, 658-664.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A (2006). Cancer Regression in Patients After Transfer of Genetically Engineered Lymphocytes. Science.

Mortara L, Castellani P, Meazza R, Tosi G, De Lerma B A, Procopio F A, Comes A, Zardi L, Ferrini S, Accolla R S (2006). CIITA-induced MHC class II expression in mammary adenocarcinoma leads to a Th1 polarization of the tumor microenvironment, tumor rejection, and specific antitumor memory. Clin Cancer Res. 12, 3435-3443.

Novellino L, Castelli C, Parmiani G (2005). A listing of human tumor antigens recognized by T cells: March 2004 update. Cancer Immunol. Immunother. 54, 187-207.

Nutt C L, Betensky R A, Brower M A, Batchelor T T, Louis D N, Stemmer-Rachamimov A O (2005). YKL-40 is a differential diagnostic marker for histologic subtypes of high-grade gliomas. Clin Cancer Res. 11, 2258-2264.

Nutt C L, Matthews R T, Hockfield S (2001). Glial tumor invasion: a role for the upregulation and cleavage of BEHAB/brevican. Neuroscientist. 7, 113-122.

O'Driscoll L, Linehan R, Clynes M (2003). Survivin: role in normal cells and in pathological conditions. Curr. Cancer Drug Targets. 3, 131-152.

Ohike N, Sato M, Hisayuki T, Imataka H, Sato S, Wada Y, Saito K, Takahashi M, Tajiri T, Kunimura T, Morohoshi T (2007). Immunohistochemical analysis of nestin and c-kit and their significance in pancreatic tumors. Pathol. Int. 57, 589-593.

Okada Y, Ohno C, Ueki K, Ogino M, Kawamoto S, Kim P (2007). Comparison of numerical change of epidermal growth factor receptor gene among pre- and postradiation glioma, and gliosis, and its clinical use. Brain Tumor Pathol. 24, 15-18.

Ozerdem U (2006). Targeting of pericytes diminishes neovascularization and lymphangiogenesis in prostate cancer. Prostate 66, 294-304.

Pei Z, Oey N A, Zuidervaart M M, Jia Z, Li Y, Steinberg S J, Smith K D, Watkins P A (2003). The acyl-CoA synthetase "bubblegum" (lipidosin): further characterization and role in neuronal fatty acid beta-oxidation. J Biol. Chem. 278, 47070-47078.

Pelloski C E, Lin E, Zhang L, Yung W K, Colman H, Liu J L, Woo S Y, Heimberger A B, Suki D, Prados M, Chang S, Barker F G, III, Fuller G N, Aldape K D (2006). Prognostic associations of activated mitogen-activated protein kinase and Akt pathways in glioblastoma. Clin Cancer Res. 12, 3935-3941.

Pelloski C E, Mahajan A, Maor M, Chang E L, Woo S, Gilbert M, Colman H, Yang H, Ledoux A, Blair H, Passe S, Jenkins R B, Aldape K D (2005). YKL-40 expression is associated with poorer response to radiation and shorter overall survival in glioblastoma. Clin Cancer Res. 11, 3326-3334.

Penar P L, Khoshyomn S, Bhushan A, Tritton T R (1997). Inhibition of epidermal growth factor receptor-associated tyrosine kinase blocks glioblastoma invasion of the brain. Neurosurgery 40, 141-151.

Penna A, Fowler P, Bertoletti A, Guilhot S, Moss B, Margolskee R F, Cavalli A, Valli A, Fiaccadori F, Chisari F V, (1992). Hepatitis B virus (HBV)-specific cytotoxic T-cell (CTL) response in humans: characterization of HLA class II-restricted CTLs that recognize endogenously synthesized HBV envelope antigens. J Virol. 66, 1193-1198.

Peris L, Thery M, Faure J, Saoudi Y, Lafanechere L, Chilton J K, Gordon-Weeks P, Galjart N, Bornens M, Wordeman L, Wehland J, Andrieux A, Job D (2006). Tubulin tyrosination is a major factor affecting the recruitment of CAP-Gly proteins at microtubule plus ends. J Cell Biol. 174, 839-849.

Perry J, Ho M, Viero S, Zheng K, Jacobs R, Thorner P S (2007). The intermediate filament nestin is highly expressed in normal human podocytes and podocytes in glomerular disease. Pediatr. Dev. Pathol. 10, 369-382.

Piesche M, Hildebrandt Y, Zettl F, Chapuy B, Schmitz M, Wulf G, Trumper L, Schroers R (2007). Identification of a promiscuous HLA DR-restricted T-cell epitope derived from the inhibitor of apoptosis protein survivin. Hum. Immunol. 68, 572-576.

Pizzagalli F, Hagenbuch B, Stieger B, Klenk U, Folkers G, Meier P J (2002). Identification of a novel human organic anion transporting polypeptide as a high affinity thyroxine transporter. Mol. Endocrinol. 16, 2283-2296.

Pryor J G, Bourne P A, Yang Q, Spaulding B O, Scott G A, Xu H (2008). IMP-3 is a novel progression marker in malignant melanoma. Mod. Pathol. 21, 431-437.

Purow B, Sundaresan T K, Burdick M J, Kefas B, Comeau L, Hawkinson M, Su Q, Kotliarov Y, Lee J, Zhang W, Fine H A (2008). Notch-1 Regulates Transcription of the Epidermal Growth Factor Receptor Through p53. Carcinogenesis.

Qin Z, Blankenstein T (2000). CD4+ T cell-mediated tumor rejection involves inhibition of angiogenesis that is dependent on IFN gamma receptor expression by nonhematopoietic cells. Immunity. 12, 677-686.

Qin Z, Schwartzkopff J, Pradera F, Kammertoens T, Seliger B, Pircher H, Blankenstein T (2003). A critical requirement of interferon gamma-mediated angiostasis for tumor rejection by CD8+ T cells. Cancer Res. 63, 4095-4100.

Quaranta M, Divella R, Daniele A, Di T S, Venneri M T, Lolli I, Troccoli G (2007). Epidermal growth factor receptor serum levels and prognostic value in malignant gliomas. Tumori 93, 275-280.

Rammensee H G, Bachmann J, Emmerich N P, Bachor O A, Stevanovic S (1999). SYFPEITHI: database for MHC ligands and peptide motifs. Immunogenetics 50, 213-219.

Rammensee, H. G., Bachmann,J., and Stevanovic, S. (1997). MHC Ligands and Peptide Motifs. Springer-Verlag, Heidelberg, Germany).

Rammensee H G, Friede T, Stevanoviic S (1995). MHC ligands and peptide motifs: first listing. Immunogenetics 41, 178-228.

Reyaz N, Tayyab M, Khan S A, Siddique T (2005). Correlation of glial fibrillary acidic protein (GFAP) with grading of the neuroglial tumours. J Coll. Physicians Surg. Pak. 15, 472-475.

Ringsholt M, Hogdall E V, Johansen J S, Price P A, Christensen L H (2007). YKL-40 protein expression in normal adult human tissues—an immunohistochemical study. J Mol. Histol. 38, 33-43.

Rosenberg S A, Lotze M T, Muul L M, Chang A E, Avis F P, Leitman S, Linehan W M, Robertson C N, Lee R E, Rubin J T, (1987). A progress report on the treatment of 157 patients with advanced cancer using lymphokine-activated killer cells and interleukin-2 or high-dose interleukin-2 alone. N. Engl. J. Med. 316, 889-897.

Rosenberg S A, Packard B S, Aebersold P M, Solomon D, Topalian S L, Toy S T, Simon P, Lotze M T, Yang J C, Seipp C A, (1988). Use of tumor-infiltrating lymphocytes and interleukin-2 in the immunotherapy of patients with metastatic melanoma. A preliminary report. N. Engl. J Med 319, 1676-1680.

Roslind A, Johansen J S, Christensen I J, Kiss K, Balslev E, Nielsen D L, Bentzen J, Price P A, Andersen E (2008). High serum levels of YKL-40 in patients with squamous cell carcinoma of the head and neck are associated with short survival. Int. J Cancer 122, 857-863.

Ruiz C, Huang W, Hegi M E, Lange K, Hamou M F, Fluri E, Oakeley E J, Chiquet-Ehrismann R, Orend G (2004). Growth promoting signaling by tenascin-C [corrected]. Cancer Res. 64, 7377-7385.

Sabatini F, Petecchia L, Tavian M, Jodon dV, V, Rossi G A, Brouty-Boye D (2005). Human bronchial fibroblasts exhibit a mesenchymal stem cell phenotype and multilineage differentiating potentialities. Lab Invest 85, 962-971.

Saidi A, Javerzat S, Bellahcene A, De V J, Bello L, Castronovo V, Deprez M, Loiseau H, Bikfalvi A, Hagedorn M (2007). Experimental anti-angiogenesis causes upregulation of genes associated with poor survival in glioblastoma. Int. J Cancer.

Saito T, Arifin M T, Hama S, Kajiwara Y, Sugiyama K, Yamasaki F, Hidaka T, Arita K, Kurisu K (2007). Survivin subcellular localization in high-grade astrocytomas: simultaneous expression in both nucleus and cytoplasm is negative prognostic marker. J Neurooncol. 82, 193-198.

Sakurada K, Saino M, Mouri W, Sato A, Kitanaka C, Kayama T (2007). Nestin expression in central nervous system germ cell tumors. Neurosurg. Rev.

Sarlomo-Rikala M, Tsujimura T, Lendahl U, Miettinen M (2002). Patterns of nestin and other intermediate filament expression distinguish between gastrointestinal stromal tumors, leiomyomas and schwannomas. APMIS 110, 499-507.

Sasaki T, Lopes M B, Hankins G R, Helm G A (2002). Expression of survivin, an inhibitor of apoptosis protein, in tumors of the nervous system. Acta Neuropathol. 104, 105-109.

Sato F, Abraham J M, Yin J, Kan T, Ito T, Mori Y, Hamilton J P, Jin Z, Cheng Y, Paun B, Berki A T, Wang S, Shimada Y, Meltzer S J (2006). Polo-like kinase and survivin are esophageal tumor-specific promoters. Biochem. Biophys. Res. Commun. 342, 465-471.

Schacht V, Dadras S S, Johnson L A, Jackson D G, Hong Y K, Detmar M (2005). Up-regulation of the lymphatic marker podoplanin, a mucin-type transmembrane glycoprotein, in human squamous cell carcinomas and germ cell tumors. Am J Pathol. 166, 913-921.

Schiffer D, Manazza A, Tamagno I (2006). Nestin expression in neuroepithelial tumors. Neurosci. Lett. 400, 80-85.

Schlegel J, Merdes A, Stumm G, Albert F K, Forsting M, Hynes N, Kiessling M (1994). Amplification of the epidermal-growth-factor-receptor gene correlates with different growth behaviour in human glioblastoma. Int. J Cancer 56, 72-77.

Schlehofer B, Blettner M, Preston-Martin S, Niehoff D, Wahrendorf J, Arslan A, Ahlbom A, Choi W N, Giles G G, Howe G R, Little J, Menegoz F, Ryan P (1999). Role of medical history in brain tumour development. Results from the international adult brain tumour study. Int. J Cancer 82, 155-160.

Schmitt A, Gofferje V, Weber M, Meyer J, Mossner R, Lesch K P (2003). The brain-specific protein MLC1 implicated in megalencephalic leukoencephalopathy with subcortical cysts is expressed in glial cells in the murine brain. Glia 44, 283-295.

Schoenberger S P, Toes R E, van d, V, Offringa R, Melief C J (1998). T-cell help for cytotoxic T lymphocytes is mediated by CD40-CD40L interactions. Nature 393, 480-483.

Schwartzbaum J, Jonsson F, Ahlbom A, Preston-Martin S, Lonn S, Soderberg K C, Feychting M (2003). Cohort studies of association between self-reported allergic conditions, immune-related diagnoses and glioma and meningioma risk. Int. J Cancer 106, 423-428.

Schwartzbaum J, Jonsson F, Ahlbom A, Preston-Martin S, Malmer B, Lonn S, Soderberg K, Feychting M (2005). Prior hospitalization for epilepsy, diabetes, and stroke and subsequent glioma and meningioma risk. Cancer Epidemiol. Biomarkers Prev. 14, 643-650.

Schwechheimer K, Huang S, Cavenee W K (1995). EGFR gene amplification—rearrangement in human glioblastomas. Int. J Cancer 62, 145-148.

Scrideli C A, Carlotti C G, Jr., Okamoto O K, Andrade V S, Cortez M A, Motta F J, Lucio-Eterovic A K, Neder L, Rosemberg S, Oba-Shinjo S M, Marie S K, Tone L G (2008). Gene expression profile analysis of primary glioblastomas and non-neoplastic brain tissue: identification of potential target genes by oligonucleotide microarray and real-time quantitative PCR. J Neurooncol.

Sehgal A, Boynton A L, Young R F, Vermeulen S S, Yonemura K S, Kohler E P, Aldape H C, Simrell C R, Murphy G P (1998). Cell adhesion molecule Nr-CAM is over-expressed in human brain tumors. Int J Cancer 76, 451-458.

Sehgal A, Ricks S, Warrick J, Boynton A L, Murphy G P (1999). Antisense human neuroglia related cell adhesion molecule hNr-CAM, reduces the tumorigenic properties of human glioblastoma cells. Anticancer Res. 19, 4947-4953.

Shashidhar S, Lorente G, Nagavarapu U, Nelson A, Kuo J, Cummins J, Nikolich K, Urfer R, Foehr E D (2005). GPR56 is a GPCR that is overexpressed in gliomas and functions in tumor cell adhesion. Oncogene 24, 1673-1682.

Shedlock D J, Shen H (2003). Requirement for CD4 T cell help in generating functional CD8 T cell memory. Science 300, 337-339.

Shibahara J, Kashima T, Kikuchi Y, Kunita A, Fukayama M (2006). Podoplanin is expressed in subsets of tumors of the central nervous system. Virchows Arch. 448, 493-499.

Shih A H, Holland E C (2006). Notch signaling enhances nestin expression in gliomas. Neoplasia. 8, 1072-1082.

Shiras A, Chettiar S T, Shepal V, Rajendran G, Prasad G R, Shastry P (2007). Spontaneous transformation of human adult nontumorigenic stem cells to cancer stem cells is driven by genomic instability in a human model of glioblastoma. Stem Cells 25, 1478-1489.

Shostak K, Labunskyy V, Dmitrenko V, Malisheva T, Shamayev M, Rozumenko V, Zozulya Y, Zehetner G, Kaysan V (2003). HC gp-39 gene is upregulated in glioblastomas. Cancer Lett. 198, 203-210.

Singh S K, Clarke I D, Hide T, Dirks P B (2004a). Cancer stem cells in nervous system tumors. Oncogene 23, 7267-7273.

Singh S K, Clarke I D, Terasaki M, Bonn V E, Hawkins C, Squire J, Dirks P B (2003). Identification of a cancer stem cell in human brain tumors. Cancer Res. 63, 5821-5828.

Singh S K, Hawkins C, Clarke I D, Squire J A, Bayani J, Hide T, Henkelman R M, Cusimano M D, Dirks P B (2004b). Identification of human brain tumour initiating cells. Nature 432, 396-401.

Singh-Jasuja H, Emmerich N P, Rammensee H G (2004). The Tubingen approach: identification, selection, and validation of tumor-associated HLA peptides for cancer therapy. Cancer Immunol. Immunother. 53, 187-195.

Sitnikova L, Mendese G, Liu Q, Woda B A, Lu D, Dresser K, Mohanty S, Rock K L, Jiang Z (2008). IMP3 predicts aggressive superficial urothelial carcinoma of the bladder. Clin Cancer Res. 14, 1701-1706.

Sjo A, Magnusson K E, Peterson K H (2005). Association of alpha-dystrobrevin with reorganizing tight junctions. J Membr. Biol. 203, 21-30.

Span P N, Sweep F C, Wiegerinck E T, Tjan-Heijnen V C, Manders P, Beex L V, de Kok J B (2004). Survivin is an independent prognostic marker for risk stratification of breast cancer patients. Clin Chem. 50, 1986-1993.

Standifer N E, Ouyang Q, Panagiotopoulos C, Verchere C B, Tan R, Greenbaum C J, Pihoker C, Nepom G T (2006). Identification of Novel HLA-A*0201-Restricted Epitopes in Recent-Onset Type 1 Diabetic Subjects and Antibody-Positive Relatives. Diabetes 55, 3061-3067.

Strojnik T, Rosland G V, Sakariassen P O, Kavalar R, Lah T (2007). Neural stem cell markers, nestin and musashi proteins, in the progression of human glioma: correlation of nestin with prognosis of patient survival. Surg Neurol. 68, 133-143.

Su W, Chen J, Yang H, You L, Xu L, Wang X, Li R, Gao L, Gu Y, Lin S, Xu H, Breyer M D, Hao C M (2007). Expression of nestin in the podocytes of normal and diseased human kidneys. Am J Physiol Regul. Integr. Comp Physiol 292, R1761-R1767.

Sugawara K, Kurihara H, Negishi M, Saito N, Nakazato Y, Sasaki T, Takeuchi T (2002). Nestin as a marker for proliferative endothelium in gliomas. Lab Invest 82, 345-351.

Sun G, Yu R T, Evans R M, Shi Y (2007). Orphan nuclear receptor TLX recruits histone deacetylases to repress transcription and regulate neural stem cell proliferation. Proc Natl. Acad. Sci. U.S.A 104, 15282-15287.

Sun J C, Bevan M J (2003). Defective CD8 T cell memory following acute infection without CD4 T cell help. Science 300, 339-342.

Suzuki H, Kato Y, Kaneko M K, Okita Y, Narimatsu H, Kato M (2008). Induction of podoplanin by transforming growth factor-beta in human fibrosarcoma. FEBS Lett. 582, 341-345.

Suzuki T, Maruno M, Wada K, Kagawa N, Fujimoto Y, Hashimoto N, Izumoto S, Yoshimine T (2004). Genetic analysis of human glioblastomas using a genomic microarray system. Brain Tumor Pathol. 21, 27-34.

Takano T, Becker L E (1997). Developmental change of the nestin-immunoreactive midline raphe glial structure in human brainstem and spinal cord. Dev. Neurosci. 19, 202-209.

Tan H Y, Liu J, Wu S M, Luo H S (2005). Expression of a novel apoptosis inhibitor-survivin in colorectal carcinoma. World J Gastroenterol. 11, 4689-4692.

Tanwar M K, Gilbert M R, Holland E C (2002). Gene expression microarray analysis reveals YKL-40 to be a potential serum marker for malignant character in human glioma. Cancer Res. 62, 4364-4368.

Teranishi N, Naito Z, Ishiwata T, Tanaka N, Furukawa K, Seya T, Shinji S, Tajiri T (2007). Identification of neovasculature using nestin in colorectal cancer. Int. J Oncol 30, 593-603.

Teratani T, Domoto T, Kuriki K, Kageyama T, Takayama T, Ishikawa A, Ozono S, Nozawa R (2007). Detection of transcript for brain-type fatty Acid-binding protein in tumor and urine of patients with renal cell carcinoma. Urology 69, 236-240.

Thompson D M, Gill G N (1985). The EGF receptor: structure, regulation and potential role in malignancy. Cancer Surv. 4, 767-788.

Tohyama T, Lee V M, Rorke L B, Marvin M, McKay R D, Trojanowski J Q (1992). Nestin expression in embryonic human neuroepithelium and in human neuroepithelial tumor cells. Lab Invest 66, 303-313.

Tompkins S M, Rota P A, Moore J C, Jensen P E (1993). A europium fluoroimmunoassay for measuring binding of antigen to class II MHC glycoproteins. J Immunol. Methods 163, 209-216.

Toti P, Regoli M, Nesi G, Occhini R, Bartolommei S, Fonzi L, Bertelli E (2005). Nestin expression in normal adrenal gland and adrenocortical tumors. Histol. Histopathol. 20, 1115-1120.

Tsujimura T, Makiishi-Shimobayashi C, Lundkvist J, Lendahl U, Nakasho K, Sugihara A, Iwasaki T, Mano M, Yamada N, Yamashita K, Toyosaka A, Terada N (2001). Expression of the intermediate filament nestin in gastrointestinal stromal tumors and interstitial cells of Cajal. Am J Pathol. 158, 817-823.

Uematsu M, Ohsawa I, Aokage T, Nishimaki K, Matsumoto K, Takahashi H, Asoh S, Teramoto A, Ohta S (2005). Prognostic significance of the immunohistochemical index of survivin in glioma: a comparative study with the MIB-1 index. J Neurooncol. 72, 231-238.

van Bilsen J H, van D H, Lard L R, van d, V, Elferink D G, Bakker A M, Miltenburg A M, Huizinga T W, de Vries R R, Toes R E (2004). Functional regulatory immune responses against human cartilage glycoprotein-39 in health vs. proinflammatory responses in rheumatoid arthritis. Proc. Natl. Acad. Sci. U.S.A 101, 17180-17185.

van der Bruggen P, Traversari C, Chomez P, Lurquin C, De P E, Van den E B, Knuth A, Boon T (1991). A gene encoding an antigen recognized by cytolytic T lymphocytes on a human melanoma. Science 254, 1643-1647.

Vanderwinden J M, Gillard K, De Laet M H, Messam C A, Schiffmann S N (2002). Distribution of the intermediate filament nestin in the muscularis propria of the human gastrointestinal tract. Cell Tissue Res. 309, 261-268.

Veerkamp J H, Zimmerman A W (2001). Fatty acid-binding proteins of nervous tissue. J Mol. Neurosci. 16, 133-142.

Veselska R, Kuglik P, Cejpek P, Svachova H, Neradil J, Loja T, Relichova J (2006). Nestin expression in the cell lines derived from glioblastoma multiforme. BMC. Cancer 6, 32.

Viapiano M S, Bi W L, Piepmeier J, Hockfield S, Matthews R T (2005). Novel tumor-specific isoforms of BEHAB/brevican identified in human malignant gliomas. Cancer Res. 65, 6726-6733.

Viapiano M S, Hockfield S, Matthews R T (2008). BEHAB/brevican requires ADAMTS-mediated proteolytic cleavage to promote glioma invasion. J Neurooncol.

Vigneron N, Stroobant V, Chapiro J, Ooms A, Degiovanni G, Morel S, van der B P, Boon T, Van Den Eynde B J (2004). An antigenic peptide produced by peptide splicing in the proteasome. Science 304, 587-590.

Vogt A B, Kropshofer H, Kalbacher H, Kalbus M, Rammensee H G, Coligan J E, Martin R (1994). Ligand motifs of HLA-DRB5*0101 and DRB1*1501 molecules delineated from self-peptides. J Immunol. 153, 1665-1673.

Walter S, Herrgen L, Schoor O, Jung G, Wernet D, Buhring H J, Rammensee H G, Stevanovic S (2003). Cutting edge: predetermined avidity of human CD8 T cells expanded on calibrated MHC/anti-CD28-coated microspheres. J. Immunol. 171, 4974-4978.

Wang J C, Livingstone A M (2003). Cutting edge: CD4+ T cell help can be essential for primary CD8+ T cell responses in vivo. J Immunol. 171, 6339-6343.

Wei L C, Shi M, Cao R, Chen L W, Chan Y S (2008). Nestin small interfering RNA (siRNA) reduces cell growth in cultured astrocytoma cells. Brain Res. 1196, 103-112.

Weinschenk T, Gouttefangeas C, Schirle M, Obermayr F, Walter S, Schoor O, Kurek R, Loeser W, Bichler K H, Wernet D, Stevanovic S, Rammensee H G (2002). Integrated functional genomics approach for the design of patient-individual antitumor vaccines. Cancer Res. 62, 5818-5827.

Wicki A, Lehembre F, Wick N, Hantusch B, Kerjaschki D, Christofori G (2006). Tumor invasion in the absence of epithelial-mesenchymal transition: podoplanin-mediated remodeling of the actin cytoskeleton. Cancer Cell 9, 261-272.

Winer S, Tsui H, Lau A, Song A, Li X, Cheung R K, Sampson A, Afifiyan F, Elford A, Jackowski G, Becker D J, Santamaria P, Ohashi P, Dosch H M (2003). Autoimmune islet destruction in spontaneous type 1 diabetes is not beta-cell exclusive. Nat. Med 9, 198-205.

Wiranowska M, Ladd S, Smith S R, Gottschall P E (2006). CD44 adhesion molecule and neuro-glial proteoglycan NG2 as invasive markers of glioma. Brain Cell Biol. 35, 159-172.

Xie D, Zeng Y X, Wang H J, Wen J M, Tao Y, Sham J S, Guan X Y (2006). Expression of cytoplasmic and nuclear Survivin in primary and secondary human glioblastoma. Br. J Cancer 94, 108-114.

Xu L, Begum S, Hearn J D, Hynes R O (2006). GPR56, an atypical G protein-coupled receptor, binds tissue transglutaminase, TG2, and inhibits melanoma tumor growth and metastasis. Proc Natl. Acad. Sci. U.S.A 103, 9023-9028.

Xu L, Hynes R O (2007). GPR56 and TG2: possible roles in suppression of tumor growth by the microenvironment. Cell Cycle 6, 160-165.

Yamashita S, Masuda Y, Kurizaki T, Haga Y, Murayama T, Ikei S, Kamei M, Takeno S, Kawahara K (2007). Survivin expression predicts early recurrence in early-stage breast cancer. Anticancer Res. 27, 2803-2808.

Yang J, Price M A, Neudauer C L, Wilson C, Ferrone S, Xia H, Iida J, Simpson M A, McCarthy J B (2004). Melanoma chondroitin sulfate proteoglycan enhances FAK and ERK activation by distinct mechanisms. J Cell Biol. 165, 881-891.

Yantiss R K, Cosar E, Fischer A H (2008). Use of IMPS in identification of carcinoma in fine needle aspiration biopsies of pancreas. Acta Cytol. 52, 133-138.

Yantiss R K, Woda B A, Fanger G R, Kalos M, Whalen G F, Tada H, Andersen D K, Rock K L, Dresser K (2005). KOC (K homology domain containing protein overexpressed in cancer): a novel molecular marker that distinguishes between benign and malignant lesions of the pancreas. Am J Surg Pathol. 29, 188-195.

Yee C, Thompson J A, Byrd D, Riddell S R, Roche P, Celis E, Greenberg P D (2002). Adoptive T cell therapy using antigen-specific CD8+ T cell clones for the treatment of patients with metastatic melanoma: in vivo persistence, migration, and antitumor effect of transferred T cells. Proc. Natl. Acad. Sci. U.S.A 99, 16168-16173.

yuso-Sacido A, Graham C, Greenfield J P, Boockvar J A (2006). The duality of epidermal growth factor receptor (EGFR) signaling and neural stem cell phenotype: cell enhancer or cell transformer? Curr. Stem Cell Res. Ther. 1, 387-394.

Zangen I, Kneitz S, Monoranu C M, Rutkowski S, Hinkes B, Vince G H, Huang B, Roggendorf W (2007). Ependymoma gene expression profiles associated with histological subtype, proliferation, and patient survival. Acta Neuropathol. 113, 325-337.

Zaremba S, Barzaga E, Zhu M, Soares N, Tsang K Y, Schlom J (1997). Identification of an enhancer agonist cytotoxic T lymphocyte peptide from human carcinoembryonic antigen. Cancer Res. 57, 4570-4577.

Zawrocki A, Biernat W (2005). Epidermal growth factor receptor in glioblastoma. Folia Neuropathol. 43, 123-132.

Zeh H J, III, Perry-Lalley D, Dudley M E, Rosenberg S A, Yang J C (1999). High avidity CTLs for two self-antigens demonstrate superior in vitro and in vivo antitumor efficacy. J Immunol. 162, 989-994.

Zhen H N, Zhang X, Hu P Z, Yang T T, Fei Z, Zhang J N, Fu L A, He X S, Ma F C, Wang X L (2005). Survivin expression and its relation with proliferation, apoptosis, and angiogenesis in brain gliomas. Cancer 104, 2775-2783.

Zheng W, Yi X, Fadare O, Liang S X, Martel M, Schwartz P E, Jiang Z (2008). The oncofetal protein IMP3: a novel biomarker for endometrial serous carcinoma. Am J Surg Pathol. 32, 304-315.

Zhou R, Skalli O (2000). TGF-alpha differentially regulates GFAP, vimentin, and nestin gene expression in U-373 MG glioblastoma cells: correlation with cell shape and motility. Exp. Cell Res. 254, 269-278.

Zimmerman L, Pan B, Lendahl U, Cunningham M, McKay R, Gavin B, Mann J, Vassileva G, McMahon A (1994). Independent regulatory elements in the nestin gene direct transgene expression to neural stem cells or muscle precursors. Neuron 12, 11-24.

Ziu M, Schmidt N O, Cargioli T G, Aboody K S, Black P M, Carroll R S (2006). Glioma-produced extracellular matrix influences brain tumor tropism of human neural stem cells. J Neurooncol. 79, 125-133.

Zukiel R, Nowak S, Wyszko E, Rolle K, Gawronska I, Barciszewska M Z, Barciszewski J (2006). Suppression of human brain tumor with interference RNA specific for tenascin-C. Cancer Biol. Ther. 5, 1002-1007.

Zulewski H, Abraham E J, Gerlach M J, Daniel P B, Moritz W, Muller B, Vallejo M, Thomas M K, Habener J F (2001). Multipotential nestin-positive stem cells isolated from adult pancreatic islets differentiate ex vivo into pancreatic endocrine, exocrine, and hepatic phenotypes. Diabetes 50, 521-533.

---

The invention claimed is:

1. A method of treating glioblastoma in a HLA-A*02+ patient having glioblastoma overexpressing a IGF2BP3 polypeptide comprising the amino acid sequence of SEQ ID NO: 14 and presenting at its surface a peptide consisting of SEQ ID NO: 14 in the context of a complex with an MHC class I molecule, said method comprising administering to said patient an effective amount of activated antigen-specific CD8+ cytotoxic T cells to selectively eliminate the cancer cells, wherein said activated antigen-specific CD8+ cytotoxic T cells are produced by contacting CD8+ cytotoxic T cells with an antigen presenting cell presenting at its surface a peptide consisting of SEQ ID NO: 14 in the context of a complex with an MHC class I molecule in vitro.

2. The method of claim 1, wherein the cytotoxic T cells produced by contacting CD8+ cytotoxic T cells with an antigen presenting cell presenting at its surface a peptide consisting of SEQ ID NO: 14 in the context of a complex with an MHC class I molecule are cytotoxic T cells autologous to the patient.

3. The method of claim 1, wherein the cytotoxic T cells produced by contacting CD8+ cytotoxic T cells with an antigen presenting cell presenting at its surface a peptide consisting of SEQ ID NO: 14 in the context of a complex with an MHC class I molecule are cytotoxic T cells obtained from a healthy donor.

4. The method of claim 1, wherein the cytotoxic T cells produced by contacting CD8+ cytotoxic T cells with an antigen presenting cell presenting at its surface a peptide consisting of SEQ ID NO: 14 in the context of a complex with an MHC class I molecule are cytotoxic T cells isolated from tumor infiltrating lymphocytes or peripheral blood mononuclear cells.

5. The method of claim 1, wherein the cytotoxic T cells produced by contacting CD8+ cytotoxic T cells with an antigen presenting cell presenting at its surface a peptide consisting of SEQ ID NO: 14 in the context of a complex with an MHC class I molecule are expanded in vitro before being administered to the patient.

6. The method of claim 5, wherein the cytotoxic T cells are expanded in vitro in the presence of an anti-CD28 antibody and IL-12.

7. The method of claim 1, wherein the effective amount of activated antigen-specific CD8+ cytotoxic T cells to selectively eliminate the cancer cells is administered in the form of a composition.

8. The method of claim 1, wherein said composition further comprises an adjuvant.

9. The method of claim 8, wherein said adjuvant is selected from imiquimod, resiquimod, GM-CSF, cyclophosphamide, sunitinib, interferon-alpha, CpG oligonucleotides, poly-(I:C), RNA, sildenafil, particulate formulations with poly(lactid co-glycolid) (PLG) and virosomes.

10. The method of claim 1, wherein the antigen presenting cell is a dendritic cell or a macrophage.

11. The method of claim 1, wherein the antigen presenting cell is infected with a recombinant virus expressing the peptide consisting of SEQ ID NO: 14.

12. The method of claim 1, wherein the antigen presenting cell is an artificial antigen presenting cell (aAPC) comprising an anti-CD28 antibody coupled to its surface.

* * * * *

SEQUENCE LISTING

```
<160> NUMBER OF SEQ ID NOS: 30

<210> SEQ ID NO 1
<211> LENGTH: 9
<212> TYPE: PRT
<213> ORGANISM: Homo sapiens

<400> SEQUENCE: 1

Asn Leu Asp Thr Leu Met Thr Tyr Val
1               5

<210> SEQ ID NO 2
<211> LENGTH: 9
<212> TYPE: PRT
<213> ORGANISM: Homo sapiens

<400> SEQUENCE: 2

Tyr Leu Ile Ala Gly Ile Ile Ser Leu
1               5

<210> SEQ ID NO 3
<211> LENGTH: 9
<212> TYPE: PRT
<213> ORGANISM: Homo sapiens
```

```
<400> SEQUENCE: 3

Lys Ile Met Glu Arg Ile Gln Glu Val
1               5

<210> SEQ ID NO 4
<211> LENGTH: 9
<212> TYPE: PRT
<213> ORGANISM: Homo sapiens

<400> SEQUENCE: 4

Phe Leu Gly Asp Pro Pro Glu Lys Leu
1               5

<210> SEQ ID NO 5
<211> LENGTH: 9
<212> TYPE: PRT
<213> ORGANISM: Homo sapiens

<400> SEQUENCE: 5

Ala Leu Trp Ala Trp Pro Ser Glu Leu
1               5

<210> SEQ ID NO 6
<211> LENGTH: 9
<212> TYPE: PRT
<213> ORGANISM: Homo sapiens

<400> SEQUENCE: 6

Thr Leu Tyr Gly Met Leu Asn Thr Leu
1               5

<210> SEQ ID NO 7
<211> LENGTH: 9
<212> TYPE: PRT
<213> ORGANISM: Homo sapiens

<400> SEQUENCE: 7

Ser Leu Asn Glu Leu Arg Val Leu Leu
1               5

<210> SEQ ID NO 8
<211> LENGTH: 9
<212> TYPE: PRT
<213> ORGANISM: Homo sapiens

<400> SEQUENCE: 8

Lys Leu Gln Asp Glu Ala Tyr Gln Val
1               5

<210> SEQ ID NO 9
<211> LENGTH: 10
<212> TYPE: PRT
<213> ORGANISM: Homo sapiens

<400> SEQUENCE: 9

Ala Leu Ala Val Leu Ser Asn Tyr Asp Ala
1               5                   10

<210> SEQ ID NO 10
<211> LENGTH: 9
<212> TYPE: PRT
<213> ORGANISM: Homo sapiens

<400> SEQUENCE: 10
```

Leu Thr Phe Gly Asp Val Val Ala Val
1               5

<210> SEQ ID NO 11
<211> LENGTH: 9
<212> TYPE: PRT
<213> ORGANISM: Homo sapiens

<400> SEQUENCE: 11

Asn Leu Ala Gln Asp Leu Ala Thr Val
1               5

<210> SEQ ID NO 12
<211> LENGTH: 9
<212> TYPE: PRT
<213> ORGANISM: Homo sapiens

<400> SEQUENCE: 12

Phe Leu Leu Ser Glu Pro Val Ala Leu
1               5

<210> SEQ ID NO 13
<211> LENGTH: 9
<212> TYPE: PRT
<213> ORGANISM: Homo sapiens

<400> SEQUENCE: 13

Asn Ile Leu Glu Gln Ile Val Ser Val
1               5

<210> SEQ ID NO 14
<211> LENGTH: 9
<212> TYPE: PRT
<213> ORGANISM: Homo sapiens

<400> SEQUENCE: 14

Lys Ile Gln Glu Ile Leu Thr Gln Val
1               5

<210> SEQ ID NO 15
<211> LENGTH: 9
<212> TYPE: PRT
<213> ORGANISM: Homo sapiens

<400> SEQUENCE: 15

Ser Val Val Glu Val Ile Ala Gly Ile
1               5

<210> SEQ ID NO 16
<211> LENGTH: 9
<212> TYPE: PRT
<213> ORGANISM: Homo sapiens

<400> SEQUENCE: 16

Gly Leu Gln Ser Gln Ile Ala Gln Val
1               5

<210> SEQ ID NO 17
<211> LENGTH: 9
<212> TYPE: PRT
<213> ORGANISM: Homo sapiens

<400> SEQUENCE: 17

Ser Leu Gln Glu Asn Leu Glu Ser Leu

```
1               5

<210> SEQ ID NO 18
<211> LENGTH: 11
<212> TYPE: PRT
<213> ORGANISM: Homo sapiens

<400> SEQUENCE: 18

Phe Leu Phe Pro Gly Thr Glu Asn Gln Glu Leu
1               5                   10

<210> SEQ ID NO 19
<211> LENGTH: 9
<212> TYPE: PRT
<213> ORGANISM: Homo sapiens

<400> SEQUENCE: 19

Asn Leu Ala Glu Glu Leu Glu Gly Val
1               5

<210> SEQ ID NO 20
<211> LENGTH: 9
<212> TYPE: PRT
<213> ORGANISM: Homo sapiens

<400> SEQUENCE: 20

Lys Ile Ile Ser Glu Ile Gln Ala Leu
1               5

<210> SEQ ID NO 21
<211> LENGTH: 9
<212> TYPE: PRT
<213> ORGANISM: Homo sapiens

<400> SEQUENCE: 21

Gly Leu Trp His His Gln Thr Glu Val
1               5

<210> SEQ ID NO 22
<211> LENGTH: 9
<212> TYPE: PRT
<213> ORGANISM: Homo sapiens

<400> SEQUENCE: 22

Thr Leu Val Gly Ile Ile Val Gly Val
1               5

<210> SEQ ID NO 23
<211> LENGTH: 9
<212> TYPE: PRT
<213> ORGANISM: Homo sapiens

<400> SEQUENCE: 23

Ala Met Thr Gln Leu Leu Ala Gly Val
1               5

<210> SEQ ID NO 24
<211> LENGTH: 9
<212> TYPE: PRT
<213> ORGANISM: Homo sapiens

<400> SEQUENCE: 24

Gln Leu Leu Ala Gly Val Phe Leu Ala
1               5
```

```
<210> SEQ ID NO 25
<211> LENGTH: 9
<212> TYPE: PRT
<213> ORGANISM: Homo sapiens

<400> SEQUENCE: 25

Thr Met Leu Ala Arg Leu Ala Ser Ala
1               5

<210> SEQ ID NO 26
<211> LENGTH: 15
<212> TYPE: PRT
<213> ORGANISM: Homo sapiens

<400> SEQUENCE: 26

Thr Leu Gly Glu Phe Leu Lys Leu Asp Arg Glu Arg Ala Lys Asn
1               5                   10                  15

<210> SEQ ID NO 27
<211> LENGTH: 15
<212> TYPE: PRT
<213> ORGANISM: Homo sapiens

<400> SEQUENCE: 27

Thr Leu Gly Glu Phe Leu Lys Leu Asp Arg Glu Arg Ala Lys Asp
1               5                   10                  15

<210> SEQ ID NO 28
<211> LENGTH: 9
<212> TYPE: PRT
<213> ORGANISM: Homo sapiens

<400> SEQUENCE: 28

Phe Thr Glu Leu Thr Leu Gly Glu Phe
1               5

<210> SEQ ID NO 29
<211> LENGTH: 9
<212> TYPE: PRT
<213> ORGANISM: Homo sapiens

<400> SEQUENCE: 29

Leu Met Leu Gly Glu Phe Leu Lys Leu
1               5

<210> SEQ ID NO 30
<211> LENGTH: 9
<212> TYPE: PRT
<213> ORGANISM: Homo sapiens

<400> SEQUENCE: 30

Glu Pro Asp Leu Ala Gln Cys Phe Tyr
1               5
```